United States Patent
Varga et al.

(10) Patent No.: US 9,022,029 B2
(45) Date of Patent: May 5, 2015

(54) CARBON-DIOXIDE SAMPLING SYSTEM FOR ACCURATELY MONITORING CARBON DIOXIDE IN EXHALED BREATH

(75) Inventors: Christopher M Varga, Laguna Hills, CA (US); Stephen J. Birch, Mission Viejo, CA (US); Brian W. Pierro, Yorba Linda, CA (US)

(73) Assignee: CareFusion 207, Inc., San Diego, CA (US)

( * ) Notice: Subject to any disclaimer, the term of this patent is extended or adjusted under 35 U.S.C. 154(b) by 975 days.

(21) Appl. No.: 13/105,840

(22) Filed: May 11, 2011

(65) Prior Publication Data
US 2012/0289838 A1 Nov. 15, 2012

(51) Int. Cl.
*A61M 11/00* (2006.01)
*A61B 5/083* (2006.01)
*A61B 5/097* (2006.01)
(Continued)

(52) U.S. Cl.
CPC .............. *A61B 5/0836* (2013.01); *A61B 5/097* (2013.01); *A61M 16/06* (2013.01); *A61M 11/00* (2013.01); *A61M 15/00* (2013.01); *A61M 16/044* (2013.01); *A61M 16/0463* (2013.01); *A61M 16/0683* (2013.01); *A61M 16/08* (2013.01); *A61M 16/208* (2013.01); *A61M 2016/0027* (2013.01); *A61M 2016/003* (2013.01); *A61M 2205/02* (2013.01); *A61M 2205/15* (2013.01); *A61M 2205/18* (2013.01); *A61M 2205/3313* (2013.01); *A61M 2205/3331* (2013.01); *A61M 2205/584* (2013.01); *A61M 2205/6027* (2013.01); *A61M 2205/6045* (2013.01); *A61M 2205/6054* (2013.01); *A61M 2205/6072* (2013.01); *A61M 2205/6081* (2013.01); *A61M 2205/75* (2013.01); *A61M 2210/1053* (2013.01); *A61M 2230/432* (2013.01); *A61M 16/0605* (2014.02); *A61M 16/0694* (2014.02); *A61M 16/085* (2014.02)

(58) Field of Classification Search
USPC .......................... 128/204.18–204.23, 205.24
See application file for complete search history.

(56) References Cited

U.S. PATENT DOCUMENTS

| 2,254,854 A | 9/1941 | O'Connell |
| 3,889,671 A | 6/1975 | Baker |

(Continued)

FOREIGN PATENT DOCUMENTS

| EP | 0956065 A1 | 11/1999 |
| EP | 1402915 A1 | 3/2004 |

(Continued)

OTHER PUBLICATIONS

Non-Final Office Action, dated Dec. 5, 2013 for U.S. Appl. No. 13/105,782.

(Continued)

*Primary Examiner* — Steven Douglas
(74) *Attorney, Agent, or Firm* — McDermott Will & Emery LLP

(57) ABSTRACT

A carbon-dioxide sampling system for accurately monitoring carbon dioxide in exhaled breath. The system includes a ventilator. The ventilator is configured to ventilate a patient with respiratory gases. The ventilator includes a carbon-dioxide sampling control unit and a carbon-dioxide analyzer. The carbon-dioxide sampling control unit is configured to control the timing of sampling of carbon dioxide in the exhaled breath of a patient, and to control the timing of the analysis of exhaled gases by the carbon-dioxide analyzer.

21 Claims, 32 Drawing Sheets

(51) Int. Cl.
  *A61M 16/06* (2006.01)
  *A61M 16/08* (2006.01)
  *A61M 15/00* (2006.01)
  *A61M 16/04* (2006.01)
  *A61M 16/20* (2006.01)
  *A61M 16/00* (2006.01)

(56) References Cited

U.S. PATENT DOCUMENTS

| | | |
|---|---|---|
| 4,088,461 A | 5/1978 | Brauer |
| 4,219,020 A | 8/1980 | Czajka |
| 4,328,797 A | 5/1982 | Rollins, III et al. |
| 4,669,462 A | 6/1987 | Marshall |
| 4,770,169 A | 9/1988 | Schmoegner et al. |
| 4,782,832 A | 11/1988 | Trimble et al. |
| 4,799,477 A | 1/1989 | Lewis |
| 4,841,953 A | 6/1989 | Dodrill |
| 4,971,051 A | 11/1990 | Toffolon |
| 5,121,745 A | 6/1992 | Israel |
| 5,280,967 A | 1/1994 | Varrin, Jr. |
| 5,431,158 A | 7/1995 | Tirotta |
| 5,474,060 A | 12/1995 | Evans |
| 5,584,286 A | 12/1996 | Kippax |
| 5,630,412 A | 5/1997 | Dubruille et al. |
| 5,813,423 A | 9/1998 | Kirchgeorg |
| 5,857,460 A | 1/1999 | Popitz |
| 5,918,598 A | 7/1999 | Belfer |
| 6,019,101 A | 2/2000 | Cotner et al. |
| 6,035,852 A | 3/2000 | Hoftman |
| 6,044,844 A | 4/2000 | Kwok et al. |
| 6,135,109 A | 10/2000 | Blasdell et al. |
| 6,196,223 B1 | 3/2001 | Belfer et al. |
| 6,382,208 B2 | 5/2002 | Reedy et al. |
| 6,513,526 B2 | 2/2003 | Kwok et al. |
| 6,626,178 B2 | 9/2003 | Morgan et al. |
| 6,629,531 B2 | 10/2003 | Gleason et al. |
| 6,834,650 B1 | 12/2004 | Fini et al. |
| 6,851,429 B2 | 2/2005 | Bishop |
| 7,152,602 B2 | 12/2006 | Bateman et al. |
| 7,500,482 B2 | 3/2009 | Biederman |
| 7,640,932 B2 | 1/2010 | Curti et al. |
| 7,802,572 B2 | 9/2010 | Hahne |
| 7,845,352 B2 | 12/2010 | Sleeper et al. |
| 7,997,275 B2 | 8/2011 | Quinn |
| 8,020,276 B2 | 9/2011 | Thornton |
| 8,146,591 B2 * | 4/2012 | Niklewski et al. ........ 128/204.23 |
| 8,297,283 B2 | 10/2012 | Hitchcock et al. |
| 8,360,062 B2 | 1/2013 | Berthon-Jones |
| 8,371,293 B2 | 2/2013 | Henry et al. |
| 8,522,784 B2 | 9/2013 | Ng et al. |
| 8,656,913 B2 * | 2/2014 | Kroupa ................... 128/204.18 |
| 8,755,857 B2 * | 6/2014 | Melker et al. ................. 600/344 |
| 2002/0134388 A1 | 9/2002 | Chang |
| 2003/0010344 A1 | 1/2003 | Bird |
| 2003/0024533 A1 | 2/2003 | Sniadach |
| 2003/0047189 A1 | 3/2003 | Kumar et al. |
| 2003/0116159 A1 | 6/2003 | Orr et al. |
| 2003/0127102 A1 | 7/2003 | Strawder et al. |
| 2003/0168063 A1 | 9/2003 | Gambone et al. |
| 2004/0065327 A1 | 4/2004 | Gradon et al. |
| 2004/0244799 A1 | 12/2004 | Landis |
| 2005/0061318 A1 | 3/2005 | Faram |
| 2005/0284484 A1 | 12/2005 | Curti et al. |
| 2006/0081243 A1 | 4/2006 | McDonald et al. |
| 2006/0081248 A1 | 4/2006 | McDonald |
| 2006/0107960 A1 | 5/2006 | Smart |
| 2006/0278221 A1 | 12/2006 | Schermeier et al. |
| 2007/0084468 A1 | 4/2007 | Schafer |
| 2007/0119454 A1 | 5/2007 | Berthon-Jones et al. |
| 2007/0144519 A1 | 6/2007 | Henry et al. |
| 2007/0144525 A1 | 6/2007 | Davidson et al. |
| 2008/0023007 A1 | 1/2008 | Dolezal et al. |
| 2008/0039735 A1 | 2/2008 | Hickerson |
| 2008/0051674 A1 | 2/2008 | Davenport et al. |
| 2008/0072908 A1 | 3/2008 | Lang et al. |
| 2008/0078391 A1 | 4/2008 | Jensen |
| 2008/0092905 A1 | 4/2008 | Gunaratnam et al. |
| 2008/0178875 A1 | 7/2008 | Henry |
| 2008/0245369 A1 | 10/2008 | Matula et al. |
| 2009/0032026 A1 | 2/2009 | Price et al. |
| 2009/0078262 A1 | 3/2009 | Gebrewold et al. |
| 2009/0084385 A1 | 4/2009 | Lang et al. |
| 2009/0095301 A1 | 4/2009 | Hitchcock et al. |
| 2009/0223522 A1 | 9/2009 | Hernandez et al. |
| 2009/0250060 A1 | 10/2009 | Hacke et al. |
| 2009/0277452 A1 | 11/2009 | Lubke et al. |
| 2009/0293880 A1 | 12/2009 | Rutan |
| 2010/0018534 A1 | 1/2010 | Veliss et al. |
| 2010/0024811 A1 | 2/2010 | Henry et al. |
| 2010/0031958 A1 | 2/2010 | Stewart |
| 2010/0031963 A1 | 2/2010 | Lee et al. |
| 2010/0147301 A1 | 6/2010 | Kwok |
| 2010/0154798 A1 | 6/2010 | Henry et al. |
| 2010/0252037 A1 * | 10/2010 | Wondka et al. .......... 128/203.12 |
| 2010/0258136 A1 | 10/2010 | Doherty et al. |
| 2010/0292544 A1 * | 11/2010 | Sherman et al. .............. 600/300 |
| 2010/0319700 A1 | 12/2010 | Ng et al. |
| 2011/0023882 A1 | 2/2011 | Nickol et al. |
| 2011/0079225 A1 | 4/2011 | Vole |
| 2011/0232645 A1 | 9/2011 | Smith |
| 2011/0232647 A1 | 9/2011 | Ho |
| 2011/0265796 A1 | 11/2011 | Amarasinghe et al. |
| 2012/0199131 A1 | 8/2012 | Sofranko et al. |
| 2012/0216806 A1 | 8/2012 | Rookard et al. |
| 2012/0216812 A1 | 8/2012 | Pastoor et al. |
| 2013/0074845 A1 | 3/2013 | Smith et al. |
| 2013/0172768 A1 | 7/2013 | Lehman |

FOREIGN PATENT DOCUMENTS

| | | |
|---|---|---|
| WO | WO-9602300 A1 | 2/1996 |
| WO | WO-9733641 A1 | 9/1997 |

OTHER PUBLICATIONS

Rhoades et al., Capnography: Beyond the Numbers, 2002, Air Medical Journal, 21:2, 43-48.
Watkins, Basic Capnography Presentation, 2009, Virginia EMS Symposium, p. 1-16.
Non-Final Office Action in U.S. Appl. No. 13/105,821 dated Dec. 26, 2012.
International Search Report and Written Opinion for PCT Application No. PCT/US2012/037163 dated Dec. 3, 2012.
Final Office Action in U.S. Appl. No. 13/105,821 dated Jul. 11, 2013.
Non-Final Office Action in U.S. Appl. No. 13/105,821 dated Jun. 6, 2014.
Final Office Action in U.S. Appl. No. 13/105,773 dated Feb. 11, 2014.
Final Office Action in U.S. Appl. No. 13/105,829 dated May 5, 2014.
Final Office Action in U.S. Appl. No. 13/105,871 dated Feb. 4, 2014.
Non-Final Office Action in U.S. Appl. No. 13/105,738 dated Feb. 10, 2014.
Non-Final Office Action in U.S. Appl. No. 13/105,807 dated Jun. 6, 2014.
Non-Final Office Action in U.S. Appl. No. 13/105,848 dated May 8, 2014.
Non-Final Office Action in U.S. Appl. No. 13/105,851 dated Mar. 14, 2014.
Non-Final Office Action in U.S. Appl. No. 13/105,861 dated May 7, 2014.
Final Office Action in U.S. Appl. No. 13/105,861 dated Jul. 5, 2013.
Final Office Action in U.S. Appl. No. 13/105,871 dated May 23, 2013.
Non-Final Office Action in U.S. Appl. No. 13/105,848 dated Dec. 20, 2012.
Final Office Action in U.S. Appl. No. 13/105,807 dated Jul. 5, 2013.
Final Office Action in U.S. Appl. No. 13/105,848 dated Jun. 7, 2013.
Final Office Action in U.S. Appl. No. 13/105,851 dated Aug. 26, 2014.
Final Office Action in U.S. Appl. No. 13/105,851 dated Aug. 5, 2013.

(56) References Cited

OTHER PUBLICATIONS

Non-Final Office Action in U.S. Appl. No. 13/105,738 dated Jul. 29, 2013.
Non-Final Office Action in U.S. Appl. No. 13/105,757 dated Sep. 12, 2013.
Non-Final Office Action in U.S. Appl. No. 13/105,773 dated Aug. 20, 2013.
Non-Final Office Action in U.S. Appl. No. 13/105,782 dated Oct. 8, 2014.
Non-Final Office Action in U.S. Appl. No. 13/105,793 dated Oct. 1, 2013.
Non-Final Office Action in U.S. Appl. No. 13/105,807 dated Dec. 20, 2012.
Non-Final Office Action in U.S. Appl. No. 13/105,829 dated Dec. 6, 2013.
Non-Final Office Action in U.S. Appl. No. 13/105,851 dated Jan. 30, 2013.
Non-Final Office Action in U.S. Appl. No. 13/105,861 dated Dec. 20, 2012.
Non-Final Office Action in U.S. Appl. No. 13/105,871 dated Dec. 26, 2012.
Non-Final Office Action in U.S. Appl. No. 13/105,871 dated Sep. 9, 2013.
Non-Final Office Action dated Feb. 10, 2014 for U.S. Appl. No. 13/105,738.
Non-Final Office Action dated May 7, 2014 for U.S. Appl. No. 13/105,861.
Final Office Action dated Feb. 4, 2014 for U.S. Appl. No. 13/105,871.
Non-Final Office Action dated Jun. 6, 2014 for U.S. Appl. No. 13/105,807.
Non-Final Office Action dated Jun. 6, 2014 for U.S. Appl. No. 13/105,821.
Final Office Action dated May 5, 2014 for U.S. Appl. No. 13/105,829.
Final Office Action dated Apr. 10, 2014 for U.S. Appl. No. 13/105,782.
Non-Final Office Action dated May 8, 2014 for U.S. Appl. No. 13/105,848.
Final Office Action dated Feb. 11, 2014 for U.S. Appl. No. 13/105,773.
Non-Final Office Action dated Mar. 14, 2014 for U.S. Appl. No. 13/105,851.

* cited by examiner

900

```
MEASURE A VENTILATIVE STATE OF THE VENTILATION MASK PLACED
OVER A RESPIRATORY OPENING OF A PATIENT, WHEREIN A SEALING
PORTION OF THE VENTILATION MASK IS FOR ESTABLISHING A FLUID SEAL
BETWEEN THE VENTILATION MASK AND THE PATIENT, AND WHEREIN THE
SEALING PORTION COMPRISES A PLURALITY OF BLADDERS
910
```

| MEASURE AN AIRFLOW | MEASURE A PRESSURE |
|---|---|
| 912 | 914 |

DETERMINE AN UNINTENTIONAL LEAK OF THE FLUID SEAL BASED ON A
MEASURED CHANGE OF THE VENTILATIVE STATE
920

ADJUST A BLADDER OF THE PLURALITY OF BLADDERS TO SEAL THE
UNINTENTIONAL LEAK
930

AUTOMATICALLY ADJUST A BLADDER OF THE PLURALITY OF
BLADDERS TO SEAL THE UNINTENTIONAL LEAK
931

SEQUENTIALLY ADJUST BLADDERS OF THE PLURALITY BLADDERS
932

AUTOMATICALLY ADJUST BLADDERS OF THE PLURALITY BLADDERS
ACCORDING TO A PRE-DEFINED PATTERN
933

ADJUST A BLADDER OF THE PLURALITY OF BLADDERS SUCH THAT A
MEASURED VENTILATIVE STATE RETURNS TO A PRESCRIBED
VENTILATIVE STATE
934

SIMULTANEOUSLY ADJUST MORE THAN ONE BLADDER OF THE
PLURALITY OF BLADDERS
935

```
┌─────────────────────────────────────────────────────────────┐
│ FLUIDLY SEAL THE VENTILATION MASK TO A PATIENT, WHEREIN     │
│ THE VENTILATION MASK COMPRISES A PLURALITY OF               │
│ BLADDERS IN PHYSICAL CONTACT WITH THE PATIENT               │
│ 1010                                                        │
└─────────────────────────────────────────────────────────────┘
                              │
                              ▼
┌─────────────────────────────────────────────────────────────┐
│ ADJUST A BLADDER OF THE PLURALITY OF BLADDERS TO            │
│ DECREASE NECROSIS                                           │
│ 1020                                                        │
│ ┌─────────────────────────────────────────────────────────┐ │
│ │ ADJUST A BLADDER OF THE PLURALITY OF BLADDERS TO        │ │
│ │ DECREASE PRESSURE ON A PRESSURE POINT OF THE            │ │
│ │ PATIENT                                                 │ │
│ │ 1022                                                    │ │
│ └─────────────────────────────────────────────────────────┘ │
│                                                             │
│ ┌─────────────────────────────────────────────────────────┐ │
│ │ INFLATE A BLADDER OF THE PLURALITY OF BLADDERS TO       │ │
│ │ DECREASE NECROSIS                                       │ │
│ │ 1024                                                    │ │
│ └─────────────────────────────────────────────────────────┘ │
│                                                             │
│ ┌─────────────────────────────────────────────────────────┐ │
│ │ DEFLATE A BLADDER OF THE PLURALITY OF BLADDERS TO       │ │
│ │ DECREASE NECROSIS                                       │ │
│ │ 1026                                                    │ │
│ └─────────────────────────────────────────────────────────┘ │
│                                                             │
│ ┌─────────────────────────────────────────────────────────┐ │
│ │ AUTOMATICALLY ADJUST A BLADDER OF THE PLURALITY         │ │
│ │ OF BLADDERS TO DECREASE NECROSIS                        │ │
│ │ 1028                                                    │ │
│ └─────────────────────────────────────────────────────────┘ │
└─────────────────────────────────────────────────────────────┘
```

```
┌─────────────────────────────────────────────────────┐
│   SEAL A VENTILATION MASK OVER A FACE OF A PATIENT, │
│  WHEREIN THE VENTILATION MASK IS DISPOSED OVER A NASAL │
│              PASSAGE OF THE PATIENT                 │
│                        1110                         │
└─────────────────────────────────────────────────────┘
                          │
                          ▼
┌─────────────────────────────────────────────────────┐
│  ASSIST OPENING OF THE NASAL PASSAGE BY THE VENTILATION │
│         MASK DISPOSED OVER THE NASAL PASSAGE        │
│                        1120                         │
│   ┌─────────────────────────────────────────────┐   │
│   │  INCREASE A CROSS-SECTIONAL AREA OF THE NASAL │   │
│   │                  PASSAGE                    │   │
│   │                    1122                     │   │
│   └─────────────────────────────────────────────┘   │
│                                                     │
│   ┌─────────────────────────────────────────────┐   │
│   │              ADJUST A BLADDER               │   │
│   │                    1124                     │   │
│   └─────────────────────────────────────────────┘   │
│                                                     │
│   ┌─────────────────────────────────────────────┐   │
│   │         ADJUST A PLURALITY OF BLADDERS      │   │
│   │                    1126                     │   │
│   └─────────────────────────────────────────────┘   │
└─────────────────────────────────────────────────────┘
```

```
┌─────────────────────────────────────────────────────────────┐
│ DISPOSE A CARBON-DIOXIDE COLLECTOR IN PROXIMITY TO, AND     │
│ OUTSIDE OF, A RESPIRATORY OPENING OF A PATIENT              │
│                          1610                               │
└─────────────────────────────────────────────────────────────┘
                              ↓
┌─────────────────────────────────────────────────────────────┐
│ COLLECT A SAMPLE OF EXHALED BREATH FROM THE PATIENT;        │
│ WHEREIN THE SAMPLE OF THE EXHALED BREATH FROM THE PATIENT IS│
│ SUBSTANTIALLY UNDILUTED BY RESPIRATORY GASES SUPPLIED FOR   │
│ THE PATIENT'S BREATHING                                     │
│                          1620                               │
└─────────────────────────────────────────────────────────────┘
                              ↓
┌─────────────────────────────────────────────────────────────┐
│ SENSE A LEVEL OF CARBON DIOXIDE IN THE EXHALED BREATH OF THE│
│ PATIENT WITH A CARBON-DIOXIDE SENSOR                        │
│                          1630                               │
└─────────────────────────────────────────────────────────────┘
                              ↓
┌─────────────────────────────────────────────────────────────┐
│ OUTPUT A SENSOR SIGNAL COMMENSURATE WITH THE LEVEL OF       │
│ CARBON DIOXIDE                                              │
│                          1640                               │
└─────────────────────────────────────────────────────────────┘
                              ↓
┌─────────────────────────────────────────────────────────────┐
│ CONVERT THE SENSOR SIGNAL INTO A MEASUREMENT OF CARBON      │
│ DIOXIDE CONTENT IN THE SAMPLE OF THE EXHALED BREATH FROM    │
│ THE PATIENT WITH A CARBON DIOXIDE ANALYZER                  │
│                          1650                               │
└─────────────────────────────────────────────────────────────┘
                              ↓
┌─────────────────────────────────────────────────────────────┐
│ APPLY A CARBON-DIOXIDE ANALYSIS PROTOCOL TO PROVIDE AN      │
│ ACCURATE MEASUREMENT OF CARBON DIOXIDE CONTENT IN THE       │
│ SAMPLE OF THE EXHALED BREATH FROM THE PATIENT THAT IS       │
│ SUBSTANTIALLY UNAFFECTED BY DILUTION FROM RESPIRATORY       │
│ GASES SUPPLIED FOR THE PATIENT'S BREATHING                  │
│                          1660                               │
└─────────────────────────────────────────────────────────────┘
```

```
┌─────────────────────────────────────────────────────────────────┐
│ PROVIDING A SIGNAL AT A FIRST END OF AN ELECTRICAL LEAD OF A    │
│                       BREATHING CIRCUIT                          │
│                            2502                                  │
└─────────────────────────────────────────────────────────────────┘
                              │
                              ▼
┌─────────────────────────────────────────────────────────────────┐
│ TRANSMITTING THE SIGNAL TO A SECOND END OF THE ELECTRICAL       │
│                 LEAD OF THE BREATHING CIRCUIT                    │
│                            2504                                  │
└─────────────────────────────────────────────────────────────────┘
                              │
                              ▼
┌─────────────────────────────────────────────────────────────────┐
│ RECEIVING THE SIGNAL AT THE SECOND END OF THE ELECTRICAL        │
│                 LEAD OF THE BREATHING CIRCUIT                    │
│                            2506                                  │
└─────────────────────────────────────────────────────────────────┘
                              │
                              ▼
┌─────────────────────────────────────────────────────────────────┐
│ DETERMINING HOW THE BREATHING CIRCUIT IS CONFIGURED BASED       │
│                         ON THE SIGNAL                            │
│                            2508                                  │
└─────────────────────────────────────────────────────────────────┘
```

FIG. 25

CARBON-DIOXIDE SAMPLING SYSTEM FOR ACCURATELY MONITORING CARBON DIOXIDE IN EXHALED BREATH

CROSS REFERENCE TO RELATED APPLICATIONS

This Application is related to U.S. patent application Ser. No. 13/105,738 entitled ADJUSTING A VENTILATION MASK, filed May 11, 2011.

This Application is related to U.S. patent application Ser. No. 13/105,757 entitled CORRUGATED FLEXIBLE SEAL OF A VENTILATION MASK, filed May 11, 2011.

This Application is related to U.S. patent application Ser. No. 13/105,773 entitled NASAL PASSAGE OPENER OF A VENTILATION MASK, filed May 11, 2011.

This Application is related to U.S. patent application Ser. No. 13/105,782 entitled A CARBON-DIOXIDE SAMPLING DEVICE FOR NONINVASIVELY MEASURING CARBON DIOXIDE IN EXHALED BREATH, filed May 11 2011.

This Application is related to U.S. patent application Ser. No. 13/105,793 entitled INTERCHANGEABLE INSERTS, filed May 11, 2011.

This Application is related to U.S. patent application Ser. No. 13/105.807 entitled LATERAL GAS LINE CONFIGURATION, filed May 11, 2011.

This Application is related to U.S. patent application Ser. No. 13/105,821 entitled QUICK DONNING HEADGEAR, filed May 11, 2011.

This Application is related to U.S. patent application Ser. No. 13/105,829 entitled SMART CONNECTIONS, filed May 11, 2011.

This Application is related to U.S. patent application Ser. No. 13/105,848 entitled TUBE PLACEMENT IN NON-INVASIVE VENTILATION, filed May 11 2011.

This Application is related to U.S. patent application Ser. No. 13/105,851 entitled NON-INVASIVE VENTILATION EXHAUST GAS VENTING, filed May 11, 2011.

This Application is related to U.S. patent application Ser. No. 13/105,861 entitled NON-INVASIVE VENTILATION FACIAL SKIN PROTECTION, filed May 11, 2011.

This Application is related to U.S. patent application Ser. No. 13/105,871 entitled NON-INVASIVE VENTILATION FACIAL SKIN PROTECTION, filed May 11, 2011.

BACKGROUND

Non-invasive ventilation involves the delivery of fresh respiratory gases to a patient through a non-invasive means such as a mask, hood, or helmet rather than through an invasive means such as an endotracheal tube inserted via an oral, nasal, or tracheal opening in a patient. Continuous positive airway pressure (CPAP) ventilation and bi-level ventilation are two specific techniques of non-invasive ventilation. CPAP ventilation, as implied by the name, provides a continuous pressure of air during ventilation which maintains the airway in an open state and thus can fill the lungs with air thus requiring less work from respiratory muscles. CPAP is often used for patients with respiratory failure or near respiratory failure and for individuals with sleep apnea. Bi-level or variable level ventilation is often used for sleep apnea patients and for non-invasive ventilation for respiratory insufficiency or failure in institutional and home setting and is similar to CPAP, except that pressure is varied during inspiration and expiration. For example, pressure is lowered during expiration to ease exhalation. Compared with invasive ventilation, non-invasive ventilation can result in lower patient stress levels and lower trauma to patient airways. As such, non-invasive ventilation techniques offer more patient comfort than invasive ventilation techniques.

There are three major components involved in non-invasive ventilation: a ventilator which is an item of hardware which supplies fresh respiratory gas(es); a patient interface such as a mask; and a breathing circuit (i.e., tubes and connectors) that couple the ventilator with mask such that the fresh respiratory gases can be supplied to the patient for breathing. There are generally two techniques of non-invasive ventilation that are commonly in use: single limb, and dual limb.

Single limb breathing circuit applications involve blowing high flow levels of fresh respiratory gas into the patient interface, and relying on vent ports in the patient interface for allowing exhaled respiratory gases to exit the patient interface into the atmosphere. Vent ports or vents are designated leakage points that allow for a controlled leakage, or venting, of fresh respiratory gases in order to maintain a desired pressure of respiratory gases within a patient interface and to clear exhaled carbon dioxide. "Single limb" refers to the fact that a ventilation limb or limbs coupled with a patient interface only supply fresh respiratory gas and do not provide a return path for exhaled gases. As such, in some "single limb" applications a fresh respiratory gas supply tube may split into two or more tubes/limbs that allow fresh respiratory gas to enter a patient interface via more than one location. Because of the presence and reliance on vents, single limb non-invasive ventilation is also referred to as vented non-invasive ventilation.

Dual limb breathing circuit applications involve respiratory gases being blown into a patient interface via a first limb and exhaust gases being evacuated from the patient interface via a second, separate limb. Because of the second limb which is used for evacuation of exhaust gases, no vents are needed in the patient interface for venting exhaust gases into the atmosphere. Because no vents are required, dual limb non-invasive ventilation is also referred to as non-vented non-invasive ventilation.

BRIEF DESCRIPTION OF THE DRAWINGS

The accompanying drawings, which are incorporated in and form a part of this application, illustrate embodiments of the subject matter, and together with the Description of Embodiments, serve to explain the principles of the embodiments of the subject matter. Unless noted, the drawings referred to in this brief description of drawings should be understood as not being drawn to scale.

FIG. 9 shows a method for adjusting a ventilation mask, in accordance to an embodiment.

FIG. 10 shows a method for adjusting a ventilation mask, in accordance to an embodiment.

FIG. 11 shows a method for assisting in opening a nasal passage, in accordance to an embodiment.

FIG. 16 shows a flowchart of a method for non-invasively measuring carbon dioxide in exhaled breath, in accordance with an embodiment.

FIG. 25 is a flow diagram of an exemplary method for determining configuration of a ventilation system in accordance with an embodiment.

DESCRIPTION OF EMBODIMENTS

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope. Furthermore, in the following description, numerous specific details are set forth in order to provide a thorough understanding of the subject matter. However, some embodiments may be practiced without these specific details. In other instances, well-known structures and components have not been described in detail as not to unnecessarily obscure aspects of the subject matter.

Overview of Discussion

Herein, various embodiments of a non-invasive ventilation patient interface, system, and components thereof are described. Various embodiments described herein can be utilized across the spectrum of non-invasive ventilation, from spontaneously breathing patients who need some respiratory assistance to patient who are unable to breathe without mechanical assistance. For purposes of the present description, it should be appreciated that many of the described patient interface embodiments may be utilized with both single limb and dual limb ventilation applications, and may in many cases be switched over from one to another by reconfiguring a ventilator and in some instances reconfiguring or replacing one or more components. Description begins with a general discussion of major components and features associated with the non-invasive ventilation technology described herein. This general discussion provides a framework of understanding for more particularized description which follows in thirteen separate sections. These thirteen sections are dedicated and focused on detailed discussion of particular features and concepts of operation associated with one or more embodiments of the described non-invasive ventilation technology.

Major Components and Features

Figure 1:
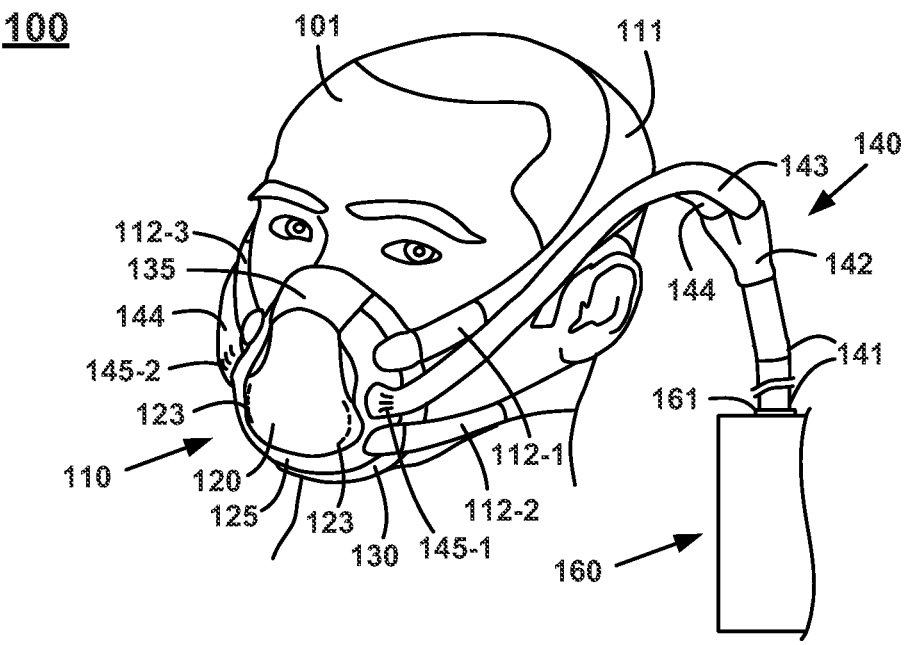
FIG. 1 shows a front perspective view of an example non-invasive ventilation system, in accordance with various embodiments.

FIG. 1 shows a front perspective view of an example non-invasive ventilation system 100, in accordance with various embodiments. Non-invasive ventilation system 100 comprises three major components, patient interface 110 (also referred to herein as mask 110), breathing circuit 140, and ventilator 160. Ventilator 160 supplies fresh breathable respiratory gas such as oxygen or other repertory gas(es). Breathing circuit 140 fluidly couples the fresh respiratory gas from ventilator 160 to patient interface 110. Patient interface 110 sealably couples in a controlled seal (controlled in the sense that intentional leaks are permitted while unintentional leaks are reduced or eliminated) over at least one respiratory opening of patient 101 to form a hollow chamber into which fresh respiratory gas is coupled via breathing circuit 140. Although patient interface 110 is illustrated in FIG. 1 and throughout as covering both the nasal and oral cavities (nose and mouth), some embodiments may cover only a nasal cavity or oral cavity, or may capture the entire face or head of a patient. Thus, in general, embodiments of patient interface 110 can be said to couple in a controlled seal over a respiratory opening of a patient, where a respiratory opening may include a nasal cavity, an oral opening, both the nasal and oral cavities of a patient, the entire face of a patient (encompassing the nasal and oral cavities), or the entire head of a patient (encompassing the nasal and oral cavities).

As illustrated, respiratory gas tube 141 and y-piece 142 provide a tubular path for fluidly coupling limbs 143 and 144 of patient interface 110 with ventilator 160. In some embodiments, y-piece 142 may include one or more swiveling portions to relieve torque and allow for articulation of breathing circuit 140. In some embodiments, limbs 143 and 144 may both be inhalation gas supply lines for supplying fresh respiratory gas for breathing by patient 101. In other embodiments, one of limbs 143 or 144 acts as an inhalation gas supply line, while the other of limbs 143 and 144 acts as an exhalation gas collection line for collecting exhaust gas (exhaled breath and unused respiratory gases) from patient 101. Although limb 143 is illustrated herein as a single tube, it is appreciated that, in some embodiments, limb 143 may be a plurality of smaller tubes. Such a configuration of limb 143 facilitates the plurality of smaller tube lying more or less flatly against and flexibly following the contour of the face of patient 101 or of a side strap of head strap system 111. Similarly, although limb 144 is illustrated herein as a single tube, it is appreciated that, in some embodiments, limb 144 may be a plurality of smaller tubes. Such a configuration of limb 144 facilitates a the plurality of smaller tubes lying more or less flatly against and flexibly following the contour of the face of patient 101 or of a side strap of head strap system 111.

In one embodiment, respiratory gas tube 141 fluidly couples with ventilator 160 via a respiratory gas port 161. Although not depicted in FIG. 1, in some embodiments, ventilator 160 may include a plurality of respiratory gas ports and/or other ports such as exhaled gas return port(s) and/or a carbon dioxide monitoring port. In some embodiments, respiratory gas port 161 and/or other connections and tubes in breathing circuit 140 may, among other things, self-identify to ventilator 160 whether patient interface 110 is a vented or non-vented patient interface and/or whether patient interface 110 is a neonatal, child, or adult patient interface. Furthermore, in some embodiments, connectors and ports of breathing circuit 140 are designed such at they only couple with compatible components. Thus, in one embodiment, neonatal connectors would only couple with a neonatal patient interface and a neonatal respiratory gas port 161. In one embodiment, child connectors would only couple with a child patient interface and a child respiratory gas port 161. In one embodiment, adult connectors would only couple with an adult patient interface and an adult respiratory gas port 161. These and other features of a "smart connection" protocol will be described further herein in a separate section below.

Anti-asphyxia valve(s) 145 (145-1, 145-2) are provided, in some embodiments, as a safety mechanism in case the flow of fresh respiratory gas fails or is interrupted. Anti-asphyxia valves 145 fail in an open position to the external atmosphere, so that the anti-asphyxia valve will open to the atmosphere to keep the patient from suffocating.

Patient interface 110 comprises a frame 125, a facial skin interface 130, a compliant nose bridge seal 135, a domed front portion 120 (which may be fixed or may be a removable/interchangeable insert), and a head strap system 111.

Head strap system 111 includes a plurality of side straps 112 (112-1, 112-2, and 112-3, 112-4 (not visible in FIG. 1, but illustrated in FIG. 7)) which couple with frame 125. Upper left side strap 112-1 and lower left side strap 112-2 couple head strap system 111 from a left lateral portion of frame 125 around the posterior skull of patient 101 and to upper right side strap 112-3 and lower right side strap 112-4. Upper right side strap 112-3 and lower right side strap 112-4 couple with a right lateral portion of frame 125. Side straps 112 are adjustable such that they may apply an adjustable securing force to secure nose bridge seal 135 and facial skin interface 130 of patient interface in position over one or more respiratory openings of patient 101. Adjustment of side straps 112 facilitates adjusting the fitment and seal of facial skin interface 130 to accommodate variety of patient facial sizes and shapes.

Side straps 112 couple with retention portions of frame 125, while limbs 143 and 144 swivelably couple with gas ports (also referred to as orifices) disposed as portions of frame 125. These retention portions and gas port connection features/orifices are be better illustrated and further discussed in conjunction with FIG. 7.

Facial skin interface 130 is coupled with nose bridge seal 135 and is disposed between frame 125 and the chin and cheek regions of patient 101. The general structure of facial skin interface 130 is such that there is a flexible material in contact with the face of patient 101, this allows for some movement of the patient while maintaining a seal with the face of patient 101 so that respiratory gases do not uncontrollably leak out from between facial skin interface 130 and the facial skin of patient 101. The flexible material may be silicone, Thermo Plastic Elastomer (TPE), two-layer or multi-layer plastic, a material of variable wall thickness, a combination of elastic and plastic materials, or other flexible material(s) that are known in the art. Herein flexible means that the material is capable of flexing to conform to a surface, such as a facial feature of a patient, in some embodiments, the flexible material is thinner at locations where it will contact the face of a patient and it gets more and more thick the further it gets from the patient contact area. This increasing thickness provides some increased rigidity and provides structure. Herein, "rigid" means that a material does not tend to flex to conform to a surface, such as a facial feature of a patient. While rigidity is desired in some portions of a patient interface, lack of flexibility in regions of a patient interface which come into contact with facial skin contributes to increased unintentional leakage and also creates pressure points which can skin necrosis in a relatively short period of time. Necrosis is the premature death of skin cells and can be caused by pressure point trauma and decreased blood circulation as a result of pressure applied to facial skin by a patient interface. As will be further described, in some embodiments facial skin interface 130 may incorporate one or more additional features to allow for increased flexibility (e.g., to allow some movement and articulation of facial skin interface 130) in order to alleviate pressure points and improve patient comfort while still maintaining fit such that patient ventilation is not disrupted by uncontrolled leakage of respiratory gases. Segmented sections, corrugations, ridges, bladders, and bellows are some examples of these additional features.

In general, the human nasal bridge has only a very thin layer of skin covering the nasal bone structures and flexible nasal cartilage. Because of this, the nasal bridge very susceptible to skin necrosis caused by pressure points. Additionally, portions of the nasal passages very easily pinch, crush, or slightly collapse in response to applied pressure. Compliant nose bridge seal 135 couples with left and right lateral portions of facial skin interface 130 and also couples between an upper portion of frame 125 and the nasal bridge of patient 101. Compliant nose bridge seal 135 is very flexible and, as such, complies with the shape of the nasal bridge of patient 101 in response to donning of patient interface 110. Although side straps 112 of head strap system 111 provide a securing force, the positioning of side straps 112 on frame 125 allow this securing force to be distributed via frame 125 to facial skin interface 130. In this manner, facial skin interface 130 mostly or entirely transfers the securing force to the chin and cheek bone/zygomatic arch regions of the face of patient 101, while little of none of the securing force is transferred to the nasal bridge of patient 101. Instead of relying on securing force of head strap system 111 to form a seal, compliant nose bridge seal 135 employs one or more other mechanisms such as corrugated sections, inflatable/inflated bladders, medical grade foam, and/or adhesive. In some embodiments, as will be described herein, when an adhesive, such as a hydro gel or pressure sensitive adhesive is utilized, nose bridge seal 135 may actually be configured to expand outward from the sides of the nose of patient 101 so as to impart a negative or outward force on the nasal bridge region of patient 101, while still performing a sealing function. Such an outward force will slightly open the nasal passageways of patient 101, rather than pinching them closed.

Domed front portion 120 is, in one embodiment, made of a transparent material which allows a medical care professional visibility of the oral and nasal cavities of patient 101. Domed front portion 120 is sealably coupled with frame 125 and, in conjunction with nose bridge seal 135, facial skin interface 130, and frame 125, forms a breathing chamber from which patient 101 may inhale fresh respiratory gas and into which patient 101 may exhale. In vented non-invasive ventilation, domed front portion 120 may include one or more exhaust gas vent ports 123 that allow expulsion of exhaust gas from patient interface 110 in response to exhalation of patient 101. In some embodiments, the size and arrangement of vent ports 123 is selected to allow fresh respiratory gases to escape at a predetermined flow rate in order to assist in controlling the pressure the fresh respiratory gases near a respiratory opening (nose, mouth, or nose and mouth) of patient 101.

As previously described, in some embodiments domed front portion 120 is a removably coupled portion of patient interface 110. In removably coupled embodiments, domed front portion 120 may be removed from patient interface 110 while the remainder of patient interface 110 remains in place on patient 101. Such removal of a removable coupled domed front portion 120 can be accomplished for a variety of reasons, including: to facilitate oral care of patient 101, to facilitate administration of oral or aerosolized medication to patient 101, to improve comfort of patient 101, to facilitate speech of patient 101, to clear debris (e.g., vomit, saliva, blood, etc.) from the airway or from within patient interface 110, and facilitate insertion and/or removal of oral or nasal tubes or medical instruments. As will be described, in some embodiments, one or more different features may be incorporated into a domed front portion 120. In some embodiments, a domed front portion 120 may be removed and interchangeably replaced with another domed front portion (which may offer a feature not included in the replaced domed front portion 120). A variety of different interchangeable versions of removable domed front portion 120 are illustrated and described herein. Removably coupled versions of domed front portion 120 may be referred to herein as "interchangeable patient interface inserts," "interchangeable functional inserts," "interchangeable inserts," "removable inserts," "inserts," or the like.

As is described herein, in some embodiments, a domed front portion 120 may have a function or support some medical function or procedure, and thus a domed front portion 120 may be changed out to change functions or to facilitate performing a variety of medical functions. It is further appreciated that, in some embodiments, domed front portions 120 may be configured to operated with a person of a certain size (e.g., a child, an adolescent, a grown person, an obese person, etc.). For example, vent holes disposed in a domed front portion 120 may be configured for a predetermined breathing rate/gas flow for a person of a particular size. In some embodiments, a domed front portion 120 can thus be inserted into patient interface 110 based upon the size of a patient 101 being ventilated.

Figure 2:
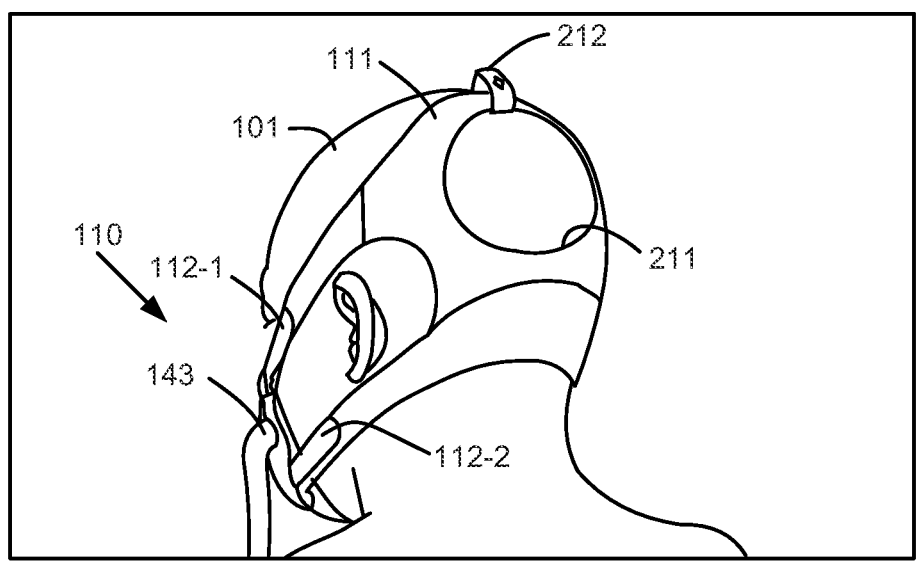
FIG. 2 is rear perspective of a patient interface of a non-invasive ventilation system, in accordance with various embodiments.

FIG. 2 is rear perspective of a patient interface 110 of a non-invasive ventilation system 100, in accordance with various embodiments. Limbs 143 and 144 (not visible) have been swiveled to a forward position and hang downward toward the chest of patient 101. As illustrated in FIG. 2, head strap system 111 defines a somewhat circular opening 211 (it maybe perfectly circular or may be somewhere between circular and oval in shape). It is appreciated that circular opening 211 may be devoid of material or may be covered by a fabric or other material. Moreover, circular opening 211 may be molded and/or may be defined by a plurality of slits made to open a region within head strap system 111. In some embodiments, head strap system 111 is constructed from semi-rigid material with an o-frame feature, defined by the coupling of side straps 112-1 and 112-3 to the upper left and right lateral portions of frame 125. This O-frame feature captures the top of the head while circular opening 211 cradles the occipital region of the rear skull of patient 101. The semi-rigid construction of head strap system 111 provides some amount of inherent rigidity so that when it is in storage, it can be collapsed or folded; but when it's removed from collapsed storage, it easily and naturally returns to a general head shaped structure, so that it is visibly obvious how to position and install head strap system 111 on patient 101 when donning patient interface 110. In this manner, there is no need to sort out where the front, back, top, or bottom is located. In one embodiment, patient interface 110 is packaged with head strap system 111 already pre-attached with frame 125, so that when unpackaged the semi-rigid structure of head strap system 111 causes it to look somewhat like a helmet that can just be pulled quickly over the head and face area of patient 101, much like putting on a catcher's mask.

Also depicted in FIG. 2 is a quick release rip cord type pull-tab 212. The positioning of the quick release pull tab 212 may be in different locations than illustrated and additional pull-tabs may be included in some embodiments. As illustrated, pull-tab 212 is located near the upper posterior skull and couples with head strap system 111. Pull-tab 212 is easy to access and grasp by both a patient and by a medical care professional. Pull-tab 212 provides a grasping point which assists it doffing patient interface 110 in an expeditious fashion in case of emergency or claustrophobia of patient 101.

Figure 3:
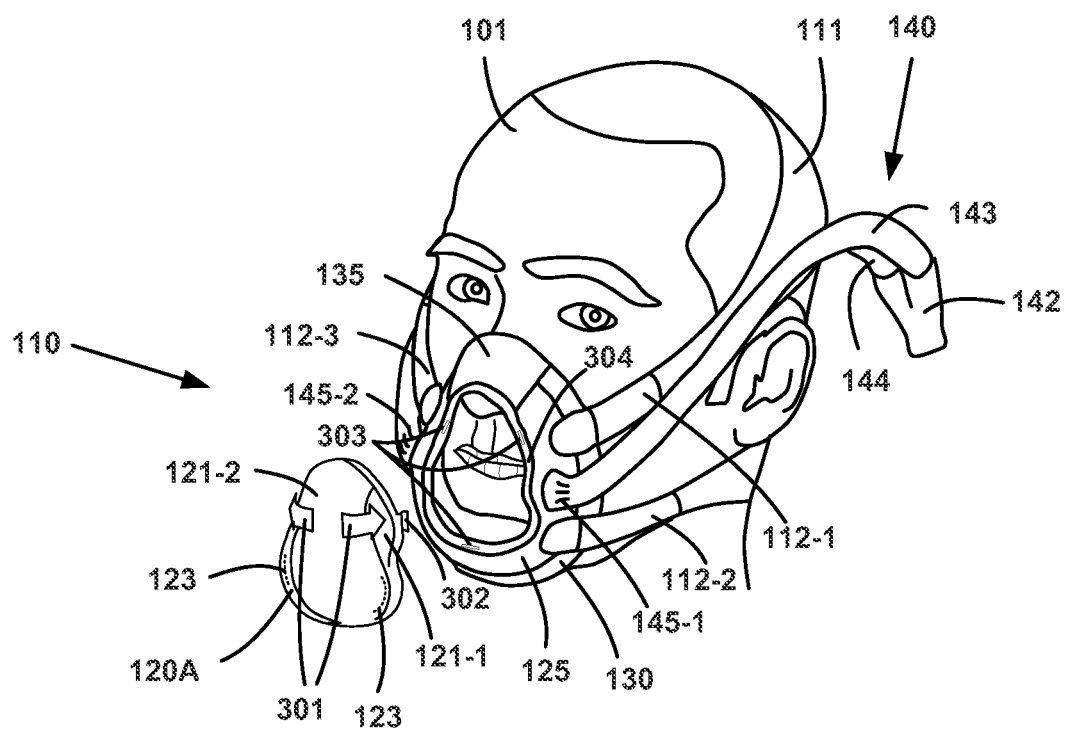
FIG. 3 shows a front perspective view of patient interface of a non-invasive ventilation system and illustrates a removal/insertion of an interchangeable patient interface insert, in accordance with an embodiment.

FIG. 3 shows a front perspective view of patient interface 110 of a non-invasive ventilation system 160 and illustrates removal/insertion of an interchangeable patient interface insert 120A, in accordance with an embodiment. As depicted, interchangeable patient interface insert 120A is in the removed position. Interchangeable patient interface insert 120A includes exhaust gas vent ports 123, and is thus designed for use in a vented non-invasive ventilation application. Interchangeable patient interface insert 120A includes one or more tabs 302 (one visible) which correspond with, and seat into, slots 303 that are disposed in the semi-elliptical rim 304 of frame 125. Be applying a pinching pressure on grip regions 121-1 and 121-2 (as illustrated by arrows 301), interchangeable patient interface insert 120A can be compressed slightly so that tabs 302 can be seated into slots 303 and interchangeable patient interface insert 120A can be removably coupled with frame 125. Reversal of the installation process allows for the removal of interchangeable patient interface insert 120A.

Figure 4:
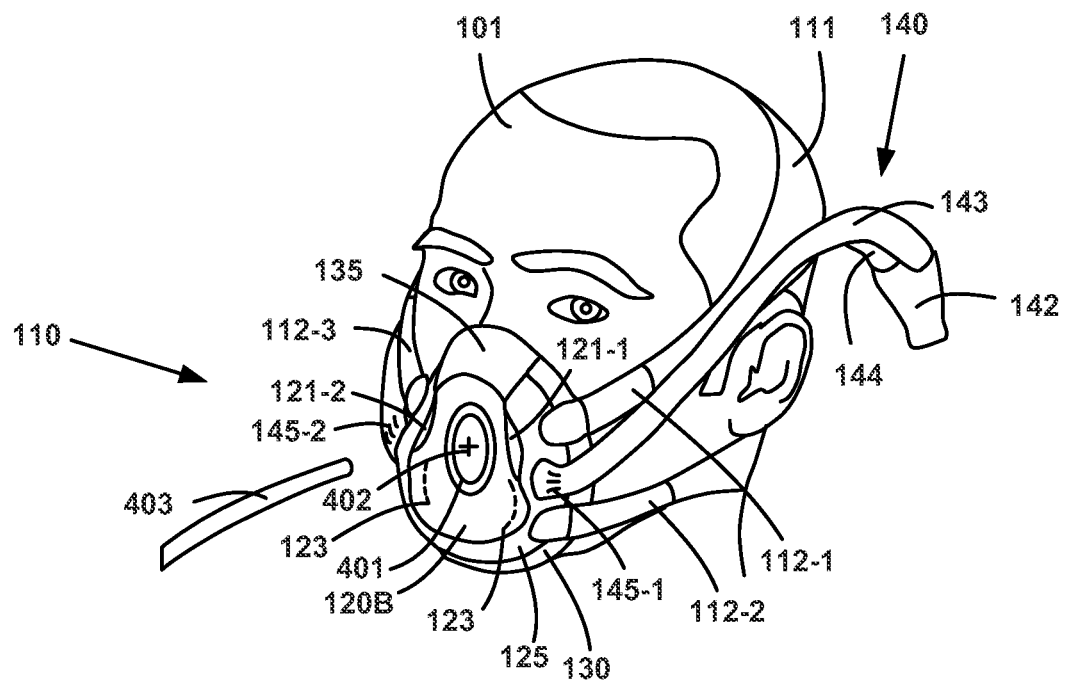
FIG. 4 shows a front perspective view of patient interface of a non-invasive ventilation system and illustrates an interchangeable patient interface insert which includes a self-sealing access port, in accordance with an embodiment.

FIG. 4 shows a front perspective view of patient interface 110 of a non-invasive ventilation system 100 and illustrates an interchangeable patient interface insert 120B which includes a self-sealing access port 401, in accordance with an embodiment. Self-sealing access port 401 may have one or more slits or openings through which a tube, such as tube 403 may be sealably inserted through interchangeable patient interface insert 120B. As depicted in FIG. 4, self-sealing access port 401 comprises one or more slits 402. In some embodiments, as depicted, slits 402 may intersect at right angles in the shape of a plus sign. Self-sealing access port 401 provides an opening through which a medical professional can perform procedures such as a bronchoscopy, as it gives access for a bronchoscope or other tubing or medical devices/instruments which may be inserted into the oral or nasal cavities of the patient. This allows for insertion of tubes/devices/instruments and performance of some medical procedures without removing patient interface 110. Instead of doffing patient interface 110 to insert a tube or perform a procedure, interchangeable patient interface insert 120B can be installed (if not already installed) and the procedure can be conducted/tubing inserted through interchangeable patient interface insert 120B. This allows insertion of some tubing and performance of some medical procedures, which involve oral or nasal passages, while still performing noninvasive ventilation. For example, interchangeable patient interface insert 120B allows for bronchoscopy to be performed on a sicker ventilated patient, which such a procedure could not otherwise be performed on, without removing the ventilation. Additionally, tube 403 or other device/instrument can be left in place within self-sealing access port 401. In some embodiments, self-sealing access port 401 is sized, shaped, and configured such that it can couple with a nebulizer, metered dose inhaler, or other therapeutic device or drug delivery device, so that that flow from the attached device is directed towards a mouth and/or nose of patient 101.

Figure 5:
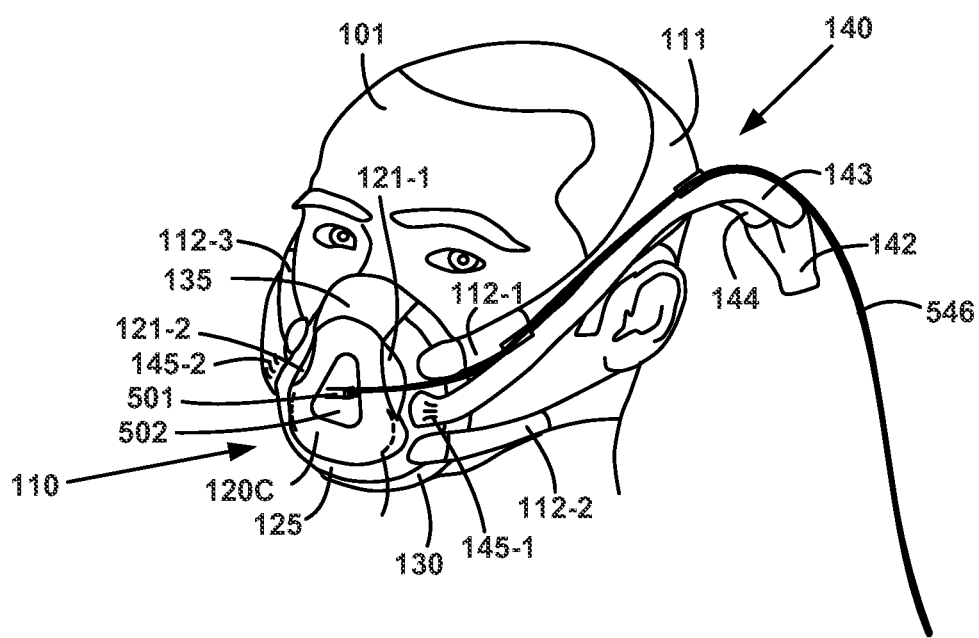
FIG. 5 shows a front perspective view of patient interface of a non-invasive ventilation system and illustrates an interchangeable patient interface insert which includes a breath sampling port, in accordance with an embodiment.

FIG. 5 shows a front perspective view of patient interface 110 of a non-invasive ventilation system 100 and illustrates an interchangeable patient interface insert 120C which includes a breath sampling port 501, in accordance with an embodiment. As illustrated, interchangeable patient interface insert 120C does not include the exhaust gas vent ports that were included on interchangeable patient interface insert 120A and interchangeable patient interface insert 120B. In one embodiment, this can be because exhaust gas vent ports are disposed elsewhere in patient interface 110. In another embodiment, this is because interchangeable patient interface insert 120C is designed for use with non-vented non-invasive ventilation in which fresh respiratory gas for inhalation is supplied by one limb (e.g., limb 143) and exhaust gas (exhaled breath and unused respiratory gases) is expelled from patient interface and collected via another limb (e.g., limb 144). Interchangeable patient interface insert 120C includes a breath sampling port 501 to which a breath sampling line 546 may be coupled in order to capture a sample of exhaled breath from within patient interface 110. Breath sampling line 546 may then couple a captured exhaled breath sample to a carbon dioxide analyzer or other analyzer.

In one embodiment, a slight concavity is defined on the interior portion of interchangeable patient interface insert 120C to form a breath scoop 502. Breath scoop 502 is designed so that it is positioned in a region roughly centered on the upper lip of patient 101 so that it can briefly capture exhaled breath in a location where it can not be quickly washed away by a cross-flow between limbs 143 and 144. In other embodiments, instead of being a simple concavity defined on the interior side of interchangeable patient interface insert 120C, breath scoop 502 may be a separate structure, coupled in approximately the same location on the interior side of interchangeable patient interface insert 120C. In embodiments which include breath scoop 502, breath sampling port 501 sealably couples breath sampling line 546 with breath scoop 502. Breath sampling line 546 operates to couple a captured exhaled breath sample to a carbon dioxide analyzer or other analyzer. Techniques for conducting breath sampling will be discussed further in a separate section herein.

Figure 6:
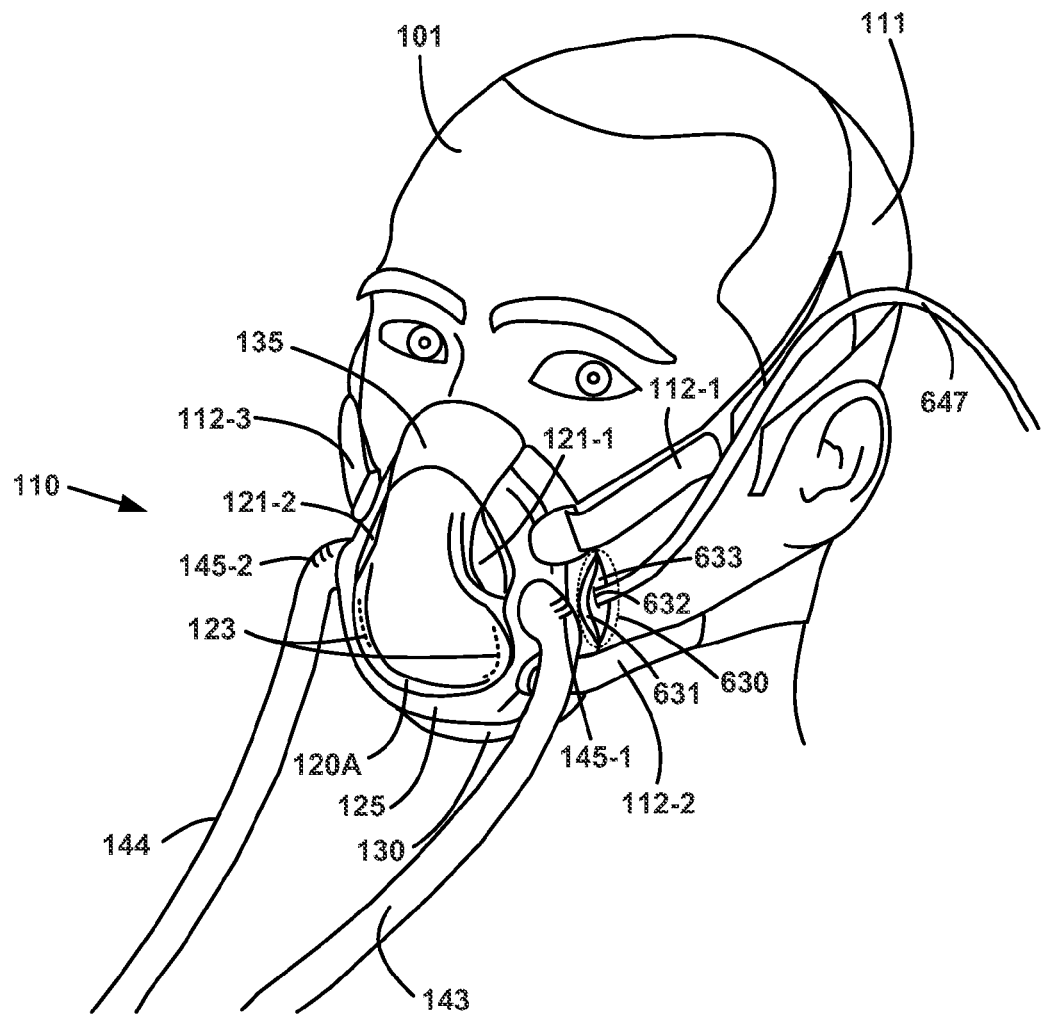
FIG. 6 shows a front perspective view of patient interface of a non-invasive ventilation system and illustrates a self-sealing gastric tube insertion region disposed within the facial skin interface, in accordance with an embodiment.

FIG. 6 shows a front perspective view of patient interface 110 of a non-invasive ventilation system 100 and illustrates a self-sealing gastric tube insertion region 630 disposed within or coupled with facial skin interface 130, in accordance with an embodiment. In FIG. 6, limbs 143 and 144 are shown swiveled downward such that that drape down toward the chest of patient 101. This swiveling allows for the fresh respiratory gas to be provided from the front side of patient 101 instead of from the rear/overhead of patient 101. This provides an option for patient comfort.

As depicted in FIG. 6, a gastric tube 647 has been inserted through a self-sealing an opening 632 defined in gastric tube insertion region 630, near the left cheek of patient 101. Gastric tube 647 may be a venting tube, feeding tube, or the like, and may be orogastric or nasogastric. A breath sampling tube or other tube may be inserted in a similar manner to that of tube 647. In one embodiment, where facial skin interface 130 includes a plurality of flexible bladder sections or corrugations, insertion region 630 may be a gap between two of the flexible bladders or corrugations which provides an opening 632 for insertion of tube 647. Herein, a corrugation is a series of convolutions that define peaks and valleys in the sealing material, and which can flexibly expand and contract by expanding and contracting the corrugations. Air pressure supplied by ventilator 160 may inflate the bladders and cause them to seal about tube 647 inserted in a gap that exists between the bladders. The bladders then transfer the securing force (provided from head strap system 111 to frame 125) around the inserted tube 647 such that the tube is not driven into the facial skin of patient 101 to create a pressure point. In another embodiment, as depicted, patient interface 110, includes an arched portion/bridge 631, which provides a rigid or semi-rigid structure to shield tube 647 and opening 632 from the restraining forces which are normally transferred to facial skin interface 130 from head strap system 111, and then from facial skin interface 130 to the facial skin of patient 101. This prevents this restraining force from causing a pressure point by compressing tube 647 into the skin of patient 101. In one embodiment, a cushioning material 633, such as foam, silicone, or TPE surrounds opening 632 and provides a sealing function for self-sealing about tube 647 when inserted in opening 632, sealing opening 632 when tube 647 is not inserted in opening 632, and sealing to the facial skin of patient 101.

In one embodiment, all or part of insertion region 630, opening 632, cushioning material 633, and/or bridge 631 is/are configured to breakaway facial skin interface 130. That is, one or more of these portions may be removably coupled with facial skin interface 130. By constructing one or more of portions 631, 632, and/or 633 such that they may be broken away from the rest of patient interface 110, the remainder of patient interface 110 can be removed/doffed from patient 101 without removing tube 647 from patient 101 as would typically be required if tube 647 was inserted through some other opening in a conventional mask/patient interface. In a similar, when tube insertion region 630 is a gap between a pair of bladders or corrugations, tube 647 can be slipped from between the gap and can remain inserted in patient 101 while patient interface 110 is removed/doffed.

Figure 7:
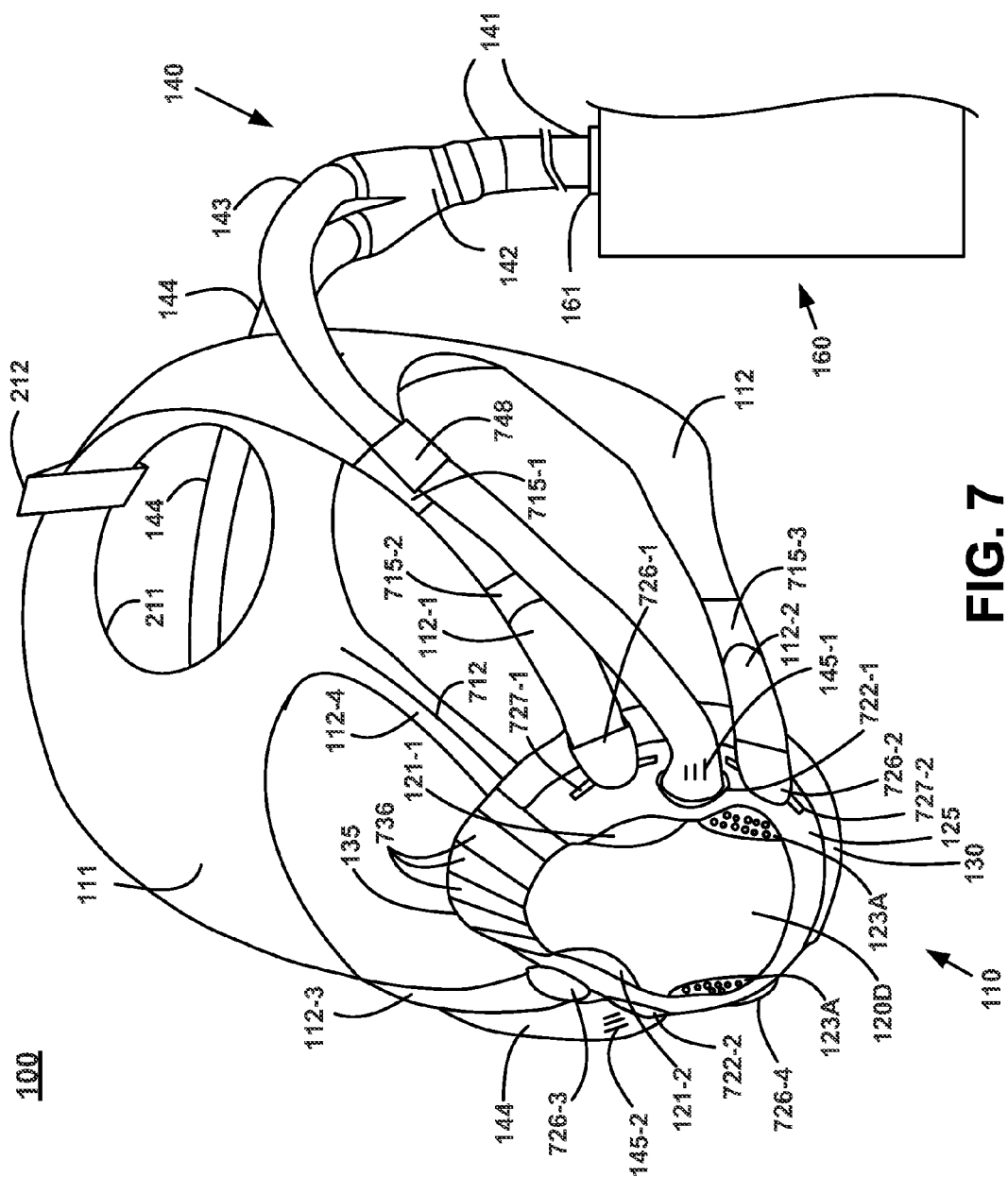
FIG. 7 shows a front perspective view of a doffed patient interface of a non-invasive ventilation system, in accordance with an embodiment, and also illustrates an interchangeable patient interface insert which includes built-in filter media, in accordance with an embodiment.

FIG. 7 shows a front perspective view of a doffed patient interface 110 of a non-invasive ventilation system 100, in accordance with an embodiment, and also illustrates an interchangeable patient interface insert 120D which includes built-in filter media 123A, in accordance with an embodiment. FIG. 7 illustrates the manner in which the semi-rigid structure of head strap system 111 retains the general shape of a helmet, even in a doffed con figuration.

In one embodiment, filter media 123A can be used in conjunction with or in place or exhaust gas vent ports 123 which have been depicted elsewhere herein. Typically, exhaust gas vent ports 123 are open to the atmosphere. This allows blowout of exhaled gases into the atmosphere, which may be undesirable or even dangerous to a care giver in some patient care circumstances. Instead of open vent holes, in one embodiment, filter media 123A is included or alternatively utilized. Filter media 123A provides a controlled pressure drop in addition to filtering contagions from exhaled gases as the exhaled gases pass through. In some embodiments, the filter media 123A can simultaneously filter and vent, thus eliminating the need have separate vent holes. Media such as, but not limited to, filter cloth (e.g., cotton, polyester, or bamboo) or open cell foam may be utilized to form filter media 123A. A variety of factors including one or more of composition, thickness, surface area, and porosity of the media of filter media 123A can be selected, in some embodiments, to both filter contagions and provide a designated and intentional flow/leak rate to control internal pressure of patient interface 110. In one embodiment, interchangeable patient interface insert 120D can be removed and replaced with a new interchangeable patient interface insert 120D when filter media 123A becomes clogged, soiled, or has surpassed its recommended replacement interval. In another embodiment, filter media 123A is, itself, replaceable.

In the enlarged view afforded by FIG. 7, a plurality of bladders 736 are visible which are disposed in compliant nose bridge seal 135. Bladders 736 may be filled with air, gas, or liquid upon manufacture of patient interface 110, in one embodiment. In another embodiment, fresh respiratory gas flow may be utilized (selectively in some embodiments), to inflate bladders 736. Although not illustrated in FIG. 7, in some embodiments, such bladders are also disposed around selected portions or the entirety of the periphery of facial skin interface 130.

FIG. 7 also illustrates, fasteners 726 (726-1, 726-2, 726-3, 726-4) to which side straps 112 (112-1, 112-2, 112-3, 112-4) may be buckled or otherwise fastened. In some embodiments, fasteners 726 are permanently coupled or removably coupled (i.e., snapped) into positioning tracks 727 (727-1, 727-2) along which the position of a fastener 726 may be adjusted. When snap type fasteners 726 are utilized, unsnapping one or more fasteners 726 provides a means for quick disconnect of side straps 112, which allows patient interface 110 to quickly doffed. Slide adjustment allows for the positioning of fasteners 726 and helps adjust fasteners 726 to divert securing force way from compliant nose bridge seal 135 and the bridge of the nose of patient 101. Additionally, positioning tracks 727 allow adjustment of the pitch and of patient interface 110 with respect to the face of patient 101.

In some embodiments hook and loop or similar type of fastening may be utilized to secure a side strap 112 or other component. For example, regions 715 (715-1, 715-2, 715-3) illustrate regions where either hook material or loop material may be disposed such that it may be mated with its complimentary hook/loop component disposed on the end portion of a side strap 112 or on a positioning sleeve 748 associated with a tube or other component. When hook and loop type (or similar) fastening is utilized to secure ends of side straps 112, a means for quickly doffing patient interface is provided by undoing the hook and loop fastening.

In some embodiments, a side strap 112 may change colors or change from opaque to somewhat translucent, transparent in response to a level of force induced stress on the strap which is indicative of a level of force or strap tightening that is considered to be so tight as to cause necrosis if not loosened. For example, an opaque side strap 112 of any color may stretch slightly and become translucent or transparent enough that a color change is noticeable in response to the stress of the side strap being stretched into an over tight state. Similarly, in some embodiments, an opaque side strap 112 of any color may stretch slightly and become translucent or transparent enough that that an embedded colored thread (e.g., a red thread) becomes visibly exposed in response to the stress of the side strap being stretched into an over tight state. An example of such an embedded colored thread 712 is shown FIG. 7 as being visible on the rear (patient facing) side of side strap 112-4 at all times. In various embodiments, embedded thread 712 would only become visibly exposed on the opposite, non-patient facing side of side strap 712-4 in response to over tightening of side strap 112-4. It is appreciated that some or all of side straps 112 may include such a color changing and/or embedded thread feature to indicate over tightened conditions. In some embodiments, embedded thread 712 may be embedded such that it is not visible at all, even on the non-patient facing side of a side strap 712, until the side strap 712 becomes stretched into an over tightened state.

Orifices 722 (722-1, 722-2) are openings disposed, in one embodiment, in frame 125. Limb 143 is illustrated as being sealably coupled with respiratory gas delivery orifice 722-1 which provides an entry port for fresh respiratory gas from ventilator 160. Similarly, limb 144 is illustrated as being sealably coupled with respiratory gas delivery orifice 722-2 which provides a second entry port for fresh respiratory gas from ventilator 160 in a vented configuration. In a non-vented configuration, limb 143 or 144 may be used to transport exhaust gases away from patient interface 110. In such a non-vented embodiment, orifice 722-2 may then comprise an exhaust gas orifice.

Figure 8A:
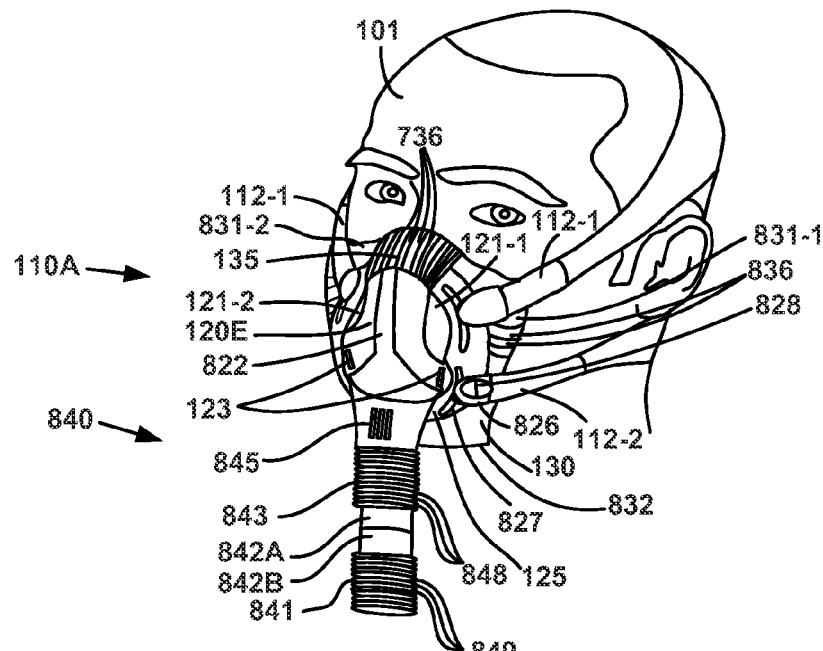
FIGS. 8A and 8B shows front perspective views of patient interfaces of a non-invasive ventilation system which are configured with a zygomatic facial interface and illustrate interchangeable patient interface inserts which include an aviator style fresh respiratory gas interface, in accordance with various embodiments.

FIG. 8A shows a front perspective view of a patient interface 110A of a non-invasive ventilation system 100 configured with a zygomatic facial interface 831 and illustrating an interchangeable patient interface insert 120E which includes an aviator style fresh respiratory gas interface 822, in accordance with an embodiment. By aviator style, what is meant is that the fresh respiratory gases enter the patient interface at approximately a midline position on the front of the patient interface rather than from one or both lateral sides of the patient interface.

In FIG. 8A, an alternative, aviator style, vented non-invasive ventilation breathing circuit 840 is illustrated. Breathing circuit 840, in some embodiments, comprises respiratory gas supply tube 841, swivel connector pieces 842A and 842B, limb 843, anti-asphyxia valve 845, and aviator style fresh respiratory gas interface 822. Anti-asphyxia valve 845 operates in the same manner as the previously described anti-asphyxia valve 745. Interchangeable patient interface insert 120E is removable/replaceable by compressing grip regions 121-1 and 121-2 toward one another. In one embodiment, interchangeable patient interface insert 120E, anti-asphyxia valve 845, limb 843, and swivel connector piece 843A are coupled together and supplied as a single removable/replaceable unit. Limb 843 couples with respiratory gas supply tube 841 via a torque relieving swivel coupling provided by swivel connector pieces 842A and 842B which form an omni-directional swivel to relieve torque and prevent kinking and twisting of breathing circuit 840. Respiratory gas supply tube 841 couples with ventilator 160 (not visible in FIG. 8A) in a similar manner as previously described for respiratory gas tube 141. In one embodiment, gas supply tube 841 may similarly utilize a "smart connection" to ventilator 160. Ribs 848 configured into limb 843 and/or ribs 849 configured into gas supply line 841 provide for torque relief and flexibility, which facilitate patient comfort and ease of movement while patient interface 110A is donned. In some embodiments, swivel portions 842A and 842B may be omitted and gas supply tube 841 and limb 843 may be a continuous piece of flexible tubing.

The zygomatic arch is a bony structure, but it also typically has a thicker layer of fatty tissue than the bridge of the nose, which is generally thin-skinned and has little in the way of cushioning. Because of the thin-skin on the bridge of the nose pressure points on the bridge of the nose quickly disrupt blood flow and create necrosis. Zygomatic facial interface 831 provides wing like extensions (831-1 and 831-2) of facial skin interface 130 which transfer securing forces of patient interface 110 to the zygomatic arch areas (cheek bones) of patient 101 and also spread the securing forces over a larger surface area of facial skin that other facial skin interfaces illustrated herein. By spreading securing forces to the zygomatic arch, over a larger facial skin surface area, and away from the bridge of the nose, zygomatic facial interface 831 further reduces the securing force (if any) which is transferred to nose bridge seal 135. Zygomatic facial interface 831 spreads securing forces over a larger surface area of facial skin, and onto zygomatic arch structure. In one embodiment, either or both of facial skin interface 130 and zygomatic facial interface 831 may incorporate a plurality of structural features such as corrugations, ridges, or bladders 836. One of the major differences between a corrugation/ridge and a bladder is internal, as a bladder may be adjustably filled with a gas or fluid, while a corrugation/ridge cannot. Even though designed to be inflatable filled, a bladder may still have a bumpy exterior appearance which makes it look similar to and in some respects function similar to a corrugation/ridge. In one embodiment, bladders 836 are similar in structure and function to bladders 736 and provide cushioning and allow for some flexibility and movement of patient interface 110A while still maintaining an intact facial seal with patient 101.

In one embodiment, patient interface 110A also includes an extended chin portion 832. Oral-nasal masks are intended to capture both the mouth and nose. Extended chin portion 832 helps keep the patient's mouth closed in an oral mask or an oral-nasal mask. This can increase patient comfort. In one embodiment, extended chin portion 832 may include a bellows feature (not visible) that expands/contracts in response to movement of the chin of patient 101. This allows patient 101 to slightly open his/her mouth or extend his/her chin without compromising the seal of patient interface 110A and allowing respiratory gas to uncontrollably leak.

In FIG. 8A, side straps such as 112-2 couple with fasteners such as fastener 826. As depicted, fastener 826 is permanently or removably coupled into a track 827 along which it may be positioned. Slide-to-release mechanism 828 is utilized to lock fastener 826 in a desired position within track 827 or to unlock fastener 826 so that it may be slidably positioned in track 827. It is noted that in FIGS. 7 and 8, strap positioning features are located near the face of patient 101 so that they are easily accessible for adjustment by patient 101 or by a care giver.

Although zygomatic facial interface 831, extended chin portion 832, slide-to release-mechanism 828, and interchangeable patient interface insert 120E are illustrated together in FIG. 8A, these features may be utilized separately. For example, zygomatic facial interface 831 can be incorporated into patient interface 110 which is illustrated in FIGS. 1-7. Similarly, an aviator style fresh respiratory gas interface 822 may be utilized in patient interface 110A which does not include zygomatic facial interface 831.

Figure 8B:
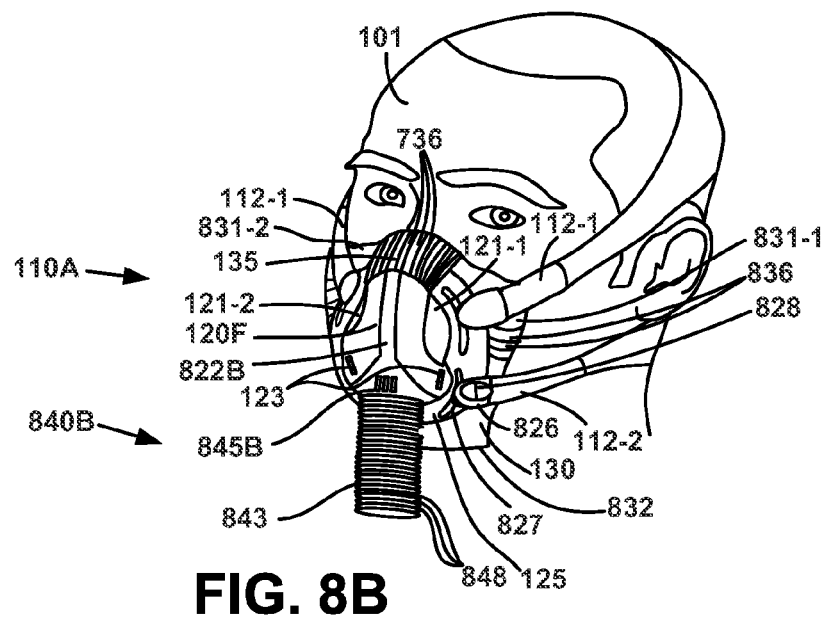

FIG. 8B is an aviator style patient interface similar to FIG. 8A in all regards (wherein like numerals refer to like components) except that an interchangeable patient interface insert 120F with an aviator style fresh respiratory gas interface 822B has replaced interchangeable patient interface insert 120E and aviator style fresh respiratory gas interface 822. As can be seen patient interface 120F includes anti-asphyxia valve 845B. As illustrated in FIG. 8B, aviator style fresh respiratory gas interface 822 utilizes an alternative breathing circuit 840B which comprises a ribbed respiratory gas supply tube 841 that connects directly gas interface 822B without the use of an elbow, and which, in some embodiments, does not include a swivel connector piece.

Section 1: Adjusting a Ventilation Mask

Mask 110 includes a sealing portion (e.g., compliant nose bridge seal 135 and/or facial skin interface 130). In various embodiments, the sealing portion includes bladders, as described above. For example, compliant nose bridge seal 135 includes bladders 736 and facial skin interface 130 includes bladders 836. In one embodiment, bladders 736 extend substantially along the entire length of compliant nose bridge seal 135. Similarly, in another embodiment, bladders 836 extend substantially along the entire length of facial skin interface 130.

In various embodiments, mask 110 is adjusted by fluidly adjusting the bladders (e.g., bladders 736 and 836). In particular, mask 110 is adjusted by inflating the bladders by gas, air, or liquid or any combination thereof. Also, mask 110 is adjusted by deflating the bladders.

In one embodiment, the bladders are fluidly connected to ventilator 160. For example, each bladder is fluidly connected to ventilator 160 via a tube. The tube may be similar to line 546 or tube 647. In such an embodiment, each bladder is fluidly separate from one another and each bladder is fluidly connected to ventilator 160.

Alternatively, two or more bladders (e.g., adjacent bladders or non-adjacent bladders) may be fluidly connected to one another. As such, the fluidly connected bladders are fluidly separate from other bladders or other fluidly connected bladders.

In another embodiment, the bladders are fluidly connected to an inflation source. Such as, but not limited to, a pressure tank.

Mask 110 may be adjusted for a variety of reasons. For example, mask 110 may be adjusted in response to a detected unintentional leak.

FIG. 9 depicts an embodiment of a method 900 for adjusting a ventilation mask.

At 910 of method 900, a ventilative state of mask 110 is measured. It is understood that mask 110 is placed over a nose and/or mouth of a patient, wherein a sealing portion of mask 110 is for establishing a fluid seal between mask 110 and the patient, and wherein the sealing portion comprises a plurality of bladders.

It is also understood that "ventilative state," used herein, is any state of system 100 that is measurable and facilitates in determining whether or not there is an unintentional leak between mask 110 and patient 101. For example, a ventilative state can be, but is not limited to, pressure, airflow, etc.

In one embodiment, at 912, airflow is measured. In another embodiment, at 914, pressure is measured.

In various examples, ventilative states (e.g., airflow, pressure) of non-invasive ventilation system 100 are measured. The ventilative states can be measured by ventilator 160 or other measuring devices.

The measuring can occur by obtaining information of ventilative states at various locations within system 100. For example, ventilative states can be measured at mask 110, at breathing circuit 140 and/or ventilator 160.

At 920, an unintentional leak of the fluid seal is determined based on a measured change of the ventilative state. For example, if the measured pressure and/or airflow in system 100 falls outside of a prescribed or expected range, then it is determined that there is an unintentional leak of the fluid seal. An unintentional leak between mask 110 and patient 101 may occur due to a variety of reasons (e.g., patient may accidentally bump mask 110, patient 101 may move mask 110, etc.). As a result, a ventilative state of system 100 may change.

At 930, a bladder is adjusted to seal the unintentional leak. For example, at least one bladder (e.g., at least one of bladders 736 or 836) is adjusted. In particular, if there is a gap (e.g., unintentional leak) between a bladder and patient 101, then the bladder can be adjusted (e.g., inflated) to seal the gap.

In one embodiment, at 931, a bladder is automatically adjusted to seal the unintentional leak. For instance, in response to measured change in the ventilative state (e.g., lower pressure) which is indicative of an unintentional leak between mask 110 and patient 101, a bladder is automatically inflated (e.g., by ventilator 160) to facilitate in sealing the unintentional leak. Alternatively, a bladder is manually adjusted.

In another embodiment, at 932, bladders are sequentially adjusted. For example, in response to a measured change in the ventilative state outside an expected or prescribed range, a first bladder is inflated. If the ventilative state still remains outside and expected or prescribed range, another bladder is inflated, such as an adjacent bladder to the first bladder, and so on, until the ventilate state returns to the expected range and thus the unintentional leak is sealed. Alternatively, a bladder inflated subsequent the first inflated bladder, is not adjacent to the first bladder.

In a further embodiment, at 933, bladders are automatically adjusted according to a pre-defined pattern. For example, the inflation of bladders can initiate at an arbitrary first bladder and continue clockwise or counterclockwise from the first bladder, until the unintentional leak is sealed. In another example, a first bladder, located at a position with a highest probability of unintentional leakage, is initially automatically adjusted. A second bladder, located at a position with a second highest probability of unintentional leakage, is subsequently adjusted, and so on, until the unintentional leak is sealed.

In another embodiment, at 934, a bladder is adjusted such that a measured ventilative state returns to a prescribed ventilative state. For example, in response to a ventilative state falling out of a prescribed or expected range, a bladder is adjusted to stop the unintentional leak. As a result of adjusting the bladder, the ventilative state returns to a prescribed ventilative state in a prescribed ventilative state range which is indicative of a proper seal between mask 110 and patient 101.

In one embodiment, at 935, more than one bladder is simultaneously adjusted. For example, all of the bladders disposed in compliant nose bridge seal 135 are simultaneously adjusted. In another embodiment, all of the bladders disposed on pressure points of patient 101 are simultaneously adjusted.

Moreover, mask 110 may be adjusted to decrease necrosis.

FIG. 10 depicts an embodiment of a method 1000 for adjusting a ventilation mask to decrease necrosis.

At 1010 of method 1000, mask 110 is fluidly sealed to a patient 101, wherein the mask comprises a plurality of bladders (e.g., bladders 736 and 836) in physical contact with the patient.

At 1020, a bladder is adjusted to decrease necrosis. For example, a bladder(s) is adjusted to decrease pressure at a pressure point. It should be appreciated that a bladder(s) can be adjusted to decrease necrosis similarly to bladders being adjusted as described in method 900.

In one embodiment, at 1022, a bladder is adjusted (e.g., deflated) to decrease pressure on a pressure point of the patient.

In another embodiment, at 1024, inflate a bladder of the plurality of bladders to decrease necrosis. For example, bladders surrounding a pressure point are inflated to decrease necrosis.

In a further embodiment, at 1026, a bladder is deflated to decrease necrosis. For example, a bladder disposed on a pressure point is deflated to decrease necrosis.

In one embodiment, at 1028, a bladder(s) is automatically adjusted to decrease necrosis. For example, after a predetermined amount of time, a bladder(s) located on or about a pressure point are automatically adjusted to decrease necrosis.

Section 2: Corrugated Flexible Seal of a Ventilation Mask

Mask 110 includes a sealing portion (e.g., compliant nose bridge seal 135 and/or facial skin interface 130). In various embodiments, the sealing portion is a corrugated flexible seal. For example, the sealing portion includes bladders 736 and 836 (also referred to as corrugations or ridges). The ridges are disposed along the corrugated flexible seal and configured for physical contact with patient 101.

In general, the corrugated flexible seal (in particular, the ridges of the corrugated flexible seal) allows for some flexibility and movement of patient interface 110 while still maintaining an intact facial seal with patient 101.

In one embodiment, corrugated flexible seal is configured to establish a fluid seal over the nose of patient 101. For example, a fluid seal occurs between ridges 736 of compliant nose bridge seal 135 and the nose bridge of patient 101 (see FIG. 7). With respect to ridges 736, their length, depth, and width (frequency) may vary in some portions of the compliant nose bridge.

In another embodiment, the corrugated flexible seal is configured to establish a fluid seal around the nose and/or mouth of patient 101. For example, a fluid seal occurs around the nose and/or mouth of patient 101 by ridges 736 of compliant nose bridge seal 135 and ridges 836 of facial skin interface 130.

Corrugated flexible seal (in particular, ridges 736 and/or ridges 836) is configured to move or flex in a plurality of axes and/or directions. This allows for flexibility and movement of patient interface 110 while still maintaining an intact facial seal.

Ridges 736, as depicted in FIG. 7, extend along the width of compliant nose bridge seal 135. In other words, the length of each ridge extends in a direction from the tip of the nose towards the eyes of patient 101. Moreover, ridges 736 are disposed along the length of nose bridge seal 135.

Ridges 836, as depicted in FIG. 8, extend along the width of facial skin interface 130. Moreover, ridges 836 are disposed along the length of facial skin interface 130 (and zygomatic facial interface 831). With respect to ridges 836, their length, depth, and width (frequency) may vary in some portions of facial skin interface 130 and or zygomatic facial skin interface 831. Also, in some embodiments, the length of ridges 736 is longer than the length of ridges 836.

In various embodiments, the ridges of the corrugated flexible seal have different shapes. For example, ridges 836 can have different shapes from one another and/or have different shapes than ridges 736. Elsewhere herein, microgrooves are described. It should be appreciated that ridges and valleys of corrugations are much larger in depth and width than microgrooves. For example, in some embodiments corrugations are at least an order of magnitude larger than microgrooves. It is appreciated that one or more microgrooves may be configured into a corrugation, in some embodiments.

Section 3: Nasal Passage Opener of a Ventilation Mask

In various embodiments, mask 110 includes a nasal passage opener. The nasal passage opener is configured for facilitating in opening of a nasal passage (or nasal valve). The nasal passage opener is disposed over a nasal passage (or nasal valve) of patient 101 when mask 110 is sealed on the face of patient 101. Opening up the nasal passages (valves) can assist in decreasing the rate of breathing and/or patient effort in breathing.

In one embodiment, the nasal passage opener is compliant nose bridge seal 135. For example, when compliant nose bridge seal 135 is placed over the nasal passage, the shape of compliant nose bridge seal 135 assists in opening the nasal passage, such as with an outward springing force which pulls open the nasal passages. As a result, the nasal passage is assisted in opening.

In another embodiment, patient interface 110 interacts with and slightly laterally stretches the cheek skin of patient 101, where the cheek skin is the skin starting at the lateral edges of the nose and extending laterally as far as the skin above the zygomatic arches. This lateral stretching of the cheek skin pulls the nasal passages slightly laterally to a more open state. With reference to FIGS. 1 and 3-7, in some embodiments, the positioning of side straps 112-1 and 112-3 assists in providing lateral pressure to facial skin interface 130 to effect the lateral stretching of the cheek skin. With reference to FIG. 5A, zygomatic facial interface portions 831-1 and 831-2 and the positioning of side straps 112-1 and 112-3, in some embodiments, act in concert to slightly laterally stretch the cheek skin of patient 101. It should be appreciated that this cheek skin stretching operates in a similar fashion to the Cottle test, which is used to evaluate nasal valve stenosis. As a result of bilateral facial skin stretching the nasal passage is assisted in opening.

In another embodiment, the nasal passage opener is a fluidly adjustable bladder or bladders (e.g., bladders 736), as described in Section 1. For example, bladders 736 are inflated at the nasal passage. The inflation provides force onto portions of the nasal passage, which may pull the nasal passage into a more open state, such as by adhesively pulling the nasal passages open in certain regions and/or laterally stretching cheek skin of a patient. As a result, the nasal passage is assisted in opening.

In some embodiments, one or more of facial cheek skin stretching may be utilized, a compliant nose bridge seal, and inflatable bladders may be used in combination for opening the nasal passages of patient 101.

In one embodiment, the nasal passage opener is integrated with mask 110. Alternatively, the nasal passage opener is removable from mask 110.

FIG. 11 depicts an embodiment of a method for assisting in opening a nasal passage.

At 1110, a ventilation mask is sealed over a face of a patient, wherein the ventilation mask is disposed over a nasal passage. For example, mask 110 is sealed over the face of patient 101, wherein mask 110 is disposed over a nasal passage.

At 1120, nasal passage is assisted in opening by the ventilation mask disposed over the nasal passage. For example, the nasal passage is assisted in opening by compliant nose bridge seal disposed over the nasal passage and/or by lateral cheek skin stretching provided by mask 110.

In one embodiment, at 1122, a cross-sectional area of a nasal passage is increased. For example, the cross-sectional area of the nasal passage is increased because of the nasal passage opener.

In another embodiment, at 1124, a bladder is adjusted to assist in opening of the nasal passage. For example, a single bladder is inflated to urge in the opening of a nasal passage.

In a further embodiment, at 1126, a plurality of bladders is adjusted to assist in opening of the nasal passage. For example, a plurality of bladders (e.g., bladders 736) are inflated, such that it urges open the nasal passage. As a result, the cross-sectional area of the nasal passage is increased.

Figure 12:
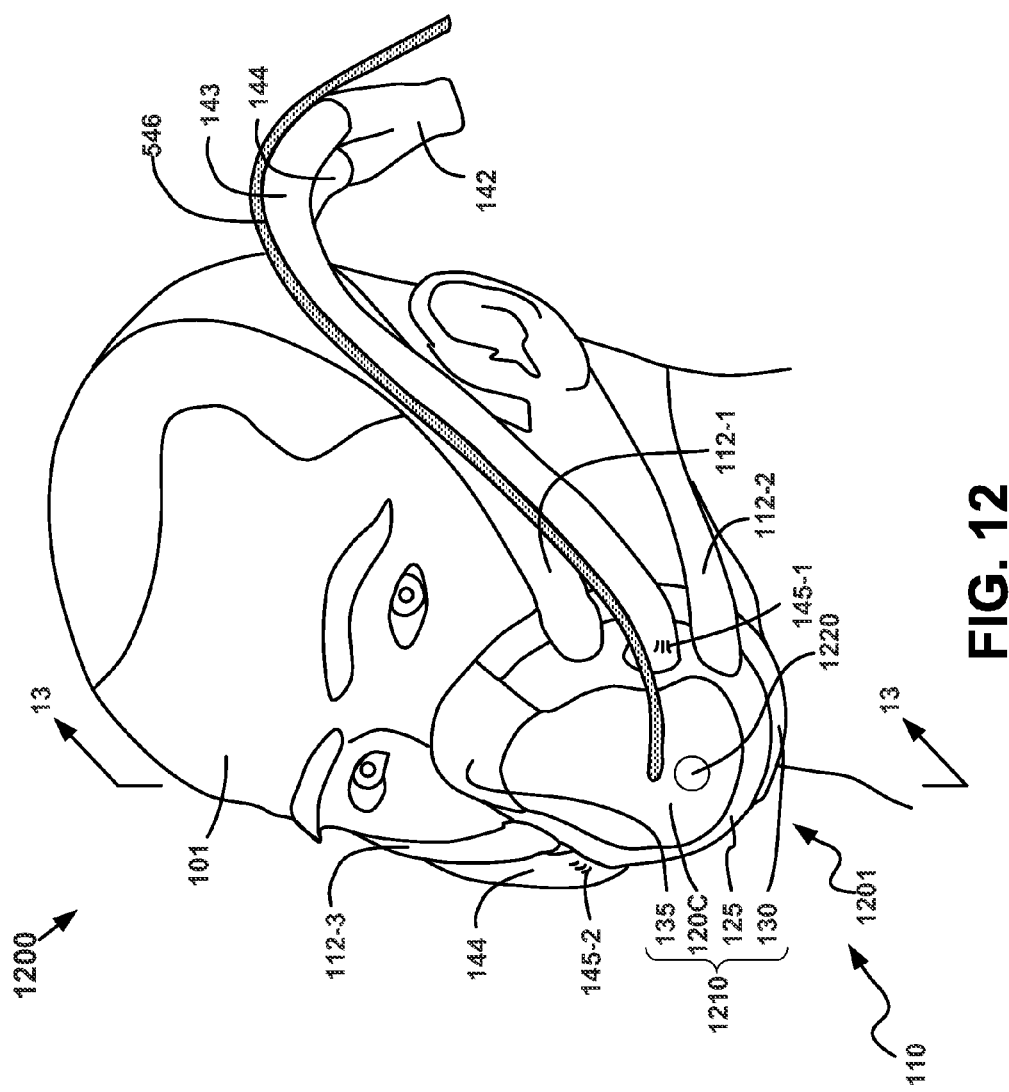
FIG. 12 shows a front perspective view of a non-invasive patient interface with carbon-dioxide sampling device for non-invasively measuring carbon dioxide in exhaled breath, in accordance with an embodiment.

Section 4: a Carbon-Dioxide Sampling Device for Noninvasively Measuring Carbon Dioxide Tn Exhaled Breath With reference now to FIG. 12, in accordance with an embodiment, a front perspective view 1200 is shown of a non-invasive ventilation patient interface 110, which is also referred to herein as a mask 110, with carbon-dioxide sampling device 1201 for non-invasively measuring carbon dioxide in exhaled breath. Patient interface 110 includes a carbon-dioxide sampling device 1201, straps 112-1, 112-2 and 112-3, an inhalation gas supply line 144, which is also referred to herein as limb 144 of the breathing circuit 140, and an exhalation gas collection line 143, which is also referred to herein as limb 143 of the breathing circuit 140. The inhalation gas supply line may be identified with limb 144 of the breathing circuit 140, as previously described; and, the exhalation gas collection line may be identified with limb 143 of the breathing circuit 140, as previously described; however, these identifications of the inhalation gas supply line and the exhalation gas collection line are by way of example, without limitation thereto, as other implementations of the inhalation gas supply line and the exhalation gas collection line are within the spirit and scope of embodiments described herein. In addition, patient interface 110 may also include a y-piece 142, as previously described, which functions as a gas-line coupling.

With further reference to FIG. 12, in accordance with an embodiment, the carbon-dioxide sampling device 1201 is configured to non-invasively measure carbon dioxide in exhaled breath. The carbon-dioxide sampling device 1201 includes a breath-sampling chamber 1210, and a carbon-dioxide collector 502, which is also referred to herein as breath scoop 502. The carbon-dioxide collector 502 may be identified with the breath scoop 502, as previously described; however, this identification of the carbon-dioxide collector 502 is by way of example, without limitation thereto, as other implementations of the carbon-dioxide collector 502 are within the spirit and scope of embodiments described herein. The breath-sampling chamber 1210 is configured to be disposed over a patient's mouth and/or nose, and configured to seal with a patient's face preventing unintentional leakage of respiratory gases from the breath-sampling chamber 1210. By way of example without limitation thereto, the breath sampling chamber 1210 includes a frame 125, a facial skin interface 130, a compliant nose bridge seal 135, and an interchangeable patient interface insert 120C, which have been previously described. The carbon-dioxide collector 502 is disposed in the breath-sampling chamber 1210. The carbon-dioxide collector 502 is configured to be disposed in proximity to, and outside of, the nose and/or mouth of the patient 101, and to collect a sample of exhaled breath from the patient 101. The straps 112-1, 112-2 and 112-3 are configured to hold the breath-sampling chamber 1210 in place over the patient's mouth and/or nose, and to apply tension to make a seal with a patient's face preventing unintentional leakage of respiratory gases from the breath-sampling chamber 1210. The inhalation gas supply line 144 is coupled with the breath-sampling chamber 1210, and is configured to transport oxygen gas to the patient 101. The exhalation gas collection line 143 is coupled with the breath-sampling chamber 1210, and is configured to remove exhaled gases from the breath-sampling chamber 1210.

With further reference to FIG. 12, in accordance with an embodiment, patient interface 110 also includes an interchangeable insert 120C that is disposed at a front of the breath-sampling chamber 1210. The carbon-dioxide sampling device 1201 also includes a breath-sampling line 546, as previously described. Thus, patient interface 110 also includes a breath-sampling line 546 configured to transport a sample of the exhaled breath from the patient 101 collected by the carbon-dioxide collector 502. The interchangeable insert 120C includes a breath-sampling port 501 that is configured to couple the breath-sampling line 546 with the carbon-dioxide collector 502. The breath-sampling line 546 is configured to transport a sample of exhaled breath from the patient 101 collected by the carbon-dioxide collector 502. A portion of the breath-sampling line 546 proximate to the breath-sampling chamber 1210 is securely attached to the breath-sampling chamber 1210, and is configured to prevent accidental interference by the patient 101 with the breath-sampling line 546. By way of example, the breath-sampling chamber 1210 may be configured as a respiration chamber of a breathing mask 110, without limitation thereto.

With further reference to FIG. 12, in accordance with an embodiment, the carbon-dioxide sampling device 1201 may also include a carbon-dioxide indicator 1220 that is configured to indicate when a threshold level of carbon dioxide is exceeded in the exhaled breath from the patient 101. Thus, patient interface 110 includes the carbon-dioxide indicator 1220 that is configured to indicate when a threshold level of carbon dioxide is exceeded in the exhaled breath from the patient 101. The carbon-dioxide indicator 1220 includes a visible portion that is configured to change an appearance of the visible portion when a threshold level of carbon dioxide is exceeded in the exhaled breath from the patient 101. The carbon-dioxide indicator 1220 may also include a visible portion that is configured to change color when a threshold level of carbon dioxide is exceeded in the exhaled breath from the patient 101. The carbon-dioxide indicator 1220 may be mounted conspicuously on a portion of the carbon-dioxide sampling device 1201 to be readily observable by an attendant of the patient 101.

Figure 13:
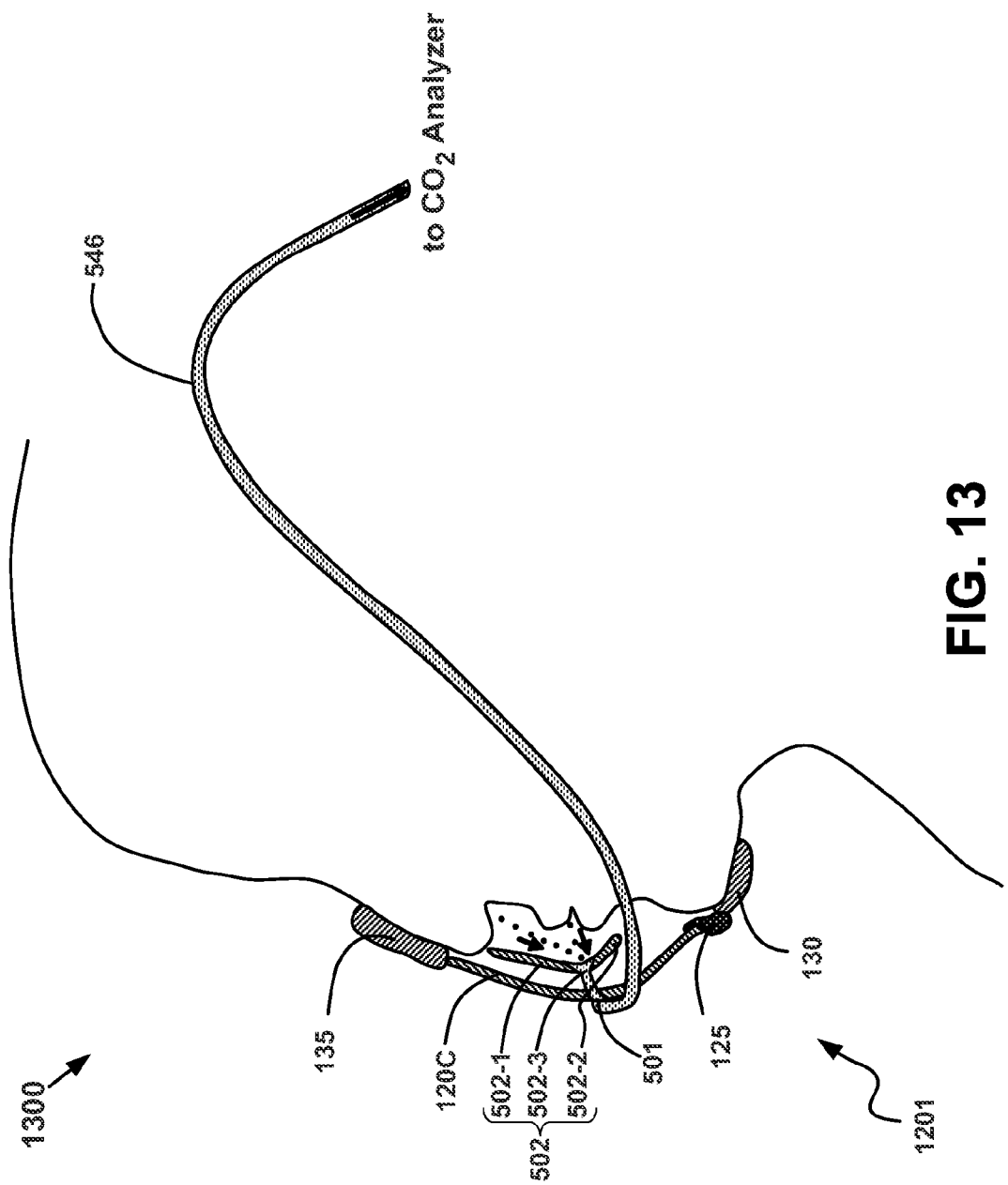
FIG. 13 shows a cross-sectional view of the non-invasive patient interface of FIG. 12 illustrating the carbon-dioxide sampling device including a carbon dioxide collector, in accordance with an embodiment.

With reference now to FIG. 13, in accordance with an embodiment, a cross-sectional view 1300 is shown of patient interface 110 taken along line 13-13 of FIG. 12. FIG. 13 illustrates the carbon-dioxide sampling device 1201 including the breath-sampling chamber 1210, and a carbon-dioxide collector 502. As shown in FIG. 13, component parts of the breath-sampling chamber 1210 are also shown in cross-section, for example, frame 125, facial skin interface 130, compliant nose bridge seal 135, and interchangeable patient interface insert 120C, covering the patient's mouth and/or nose. Thus, the breath-sampling chamber 1210 is configured to be disposed over a patient's mouth and nose, as shown. In other embodiments, a similar breath-sampling chamber may be disposed over only the nose or only the mouth of a patient. The breath-sampling chamber 1210 is also configured to seal with a patient's face preventing unintentional leakage of respiratory gases from the breath-sampling chamber 1210. The carbon-dioxide collector 502 is disposed in the breath-sampling chamber 1210, and is fluid dynamically isolated from flow of fresh respiratory gases such that exhaled breath may be captured therein and directed toward breath-sampling line 546. The carbon-dioxide collector 502 is configured to be disposed in proximity to, and outside of, a respiratory opening (nose, mouth, or nose and mouth) of the patient 101, and to collect a sample of exhaled breath from the patient 101. As shown in FIG. 13, the carbon-dioxide collector 502 includes an upper portion 502-1 of the breath scoop 502, a lower portion 502-2 of the breath scoop 502, and a breath-scoop channel 502-3. The upper portion 502-1 of the breath scoop 502 and the lower portion 502-2 of the breath scoop 502 are designed to capture the patient's breath either from the nose or the mouth of the patient 101, is indicated by the respective arrows in FIG. 13 directed from the patient's nose and mouth, with substantially no dilution with respiratory gases supplied to the patient 101. The breath-sampling line 546 is also shown in FIG. 13; unlike other elements of the figure, the breath-sampling line 546 is not shown in cross-section, but rather, lies generally outside of the plane of the figure, for the purpose of facilitating the description. The carbon-dioxide collector 502 communicates with the breath-sampling line 546 through the breath-sampling port 501. Thus, the carbon-dioxide collector 502 is configured to collect a sample of the exhaled breath from the patient 101 that is substantially undiluted by respiratory gases supplied for the patient's breathing.

With further reference to FIG. 13, in accordance with an embodiment, the carbon-dioxide sampling device 1201 may further include a carbon-dioxide sensor (not shown) that is configured to sense a level of carbon dioxide in the exhaled breath of the patient 101, and to output a carbon-dioxide sensor signal commensurate with the level of carbon dioxide. In one embodiment, the carbon-dioxide sensor may be co-located with the carbon-dioxide collector 502, so that a sensor signal commensurate with the content of carbon dioxide in the breath of the patient 101 may be obtained as close as possible to the source of exhaled breath, yet non-invasively. Thus, the carbon-dioxide collector 502 may include the carbon-dioxide sensor.

Figure 14:
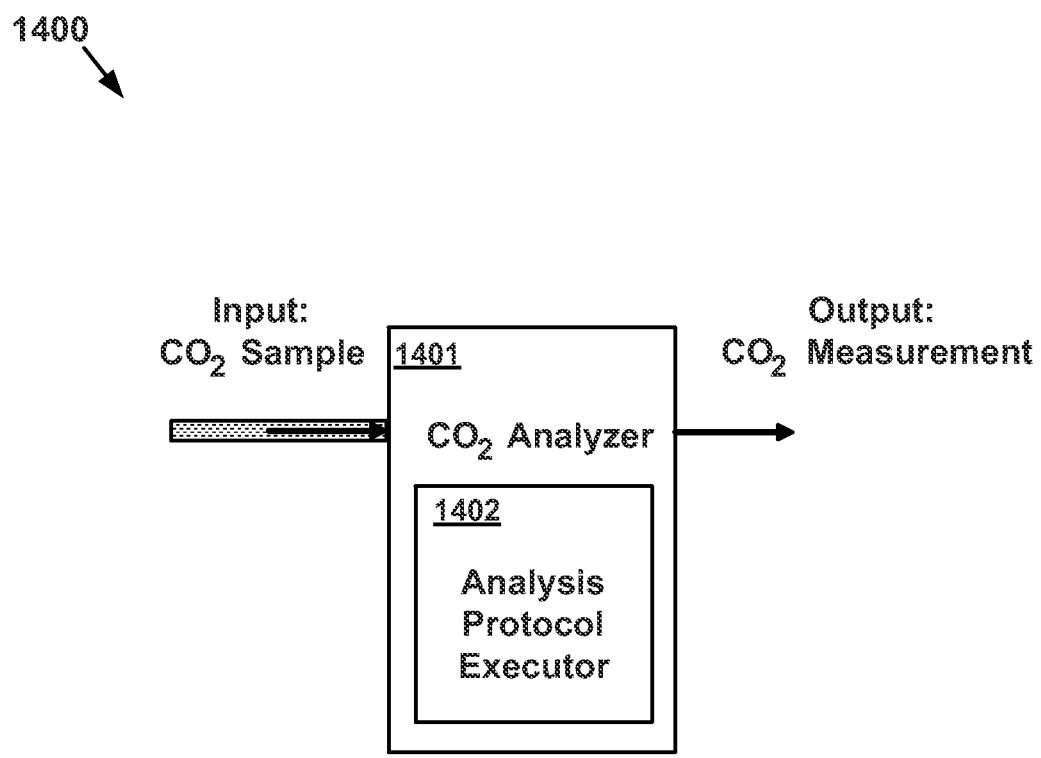
FIG. 14 shows a schematic diagram of a carbon-dioxide analyzer for converting a sample of exhaled breath from the patient into a measurement of carbon dioxide content in the sample of exhaled breath from the patient, in accordance with an embodiment.
Figure 15:
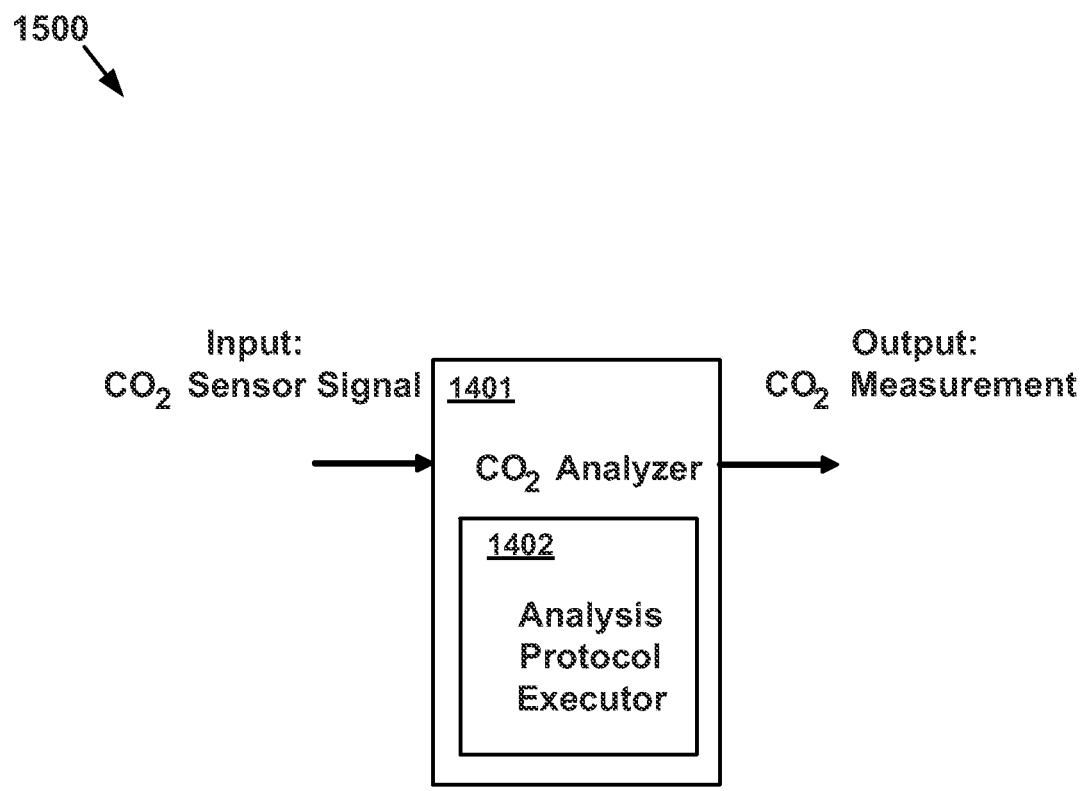
FIG. 15 shows a schematic diagram of an alternative embodiment for the carbon-dioxide analyzer for converting a sensor signal form a carbon-dioxide sensor into a measurement of carbon dioxide content in a sample of exhaled breath from the patient, in accordance with an embodiment.

With reference now to FIGS. 14 and 15, in accordance with alternative embodiments, a schematic diagram 1400 is shown of a carbon-dioxide analyzer 1401 of one embodiment in FIG. 14; and, a schematic diagram 1500 is shown of a carbon-dioxide analyzer 1401 of an alternative embodiment in FIG. 15. The carbon-dioxide sampling device 1201 may also include the carbon-dioxide analyzer 1401 of either embodiment. As shown in FIG. 14, the carbon-dioxide analyzer 1401 is configured to determine, from a sample of exhaled breath from the patient 101, a measurement of carbon-dioxide content in the sample of exhaled breath from the patient 101. As shown in the alternative embodiment of FIG. 15, for example, for a carbon-dioxide sensor that may be co-located with the carbon-dioxide collector 502, the carbon-dioxide analyzer 1401 is configured to convert a sensor signal received from the carbon-dioxide sensor into a measurement of carbon dioxide content in the sample of exhaled breath from the patient 101. The carbon dioxide analyzer 1401 also includes a carbon-dioxide analysis protocol executor 1402 to provide an accurate measurement of carbon dioxide content in the sample of the exhaled breath from the patient 101 that is substantially unaffected by dilution from respiratory gases supplied for the patient's breathing. Both the carbon-dioxide analyzer 1401 and the carbon-dioxide analysis protocol executor 1402 may include: hardware, firmware, hardware and software, firmware and software, hardware and firmware, and hardware and firmware and software, any of which are configured to assist in the analysis of the sample of exhaled breath from the patient 101 to obtain a measurement of carbon dioxide content that is substantially undiluted by respiratory gases supplied for the patient's breathing. Moreover, the carbon-dioxide analyzer 1401 and the carbon-dioxide analysis protocol executor 1402 may be configured as separate electronic devices that are separate from any ventilator 160 used to ventilate a patient 101 with respiratory gases. The carbon-dioxide analyzer 1401 and the carbon-dioxide analysis protocol executor 1402 may include, by way of example without limitation thereto, a computer system.

With reference now to FIG. 16, in accordance with an embodiment, a flowchart 1600 is shown of a method for non-invasively measuring carbon dioxide in exhaled breath of a patient. The method includes the following operations. At 1610, a carbon-dioxide collector is disposed in proximity to, and outside of, the nose and mouth of the patient. At 1620, a sample of exhaled breath is collected from the patient. The sample of the exhaled breath from the patient is substantially undiluted by respiratory gases supplied for the patient's breathing, for example, as described above, by means of the breath scoop 520. The method may further include the following operations. At 1630, a level of carbon dioxide in the exhaled breath of the patient is sensed with a carbon-dioxide sensor. At 1640, a sensor signal is output that is commensurate with the level of carbon dioxide. At 1650, the sensor signal is converted into a measurement of carbon dioxide content in the sample of exhaled breath from the patient with the carbon-dioxide analyzer. In addition, at 1660, a carbon-dioxide analysis protocol may be applied to provide an accurate measurement of carbon dioxide content in the sample of the exhaled breath from the patient that is substantially unaffected by dilution from respiratory gases supplied for the patient's breathing.

Figure 17:
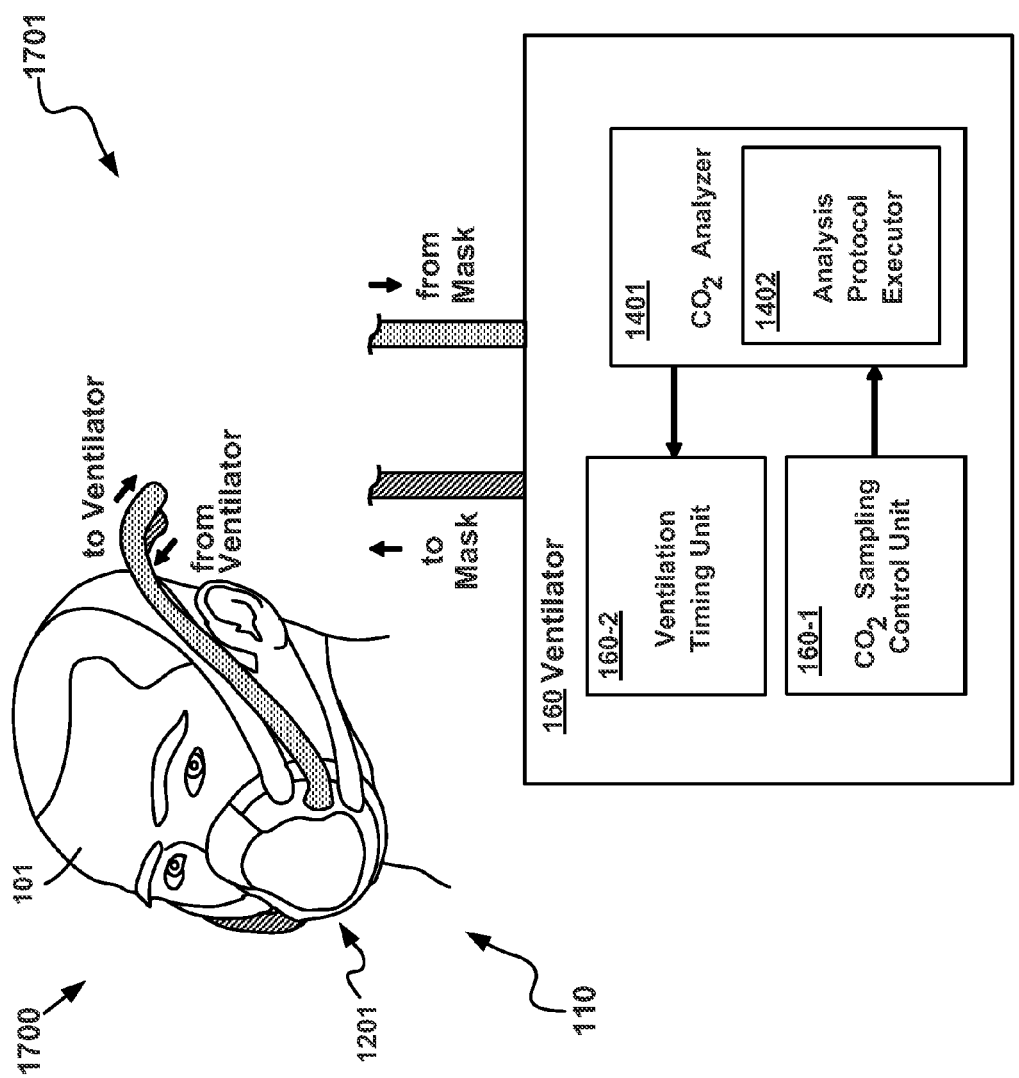
FIG. 17 shows a schematic diagram of a carbon-dioxide sampling system for accurately monitoring carbon dioxide in exhaled breath, in accordance with an embodiment.

Section 5: a Carbon-Dioxide Sampling System for Accurately Monitoring Carbon Dioxide in Exhaled Breath With reference now to FIG. 17, in accordance with an embodiment, a schematic diagram 1700 is shown of a carbon-dioxide sampling system 1701 for accurately monitoring carbon dioxide in exhaled breath. Herein, "accurately" refers to measuring carbon dioxide levels closely to their actual (true) values. The carbon-dioxide sampling system 1701 includes a ventilator 160. The ventilator 160 is configured to ventilate a patient 101 with respiratory gases. The ventilator 160 includes a carbon-dioxide sampling control unit 160-1, and a carbon-dioxide analyzer 1401. Although similar to the carbon-dioxide analyzer 1401 described above, in contrast with the carbon-dioxide analyzer 1401 described above, the carbon-dioxide analyzer 1401 is configured as an integral part of the ventilator 160, and therefore, is also configured as an integral part of the carbon-dioxide sampling system 1701. The carbon-dioxide sampling control unit 160-1 is configured to control the timing of sampling of carbon dioxide in the exhaled breath of a patient 101, and to control the timing of an analysis of exhaled gases by the carbon-dioxide analyzer 1401. The carbon-dioxide sampling control unit 160-1 may include: hardware, firmware, hardware and software, firmware and software, hardware and firmware, and hardware and firmware and software, any of which are configured to assist in the sampling of the sample of exhaled breath from the patient 101 to obtain a measurement of carbon dioxide content that is substantially undiluted by respiratory gases supplied for the patient's breathing. Thus, the carbon-dioxide sampling control unit 160-1 is configured to control collection of a sample of exhaled breath from the patient 101 that is substantially undiluted by respiratory gases supplied for the patient's breathing.

With further reference to FIG. 17, in accordance with an embodiment, the ventilator 160 further includes a ventilation timing unit 160-2. The ventilation timing unit 160-2 may include: hardware, firmware, hardware and software, firmware and software, hardware and firmware, and hardware and firmware and software, any of which are configured to assist in ventilating a patient 101 at regular intervals based on measured levels of carbon dioxide in the breath of the patient 101. The carbon-dioxide analyzer 1401 is configured to regulate the ventilation timing unit 160-2 to ventilate a patient 101 at regular intervals based on measured levels of carbon dioxide in the breath of the patient 101. The carbon dioxide analyzer 1401 may also include an analysis protocol executor 1402 to provide an accurate measurement of carbon dioxide content in the sample of the exhaled breath from the patient 101 that is substantially unaffected by dilution from respiratory gases supplied for the patient's breathing, as previously described.

With further reference to FIG. 17, in accordance with an embodiment, the carbon-dioxide sampling system 1701 may also include a breath-sampling chamber 1210. As previously described, the breath-sampling chamber 1210 is configured to be disposed over a respiratory opening of a patient (nose, mouth, or nose and mouth), and is configured to seal with a patient's face preventing unintentional leakage of respiratory gases from the chamber. Moreover, the breath-sampling chamber 1210 is configured to be coupled to the ventilator 160, as an integral part of the carbon-dioxide sampling system 1701. The carbon-dioxide sampling system 1701 may further include a carbon-dioxide collector 502, as previously described, which is disposed in the breath-sampling chamber 1210. The carbon-dioxide sampling system 1701 may further include an exhalation-gas collection line 143, as previously described, coupled to the breath-sampling chamber 1210 configured to collect exhaled gases in a breath exhaled by the patient 101, and to transport the exhaled gases to the carbon-dioxide analyzer 1401.

Figure 18:
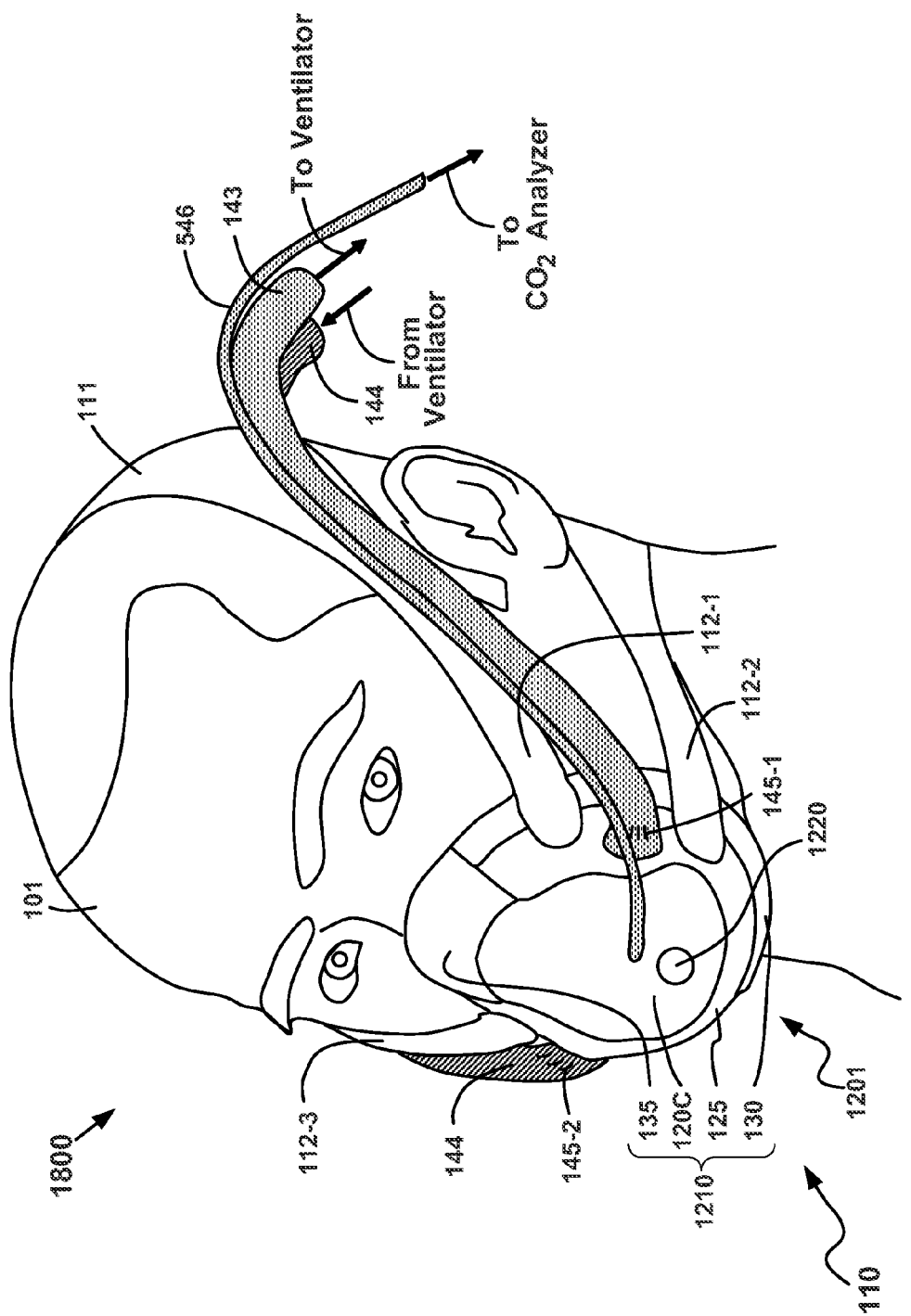
FIG. 18 shows a front perspective view of the non-invasive patient interface of a combined non-invasive patient interface and carbon-dioxide sampling system, in accordance with an embodiment.

With reference now to FIG. 18, in accordance with an embodiment, a front perspective view 1800 is shown of patient interface 110 of a combined non-invasive ventilation patient interface 110 and carbon-dioxide sampling system 1701. The combined interface 110 and system 1701 includes patient interface 110, and a carbon-dioxide sampling system 1701, as described above in the discussions of FIGS. 9 and 14, respectively. The breath-sampling chamber 1210 includes a respiration chamber of a breathing mask 110. The combined patient interface 110 and carbon-dioxide sampling system 1701 may further include a separate breath-sampling line 546 that is configured to transport a sample of the exhaled breath from the patient 101 to the carbon-dioxide analyzer 1401. The combined patient interface 110 and carbon-dioxide sampling system 1701 may also include an inhalation gas supply line 144 and an exhalation gas collection line 143. The inhalation gas supply line 144 is coupled with the breath-sampling chamber 1210, and is configured to transport oxygen gas to the patient 101. The exhalation gas collection line 143 is coupled with the breath-sampling chamber 1210, and is configured to remove exhaled gases from the breath-sampling chamber 1210. In an alternative embodiment, the exhalation gas collection line 143 may be configured to transport a sample of the exhaled breath from the patient 101 to the carbon-dioxide analyzer 1401, instead of the separate breath-sampling line 546. The exhalation-gas collection line 143 is securely attached to the breath-sampling chamber 1210, and is configured to prevent accidental interference by the patient 101 with the exhalation-gas collection line 143. The combined patient interface 110 and carbon-dioxide sampling system 1701 may also include a carbon-dioxide indicator 1220, as previously described in the discussion of FIG. 12. The carbon-dioxide indicator 1220 is configured to indicate when a threshold level of carbon dioxide is exceeded in the exhaled breath from the patient 101. The carbon-dioxide indicator 1220 is mounted conspicuously on a portion of the mask 110 to be readily observable by an attendant of the patient 101.

Figure 19:
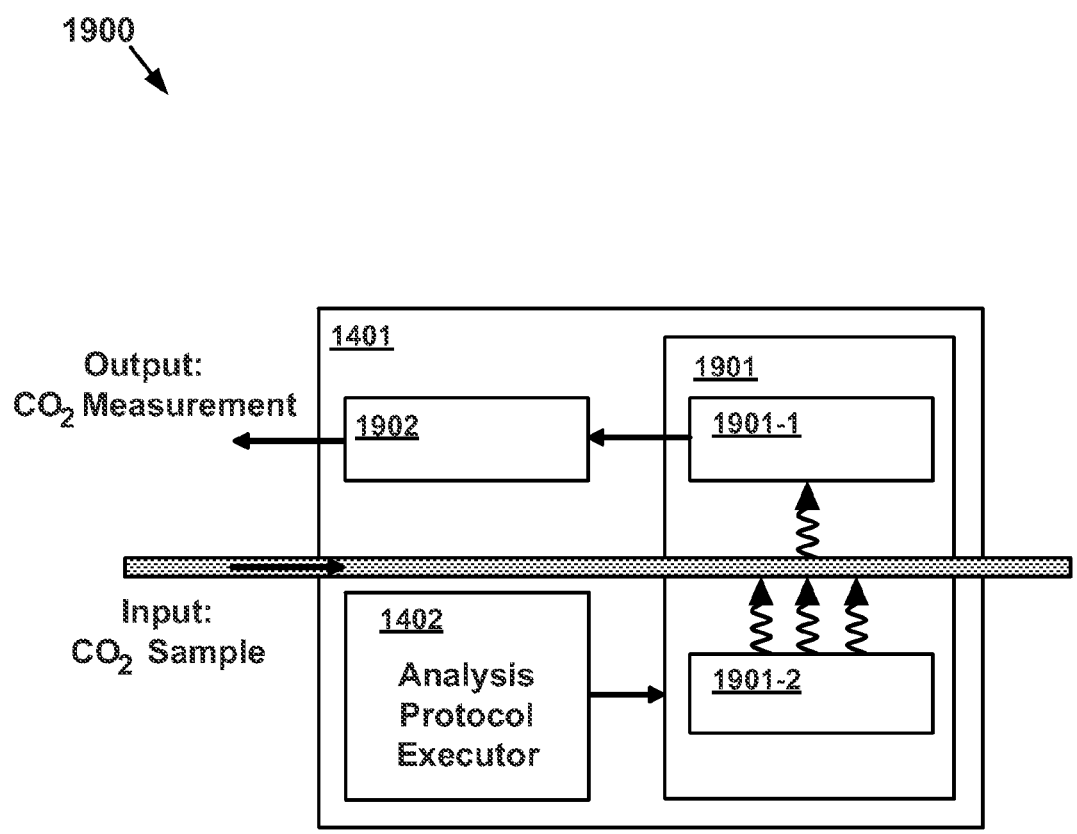
FIG. 19 shows a schematic diagram of a carbon-dioxide analyzer including a carbon-dioxide sensor configured to sense a level of carbon dioxide in exhaled breath of the patient, in accordance with an embodiment.

With reference now to FIG. 19, in accordance with an embodiment, a schematic diagram 1900 is shown of the carbon-dioxide analyzer 1401. The carbon-dioxide analyzer 1401 may further include a carbon-dioxide sensor 1901. The carbon-dioxide sensor 1901 is configured to sense a level of carbon dioxide in the exhaled breath of the patient 101, and to output a sensor signal commensurate with the level of carbon dioxide. The carbon dioxide analyzer 1401 may also include a sensor-signal converter 1902. The sensor-signal converter 1902 may include: hardware, firmware, hardware and software, firmware and software, hardware and firmware, and hardware and firmware and software, any of which are configured to convert the sensor signal into a measurement of carbon dioxide content in the sample of the exhaled breath from the patient 101. Thus, the sensor-signal converter 1902 is configured to convert the sensor signal into a measurement of carbon dioxide content in the sample of the exhaled breath from the patient 101. The carbon-dioxide analyzer 1401 may further include an analysis protocol executor 1402. The analysis protocol executor 1402 is configured to provide an accurate measurement of carbon dioxide content in the sample of the exhaled breath from the patient 101 that is substantially unaffected by dilution from respiratory gases supplied for the patient's breathing, as previously described. The carbon-dioxide sensor 1901 may include an infra-red detector 1901-1, and a source of infra-red radiation 1901-2. The infra-red detector 1901-1, by way of example, without limitation thereto, may be a semiconductor photo-diode. The infra-red detector 1901-1 is configured to measure the absorbance of infra-red radiation at a frequency within an absorption band of carbon dioxide for the infra-red radiation, and to generate a sensor signal commensurate with the level of carbon dioxide based on absorbance.

Figure 20:
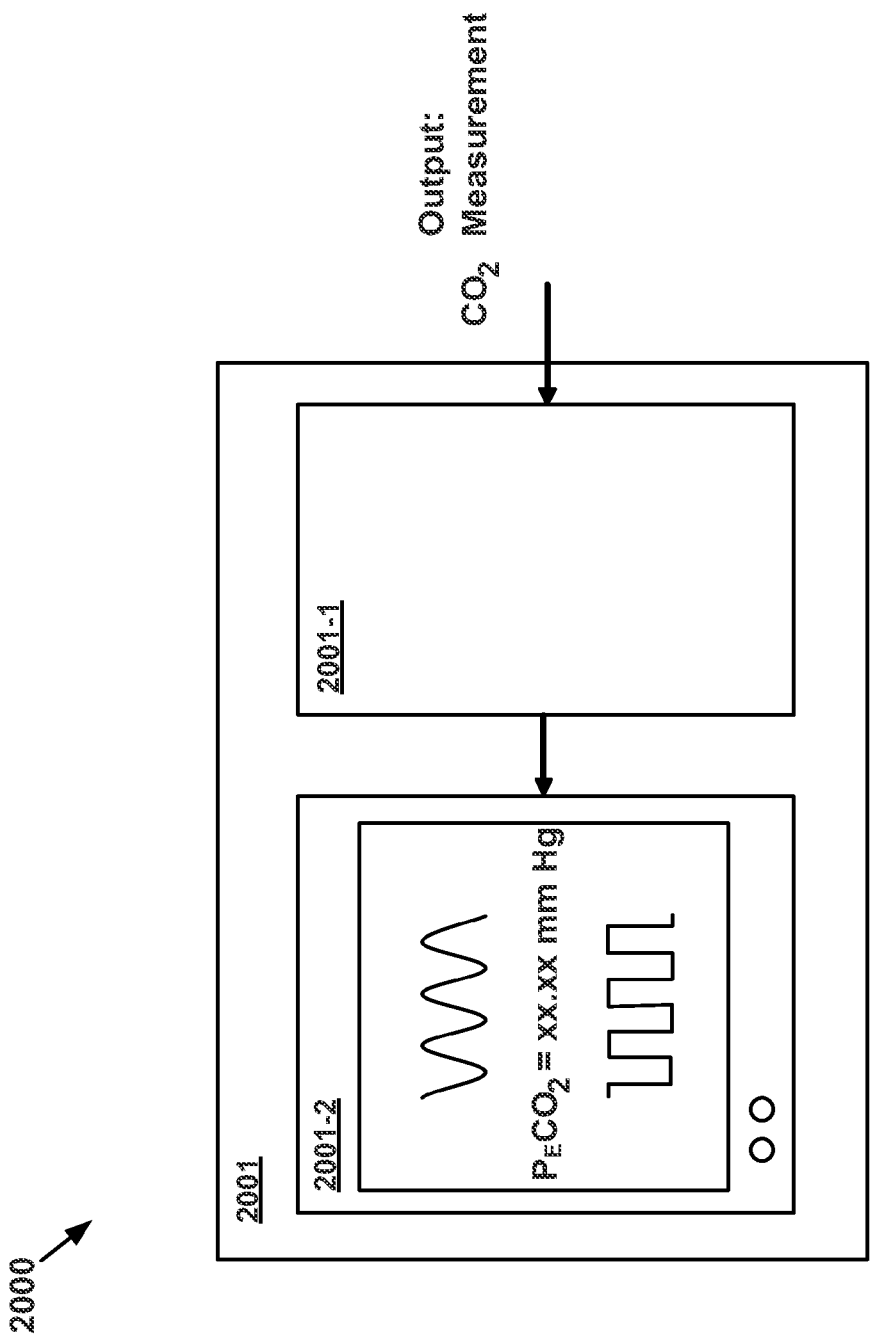
FIG. 20 shows a schematic diagram of a combination carbon-dioxide measurement display and recorder, in accordance with an embodiment.

With reference now to FIG. 20, in accordance with an embodiment, a schematic diagram 2000 is shown of a combination 2001 of a carbon-dioxide measurement display 2001-2 and a carbon-dioxide measurement recorder 2001-1. The carbon-dioxide measurement recorder 2001-1 may be a computer system and/or the memory of a computer system, without limitation thereto. As shown in FIG. 20, the carbon-dioxide measurement display 2001-2 may be configured to display data from the ventilator 160, for example, such as: respiration rate, indicated by the sinusoidal waveform on the carbon-dioxide measurement display 2001-2; the activity of the ventilator 160 in supplying respiratory gases, for example, oxygen, to the patient 101, indicated by the square-wave waveform; and, a textual display of the partial pressure of carbon dioxide in exhaled breath, $P_ECO_2$. As shown in FIG. 20, the partial pressure of carbon dioxide in exhaled breath may be displayed as a decimal number in units of pressure, given in units of millimeters of mercury (mm Hg), without limitation thereto.

Figure 21:
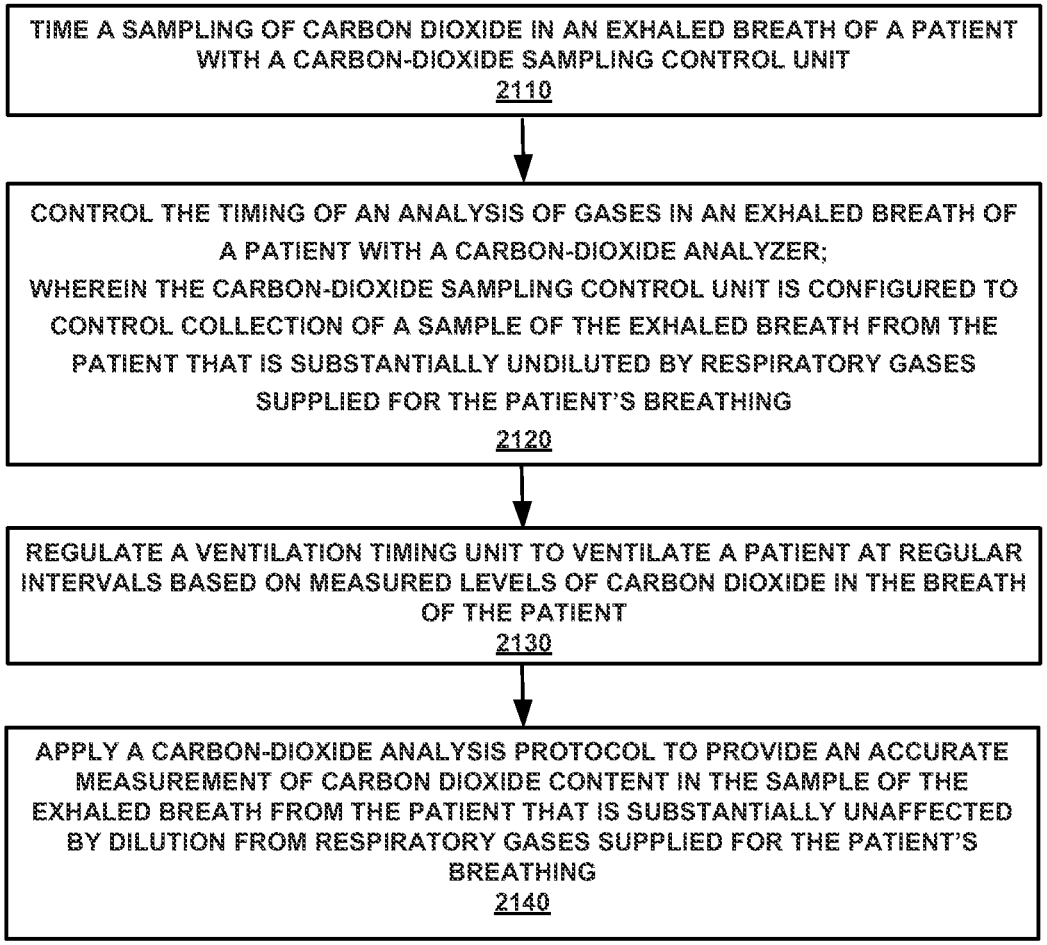
FIG. 21 shows a flowchart of a method for accurately monitoring carbon dioxide in exhaled breath, in accordance with an embodiment.

With reference now to FIG. 21, in accordance with an embodiment, a flowchart 2100 is shown of a method for accurately monitoring carbon dioxide in exhaled breath of a patient. The method includes the following operations. At 2110, a sampling of carbon dioxide in an exhaled breath of a patient is timed with a carbon-dioxide sampling control unit.

At 2120, the timing of an analysis of gases in an exhaled breath of a patient is controlled with a carbon-dioxide analyzer. The carbon-dioxide sampling control unit is configured to control collection of a sample of the exhaled breath from the patient that is substantially undiluted by respiratory gases supplied for the patient's breathing. Therefore, the collection of the exhaled breath sample may be timed not to coincide with a time when respiratory gases, for example, oxygen, are being supplied to the patient. The method may also include the following operation. At 2130, a ventilation timing unit is regulated to ventilate a patient at regular intervals based on measured levels of carbon dioxide in the breath of the patient. In addition, at 2140, a carbon-dioxide analysis protocol may be applied to provide an accurate measurement of carbon dioxide content in the sample of the exhaled breath from the patient that is substantially unaffected by dilution from respiratory gases supplied for the patient's breathing.

Section 6: Interchangeable Inserts

Various embodiments provide a ventilation mask with a removable insert. In one embodiment, the front portion of the mask is removable to enable access to a respiratory opening region such as either the mouth, nose region, or both the mouth and nose regions of a patient without requiring removal of the entire mask and strap system. The nose region would comprise at least the nasal (nose) opening and may further comprise one to several centimeters surrounding the nasal opening. The mouth region would comprise at least the oral (mouth) opening and may further comprise one to several centimeters surrounding the oral opening. This enables quick access to the mouth and/or nose region while simultaneously ventilating the patient.

The removable insert enables a caregiver access to the mouth and/or nose region of the patient that would be inaccessible with a conventional ventilation mask on the patient. With a conventional mask, the entire mask and strapping system would need to be removed to gain access to the nose and/or mouth region of the patient. Thus, the removable insert of saves considerable time because mask adjustment is significantly reduced, especially when access to the mouth and/or nose region of the patient is desired.

The removable insert enables the patient to perform many tasks while being simultaneously ventilated. For example, a patient can eat, take medication, brush teeth, talk, etc., with the insert removed. It should be appreciated that the patient is still ventilated even with the removable section of the mask removed from the frame portion.

Referring back to FIG. 1, domed front portion 120 is removable from frame portion 125 to enable access to the mouth and/or nose region of the patient without requiring removal of the frame portion 125 from the patient. In this embodiment, the mouth and/or nose region of the patient can be accessed without removing or adjusting strapping system 111.

Referring back to FIG. 3, a front perspective view of patient interface 110 of a non-invasive ventilation system 160 is shown and illustrates removal/insertion of an interchangeable patient interface insert 120A, in accordance with an embodiment. As depicted, interchangeable patient interface insert 120A is in the removed position to enable access to the nose and/or mouth region of the patient. Interchangeable patient interface insert 120A includes exhaust gas vent ports 123, and is thus designed for use in a vented non-invasive ventilation application. Interchangeable patient interface insert 120A includes one or more tabs 302 (one visible) which correspond with, and seat into, slots 303 that are disposed in the semi-elliptical rim 304 of frame 125. Be applying a pinching pressure on grip regions 121-1 and 121-2 (as illustrated by arrows 301), interchangeable patient interface insert 120A can be compressed slightly so that tabs 302 can be seated into slots 303 and interchangeable patient interface insert 120A can be removably coupled with frame 125. Reversal of the installation process allows for the removal of interchangeable patient interface insert 120A.

It is appreciated that when the removable insert 120A is in the removed position, the patient is still receiving gas flow from limb 143 because the airflow enters the frame portion 125 of the mask. The removable insert enables simultaneous ventilation and access to the mouth and/or nose region of the patient.

In one embodiment, the removable insert includes a graphic or color on the outside surface (facing away from the patient) so the patient can have a customized look. For example, a portion of the removable insert may be opaque or a color such as orange, red, or blue (or configured with multiple colors). Some non-limiting examples of a graphic include: a handlebar mustache, stars, a rainbow, a beard, chin whiskers, a monster face, a smiley face, etc. In another embodiment, the inside surface of the removable insert is scented, such as with cinnamon scent, mint scent, citrus scent, bubble gum scent, or other scent, to provide a pleasing scent to the patient while being ventilated. It is appreciated that the removable insert 120A may be dosed with medication for a controlled release to the patient via either a nasal entry or mouth entry.

In another embodiment, therapeutic devices can be incorporated with the removable insert. For example, a bite plate on the inside surface can be incorporated into the removable insert to function as both a bite plate and a cover for the mask. It is appreciated that any number of therapeutic devices could be incorporated with insert 120A on the inside surface (facing patient) and/or on the outside surface (facing away from the patient).

The removable insert may also be coated in the inside surface with an anti-fogging layer to reduce fogging on the inside surface. Anti-fog coating assists in maintaining a transparent surface which allows an unimpeded view of the nose and lips of a patient, so that a caregiver may easily assess the patient without requiring removal of either patient interface 111 or removable insert 120A (or other removable insert 120 which is coated with anti-fog coating on its interior surface).

Figure 22:
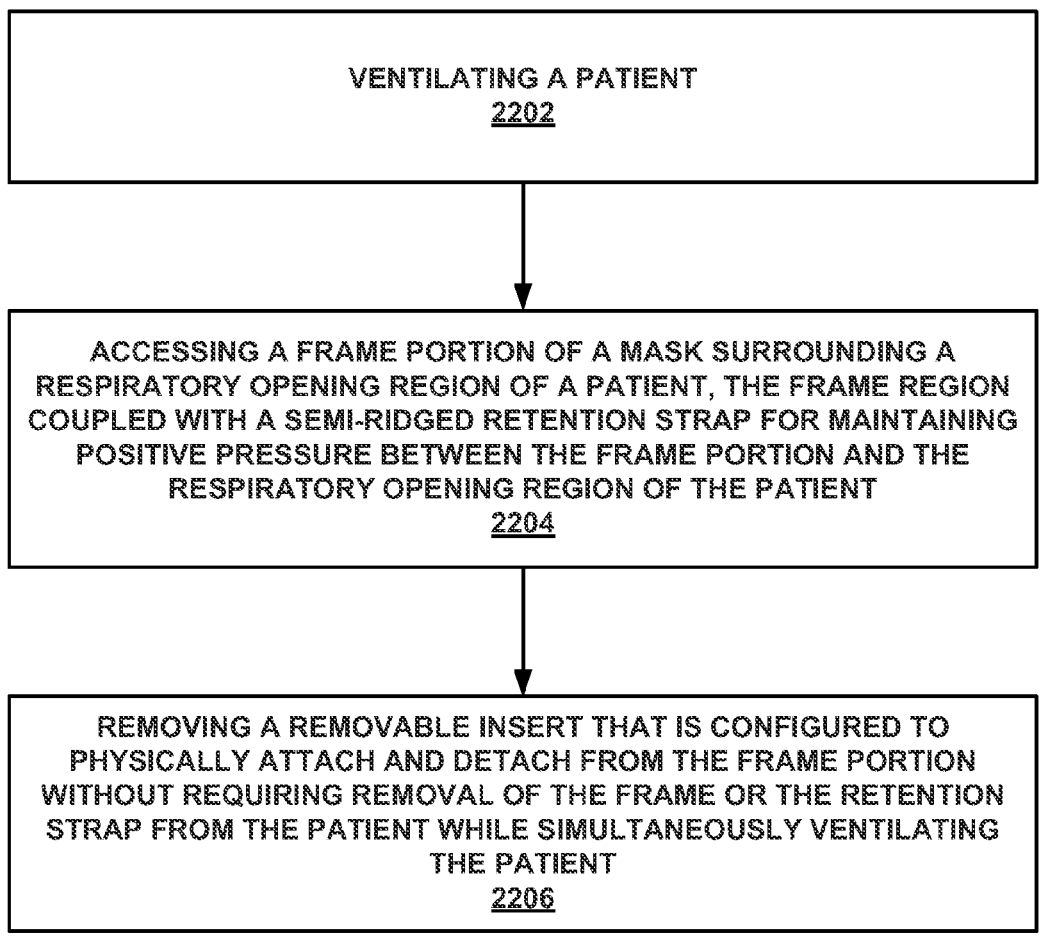
FIG. 22 is a flow diagram of an exemplary method for accessing a respiratory opening of a patient without removing a ventilation mask in accordance with an embodiment.

Referring now to FIG. 22, a method 2200 for accessing a mouth and/or nose region of a ventilated patient is provided. In one embodiment, access to the mouth and/or nose region of a patient is provided while simultaneously ventilating the patient. With method 2200 of, mouth and/or nose region access can be achieved without requiring removal of the mask or mask strapping system from the patient. At 2202, 2200 includes ventilating the patient.

At 2204, method 2200 includes accessing a frame portion of a mask surrounding the mouth and/or nose region of the patient wherein the frame region is coupled with a semi-rigid retention strap for maintaining positive pressure between the frame portion and the mouth region of the patient.

At 2206, 2200 includes removing a removable insert that is configured to physically attach and detach from the frame portion without requiring removal of said frame portion or said retention strap from said patient while simultaneously ventilating the patient.

After the removable insert is removed, access to the nose and/or mouth region of the patient is achieved while simultaneously ventilating the patient.

It is appreciated that the replaceable insert can be used for any number of functions. For example, the removable insert can be selected to provide a therapeutic function to the patient such as a bite block, drug delivery, oral and/or nasal care, feeding, suction, etc. The removable inserts can be configured with any number of ports, filters, drug delivery systems, etc., and can also be colored or include a graphic design. The removable insert enables access to the nose and/or mouth region of the patient while not interrupting ventilation of the patient or requiring removal of the mask from the patient.

Section 7: Lateral Gas Line Configuration

Various embodiments described herein include a lateral configuration of gas delivery limbs coupled with a ventilation mask. The lateral configuration can be used in single limb applications as well as multiple limb applications. However, a dual configuration using bilateral limbs facilitates a cross flow of air across a respiratory opening region (i.e., at least the nose opening and/or mouth opening) of a patient which purges dead space and thus improves ventilation of the patient. In one embodiment, the lateral gas line configuration enables ventilation of a patient even with a removable front portion of the mask in the removed position. This lateral configuration of the gas delivery limbs facilitates access to the nose and/or mouth region of the patient while simultaneously ventilating the patient. While only bilateral limbs are depicted (limb on each lateral side of a patient interface and thus on each side of a patient's face when donned), it is appreciated that only one lateral limb, on either lateral side of the patient interface, may be utilized in some embodiments.

The lateral gas line configurations described herein are also configured to improve comfort and stability of the mask on the patient. For example, in one embodiment, a gas limb is coupled with the mask via a swivel connection which enables the gas limb to swivel with respect to the mask. The swivel mount(s) between the gas limb and the mask frame enables free movement of the gas limb(s) without imparting torque on the mask itself. By reducing the torque on the mask frame, even pressure can be achieved between the mask and the patient, thus improving patient care and comfort.

Referring back to FIG. 1, a bilateral gas line configuration is shown. Breathing circuit 140 includes limbs 143 and 144 which are shown to be disposed in a lateral configuration with respect to the temporal region of the patient. The limb (143, 144) may be coupled to the frame portion 125 via a swivel port connection which enables the limb to rotate with respect to the frame portion 125 without imparting torque to the frame portion of the mask. It is appreciated that the swivel connection between the frame portion 125 and the limb enables the limbs to be moved from a lateral position to a front position shown in FIG. 2 where the limb 143 is shown to be rotated to the front of the patient. In this embodiment, the limbs 143, 144 are positioned such that the patient can lay on the side of their head without having a breathing tube in the way or interfering with ventilation. In one embodiment, limbs 143 and 144 are coupled at Y connector 142 where the Y connector 142 includes one or more swivel connectors.

FIG. 3 shows a bilateral gas line configuration with breathing limbs 143 and 144 positioned laterally with respect to the patient's head. In this embodiment, a front removable insert 120A is shown in the removed position. With the lateral gas line configuration described herein, ventilation can occur with the front removable insert in the removed position because the gas flow is configured to flow across a respiratory opening region (i.e., at least the nose opening and/or mouth opening) of the patient. With the removable insert in the removed position, gas flow can still be delivered to the patient. The described lateral gas line configurations facilitate simultaneous ventilation of a patient while enabling access to the mouth and/or nose region of the patient.

Referring back to FIG. 7, one or more limb of breathing circuit 140 may be coupled with strap system 111. For example, region 715 may include a fastener to removably couple limb 143 to side strap 112 of strap system 111. In this embodiment, at least one portion of the breathing circuit 140 is configured in a parallel relationship with a strap 112 of strap system 111. It is appreciated that orifices 722 may be configured as swivel connections that enable swivel movement of the connected device or tube.

In one embodiment, gas delivery orifices 722 are non-concentric with respiratory opening regions (mouth opening region and nasal opening regions) of a patient. In other words, gas delivery orifice(s) 722 are shifted laterally, away from the midline, with respect to any of these openings. Furthermore, gas delivery orifice 722-1 and 722-2 are shifted laterally with respect to front portion 120; that is, they do not define an opening through any part of front portion 120.

Section 8: Quick Donning Headgear

Various embodiments include a quick donning headgear for patient ventilation. The quick donning headgear described herein enables quick and intuitive application and removal of the headgear so as to improve patient care and reduce time spent donning and removing the headgear from the patient.

In some embodiments, the headgear apparatus includes a semi-rigid strap system that enables intuitive application to the patient. The semi-rigid straps maintain a head-shape of the strap system even when not in use. The semi-rigid design enables faster donning of the headgear as opposed to conventional strap systems because the straps are already pre-arranged in the proper configuration prior to use, thus reducing the effort and/or time involved in applying and/or removing the device. The semi-rigid shape also requires less adjustment compared to conventional strapping systems because it is already in the shape of a human head. It is appreciated that any portion(s) of head strap 111 may include a ridged or semi-rigid material. It is also appreciated that the semi-rigid material may be flexible.

Referring back to FIG. 1, head strap 111 includes side straps 112 (112-1, 112-2, 112-3 and 112-4 (not visible in FIG. 1, but illustrated in FIG. 7). In one embodiment, any portion of straps 112 could be formed of a ridged or semi-rigid material and/or may have elastic properties. In one embodiment, straps 112 retain a head like shape when not applied to a patient.

In one embodiment, straps 112 may include a portion that is semi-rigid and also flexible so that the head shape can be expanded for larger patients without requiring adjustment of straps 112 at the frame portion 125. The head-shape of the strap system 111 also enables greater securing force distribution between the patient's skin and the mask structure because less adjustment is required. Depending on the configuration (nasal, oral, or oral/nasal) of a patient interface 110 which is utilized with strap system 111, the head-shape of the strap system 111 evenly distributes the force around either the patient's mouth region, nose region, or both the mouth region and nose region to reduce possible skin irritations and improve patient comfort.

Referring back to FIG. 7, in some embodiments, one or more of side straps 112 may be configured to change color, such as from opaque to translucent or from opaque to transparent, or from a lighter shade to a darker shade, in response to stress being applied to the side strap 112 which is indicative of over tightening of the side strap 112. Similarly, in some embodiments, one or more of side straps 112 may be configured to change color, such as from opaque to translucent or from opaque to transparent, or from a lighter shade to a darker shade such that an embedded colored thread 712 becomes visibly exposed via the non-patient facing side of a side strap 112 in response to stress being applied to the side strap 112 which is indicative of over tightening of the side strap 112.

Referring back to FIG. 2, the quick donning headgear system 111 may include a quick release tab 212 that can be used for rapid removal of the patient interface 110 from the patient in the event of an emergency. The quick release tab 112 can also be used in donning of the headgear to as to adjust the position of the strap system 111 on the patient's head.

The semi-rigid construction of head strap system 111 provides some amount of inherent rigidity so that when it is in storage, it can be collapsed; but when it's removed from collapsed storage, it easily and naturally returns to a general head shaped structure, so that it is visibly obvious how to position and install head strap system 111 on patient 101 when donning patient interface 110. In this manner, there is no need to sort out where the front, back, top, or bottom is located. In one embodiment, patient interface 110 is packaged with head strap system 111 already pre-attached with frame 125, so that when unpackaged the semi-rigid structure of head strap system 111 causes it to look somewhat like a helmet that can just be pulled quickly over the head and face area of patient 101, much like putting on a catcher's mask.

Section 9: Smart Connections

Various embodiments include "smart connectors" for use with patient ventilators. "Smart" refers to a feature that is user friendly and aids in or prevents misconnections with a ventilator that would configure ventilation improperly for a patient. The smart connectors enable proper configuration of a ventilation system and also can be used to determine continuity of the system. For purposes of the present description, the term "continuity" is used to describe the physical continuity of the ventilation system, meaning that correct parts are used and that the correct parts are properly connected and functioning properly.

In one embodiment, physical similarities and dissimilarities of various ventilation components are used to enable compatible parts to couple together while preventing dissimilar or non-compatible parts from being used. In this way, non-compatible parts are not physically able to couple with non-compatible parts, thus preventing an improper configuration of the system from being used with a patient. Moreover, with respect to the proper connection point, there may be only one orientation in which a smart connector can be coupled to the connection point on the ventilator (in order to prevent inadvertent misconnection). This may be accomplished via design feature (shape), labeling, color coding, or combination of these features. In another embodiment, identifiers such as color, barcode, RFID, etc. are used to distinguish similar and dissimilar parts.

For example, in one embodiment, different classes of parts (e.g., for various patient populations, flow rated, type of ventilation, etc.) can be configured to have unique connector ends that only enable compatible parts to mate with. The special physical configuration of various parts also prevents non-compatible parts to be used.

In another embodiment, the ventilation parts can be color coded. In this embodiment, parts with the same color can be considered compatible and can be used together. Parts with different colors can be considered non-compatible and should not be used together. When looking at a ventilation configuration, a part with a different color from the rest is easily identified as non-compatible and should be replaced with a compatible part with the same color as the rest. In one embodiment, different ventilation methods (e.g., single or dual limb) have different colors indicating different uses. In another embodiment, different colored parts are used to differentiate parts for different patient populations.

In another embodiment, parts with different colors can be compatible. In this embodiment, semi-transparent parts of various colors can be used to create "good" colors and "bad colors." For example, a yellow part can be combined with a blue colored part to create a "good" color of green while a blue part combined with a red part create a "bad" color of purple. It is appreciated that any number of colors, patterns, pictures or any other unique markings could be used in accordance with the embodiments described herein to distinguish ventilation parts.

In another embodiment, various parts of the ventilation system can include a machine readable code or identifier that enables tracking and monitoring of the parts of the ventilation system. For example, in one embodiment, one or more parts of the ventilation system include a barcode or RFID tag that enables identification of the parts and enabled determination of system configuration. In this embodiment, part compatibility can be verified and system configuration can be verified. In one embodiment, the ventilator includes a reader that can read the identifier associated with the parts to determine compatibility and/or system configuration.

In another embodiment, one or more parts of the ventilation system include an electrical lead for enabling a continuity check of one or more portions of the ventilation system. When various parts with the wire lead are coupled, a continuous wire lead is established between the parts. A signal can be passed through the lead to check the lead is continuous. In this embodiment, inadvertent disconnection between any of the parts can be detected, thus improving patient care and ventilatilation functions.

Figure 23:
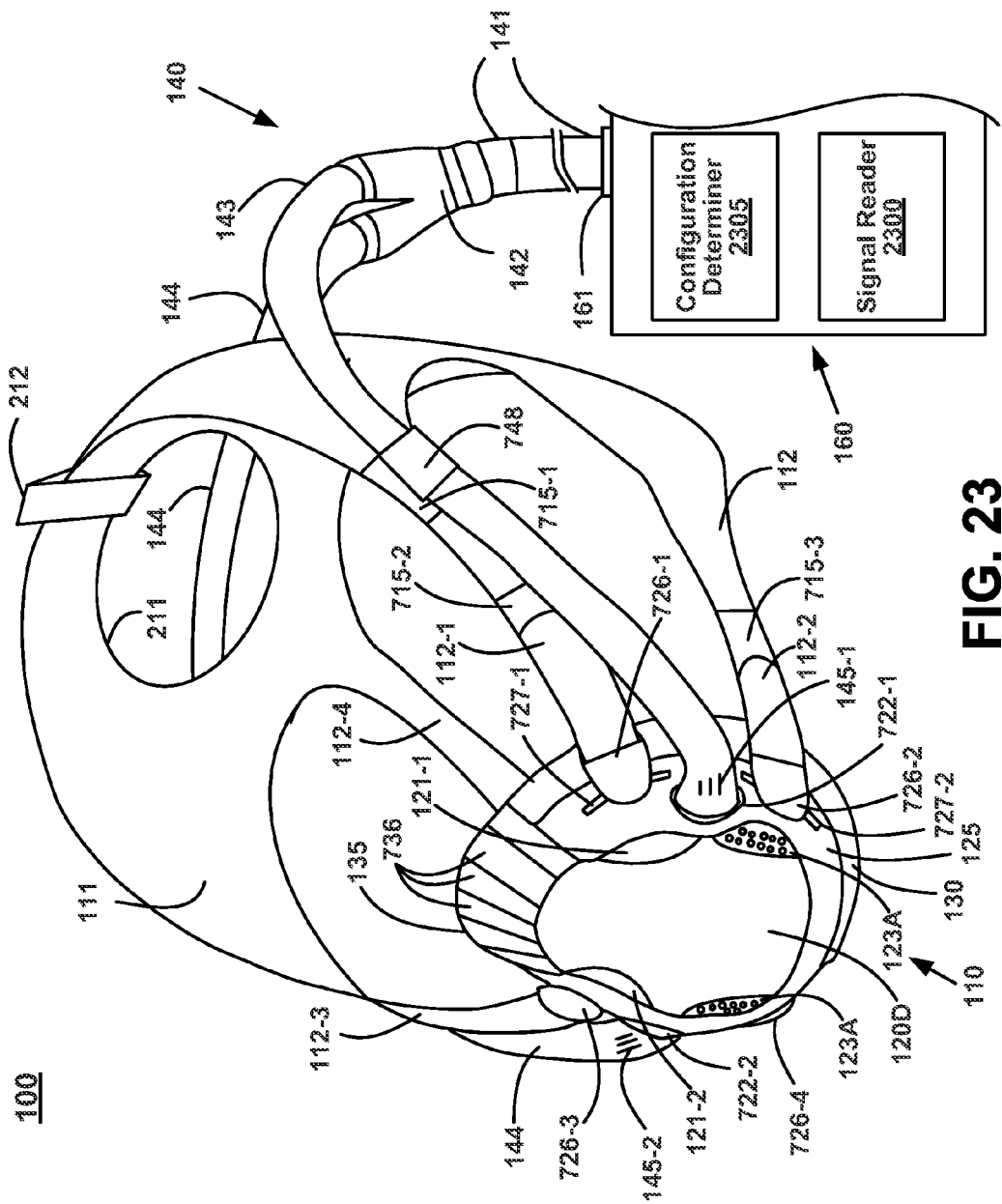
FIG. 23 is shows a front perspective view of a doffed patient interface of a non-invasive ventilation system with a smart component, in accordance with an embodiment, and also illustrates a ventilator with capability of determining system configuration, in accordance with an embodiment.

Referring to FIG. 23, a ventilator 160 is shown comprising a signal reader 2300 and a configuration determiner 2305. The breathing circuit 140 includes a wire lead 2304 for enabling the signal reader 2300 to determine continuity of at least a portion of breathing circuit 140. In one embodiment, the signal reader 2300 provides a signal to the electrical lead 2304 and determines continuity based on the signal returned.

In one embodiment, the signal can also be used to determine a configuration of the ventilation system. For example, various parts can have electrical components that enable the signal reader to identify which parts are in the system and can determine their configuration based on sending and receiving a signal over electrical leas 2304.

In another embodiment, one or more parts of the ventilation system include a machine readable identifier such as an RFID or barcode. In this embodiment, the signal reader 2300 is configured to read the corresponding barcode and/or RFID to perform system configuration and continuity checks. It is appreciated that in one embodiment, the configuration determiner 2305 is also configured to determine configuration information based on the RFID signal and/or barcode information.

Figure 24:
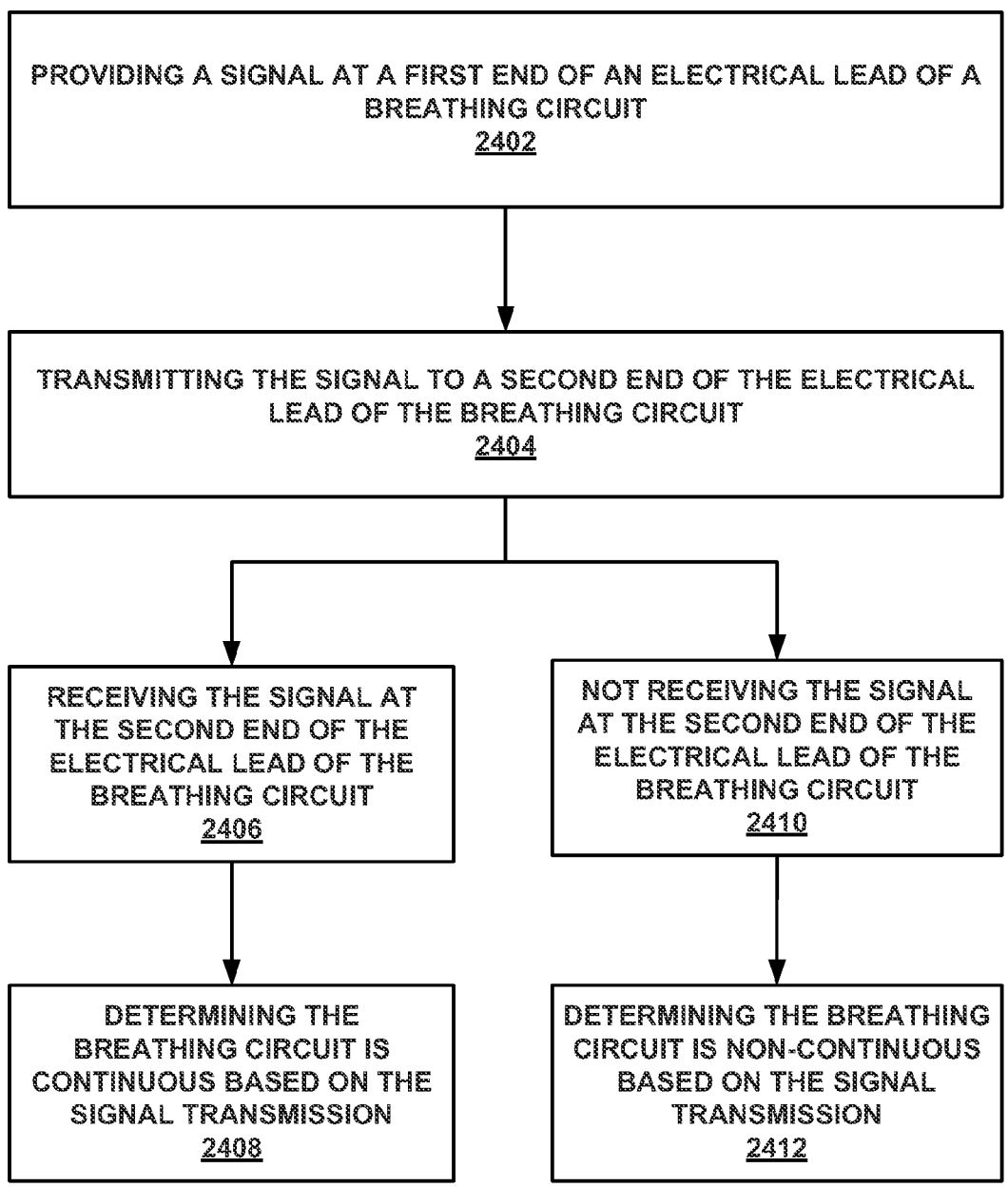
FIG. 24 is a flow diagram of an exemplary method for determining continuity of a ventilation system in accordance with an embodiment.

Referring to FIG. 24, a method 2400 for checking continuity of a breathing circuit is provided. At 2402, a signal is provided to a first end of an electrical lead of a breathing circuit. In one embodiment, one or more parts of the ventilation system include a wire lead that can be used to transmit a signal to determine continuity of that part and/or any parts coupled with that part.

At 2404, the signal is transmitted to a second end of the electrical lead. Provided the electrical lead is continuous, at 2406, the signal is received at a second end of the electrical lead and at 2408, it can be determined that the breathing circuit is continuous based on the received signal.

Provided the electrical lead is non-continuous, at 2410, the signal is not received at a second end of the electrical lead and at 2412, it can be determined that the breathing circuit is non-continuous based on the received signal. At this point, an alert can be generated to signal the breathing circuit is discontinuous and may need to be reconfigured.

Referring now to FIG. 25, a method 2500 for determining configuration of a breathing circuit is provided. At 2502, a signal is provided at a first end of an electrical lead of a breathing circuit. At 2504, the signal is transmitted to a second end of the electrical lead. At 2506, the signal is received at the second end of the electrical lead. At 2508, configuration of the breathing circuit is determined based on the signal received.

In one embodiment, as the signal is transmitted through the electrical lead, any number of modifications to the signal could be performed by any number of components in the system. The modification of the signal enables the signal reader 2300 of FIG. 23 to determine configuration of the breathing circuit. For example, a "smart" connector may include a microchip that enables access to real-time data associated with the part or the ventilation system as a whole.

Section 10: Tube Placement in Non-Invasive Ventilation

Figure 26A:
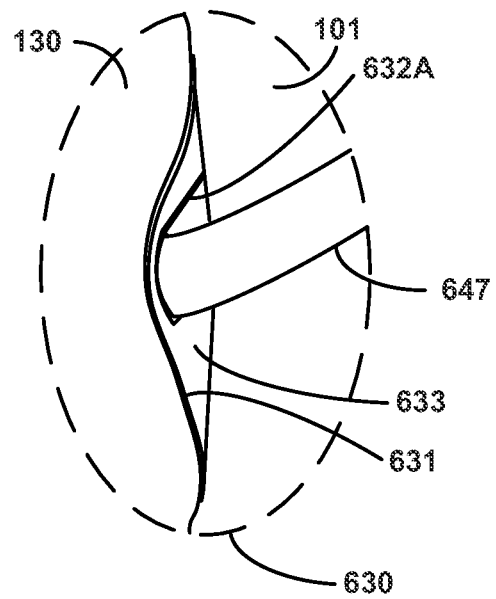
FIGS. 26A-26C illustrate detail views of a self-sealing tube insertion region, according to various embodiments.
Figure 26B:
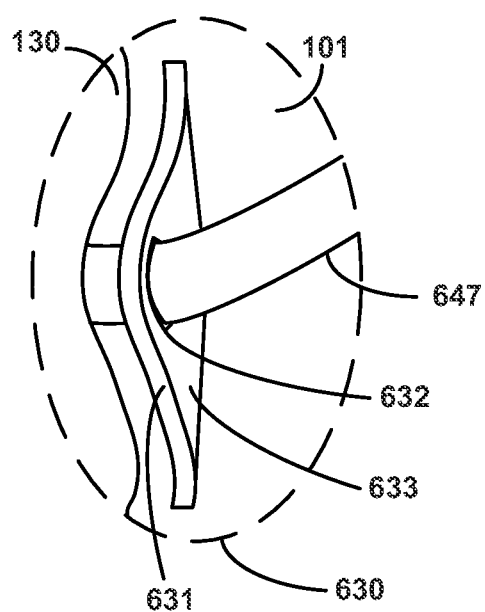
Figure 26C:
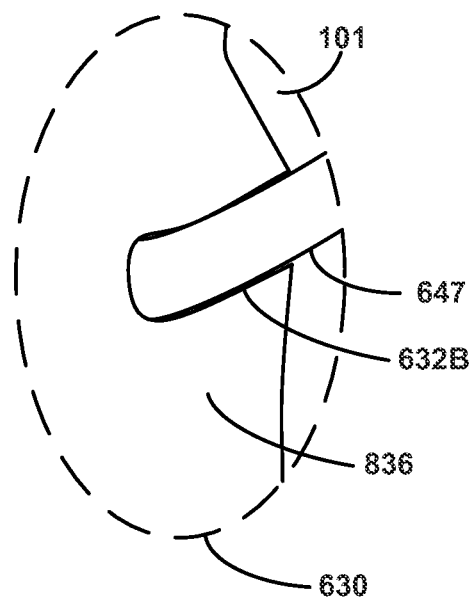

FIGS. 26A-26C illustrate detail views of a self-sealing tube insertion region 630, according to various embodiments. Some embodiments of a self-sealing tube insertion region 630 were previously described in conjunction with FIG. 6, and FIGS. 26A-26C further extrapolate on those embodiments.

As illustrated, in FIG. 26A, bridge 631 and cushioning material 633 (which defines and includes self-sealing tube opening 632 may be removably coupled with facial skin interface 130, in one embodiment. For example, bridge 631 may be coupled to facial skin interface 130 via an adhesive with a low shear force which may be used one or more times without exhausting its adhesion abilities. Additionally or alternatively, bridge 631 may be positioned and then held in place (as depicted in FIG. 6) by the securing force which is supplied by head strap system 111. By being removably coupled with facial skin interface 130, a portion of the tube insertion region can be decoupled from patient interface 110 when patient interface 110 is doffed. Tube 647 may be an orogastric tube, nasogastric tube, or carbon dioxide sampling tube. If tube 647 is orogastrically or nasogastrically inserted into patient 101, then this portion of tube insertion region can be decoupled from patient interface 110 when patient interface 110 is doffed. This allows the tube 647 to remain in place, without being removed or having its function interfered with in anyway by the doffing of patient interface 110.

As depicted in FIG. 26A self-sealing tube insertion region 630 can be coupled or decoupled with facial skin interface 130 and self-seals about tube 647 when tube 647 is disposed in opening 632, between the facial skin of patient 101 facial skin interface 130. As previously described, bridge 634 diverts this securing force around tube 647 while tube 647 is inserted in opening 632. Cushioning material 633 may be foam, silicone, TPE, or other cushioning material. In one embodiment, bridge 631 and cushioning material 633 may be the same material but in different thicknesses or configurations to provide different structural functionality (e.g., bridging versus cushioning/sealing). Cushioning material 633 seals opening 632 when tube 647 is not present expanding to fill opening 632 which may be a piercing through cushioning material 633. Similarly, cushioning material 633 conforms to tube 647, when inserted into opening 632, and self-seals around tube 647 to prevent unintentional leakage of gases from patient interface 110.

As depicted in FIG. 26B, in one embodiment, opening 632 may be a slit 632A defined within cushioning material 633. Tube 647 may be an orogastric tube, a nasogastric tube, a carbon dioxide sampling tube, a respiratory gas sampling tube, or other type of tube. Tube 647 can be inserted and removed from slit 632A without affecting positioning or function of tube 647. For example, if tube 647 is orogastrically or nasogastrically inserted into patient 101, tube 647 may be inserted or removed into slit 632A without removing tube 647 or disturbing the function of tube 647. Slit 632A comprises a self-sealing tube receiving opening, in that cushioning material 633 expands to removably seal about tube 647 when tube 647 is disposed in slit 632A. Similarly, cushioning material expands to seal slit 632A closed when tube 647 is not present. In some embodiments a removable, reusable (e.g., low shear force, low tack) adhesive is applied within slit 632A to facilitate sealing of slit 632A when no tube is present in slit 632A and to facilitate removable sealing of slit 632A about a tube 647 (when inserted).

As depicted in FIG. 26C, in one embodiment, opening 632 may be a gap 632B defined in a bladder feature 836 of facial skin interface 130. Gap 632B functions in a similar fashion to slit 632A. Gap 632B may be defined in a single bladder 836 or in a space between a pair of adjacent bladders 836. For example, if tube 647 is orogastrically or nasogastrically inserted into patient 101, tube 647 may be inserted or removed into gap 632B without removing tube 647 or disturbing the function of tube 647. Gap 632B comprises a self-sealing tube receiving opening, in that bladder feature 836 removably seals about tube 647 when tube 647 is disposed in gap 632B. This sealing can be due to one or more factors such as compressing of bladder feature 836 by the securing force supplied by head strap system 111 and/or by inflation of bladder(s) 836 by inhalation gases present within patient interface 110 and supplied from ventilator 160 (or by other source of gas or fluid). For example, the bladder(s) 836 may be sealably inflated around tube 647. Similarly, bladder feature 836 seals gap 632B closed when tube 647 is not present. In some embodiments a removable, reusable (e.g., low shear force, low tack) adhesive is applied within gap 632B to facilitate sealing of gap 632B when no tube is present in gap 632B and to facilitate removable sealing of gap 632B about a tube 647 (when inserted). As can be seen, tube 647 can be received in and removed from gap 632B independently of the donning and doffing of patient interface 110. When tube 647 is inserted within gap 632B, bladder feature 836 diverts the securing force (supplied by head strap system 111) around tube 647 such that tube 647 is not pressed against the facial skin of patient 101 to form a pressure point.

Section 11: Non-Invasive Ventilation Exhaust Gas Venting

As described previously with reference to FIG. 7, in one embodiment, filter media 123A can be used in conjunction with or in place or exhaust gas vent ports 123 which have been depicted elsewhere herein. Typically, exhaust gas vent ports 123 are open to the atmosphere. Instead of open vent holes, in one embodiment, filter media 123A is included in addition to vent ports 123 or alternatively utilized to replace vent ports 123. Filter media 123A filters contagions (e.g., bacteria, viruses, drugs (in particular aerosolized or nebulized drags), and/or chemicals) from the exhaust gas which is exhausted through filter media 123A. The exhausted gas may comprise exhaled breath, excess fresh respiratory gas, or a combination thereof. In addition to filtering, filter media 123A diffuses the gases that are exhausted there through. Filter media can be composed of any known type of respiratory gas filter media, including, but not limited to, paper, activated carbon, synthetic woven fiber (e.g., polyester, Gortex® or similar expanded polytetrafluoroethylene (ePTFE)), open cell foam, glass fiber, natural woven fiber (e.g., bamboo, cotton), or combination thereof.

In some embodiments, filter media 123A provides a controlled pressure drop in addition to filtering contagions from exhaled gases as the exhaled gases pass through. This controls an expulsion flow of exhaled breath and can also control an intentional leak rate of fresh respiratory gases from within patient interface 110. Such intentional leak rate control can manage the pressure of fresh respiratory gases within patient interface 110 such that a desired pressure range of continuous positive airway pressure is achieved. A variety of factors including one or more of composition, thickness, layers, surface area, and porosity of the media of filter media 123A can be selected, in some embodiments, to either filter contagions, provide a designated flow/intentional leak rate to control internal pressure of patient interface 110, or both.

In some embodiments, the filter media 123A can simultaneously filter and vent, thus eliminating the need have separate vent holes. In one embodiment, interchangeable patient interface insert 120D can be removed and replaced with a new interchangeable patient interface insert 120D when filter media 123A becomes clogged, soiled, or has surpassed its recommended replacement interval. In another embodiment, filter media 123A is, itself, replaceable.

In some embodiments, filter media 123A may be imbued with one or more substances. For example in one embodiment, filter media 123A may be imbued with a fragrance such as cinnamon, mint, peppermint, spearmint, wintergreen, citrus, fruit, bubblegum or the like in order to mask odors of exhaust gases which are not eliminated by filter media 123A. In one embodiment, filter media 123A, may be imbued with a desiccant (e.g., silica, activated charcoal, or the like) in order to assist in controlling moisture level on the interior of patient interface 110 to reduce fogging and/or to improve patient comfort, and in order to maintain filter media 123A in a dry state which is can kill viruses and is non-conducive to formation of funguses. Along these lines, transparent portions of domed front portion 120 or similar interchangeable insert 120D (and the like) may have interior portions coated with an anti-fog coating to prevent fogging and to maintain transparency both for patient comfort and so that medical personnel may easily view inside of patient interface 110. In one embodiment, filter media 123A is imbued with an antibacterial, antimicrobial, and/or antifungal substance (e.g., silver, an antibiotic, etc.)

Figure 27:
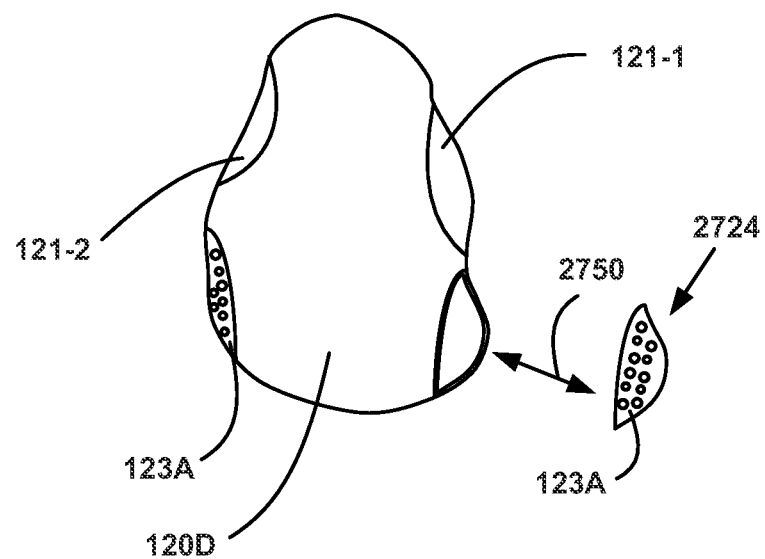
FIG. 27 illustrates a replaceable filter cartridge, in accordance with an embodiment.

FIG. 27 illustrates a replaceable filter cartridge 2724, in accordance with some embodiment. Filter cartridge 2724 is shown in an uninstalled state. Arrow 2750 illustrates where filter cartridge 2724 may be snap fit or otherwise coupled with interchangeable insert 120D, or a similar interchangeable or non-interchangeable domed front portion 120. This is one mechanism for changing for replacing filter media 123 when clogged or past a time of suggested usability. In other embodiments, filter media 123A is an integral portion of interchangeable insert 120D (rather than a replaceable cartridge), and the entirety of interchangeable insert 120D is removed and replaced in order to replace filter media 123. In some embodiments a larger portion of interchangeable insert 120D may be composed of filter media 123 than depicted in FIG. 27 or other figures herein. For example, in some embodiments up to the entire visible exterior surface of interchangeable insert 120D may be composed of one or some combination of filter materials.

Section 12: Non-Invasive Ventilation Facial Skin Protection

Many features for skin protection have been discussed previously herein. Additional features which may be used alone or in combination with the previously discussed skin protection features (or with other skin protection features that are described in Section 13) include features which eliminate fluid via wicking and/or purging, and features which utilize an imbued substance to actively soothe/protect the facial skin in one or more areas which receive contact from a patient interface as a result of non-invasive ventilation.

Figure 28:
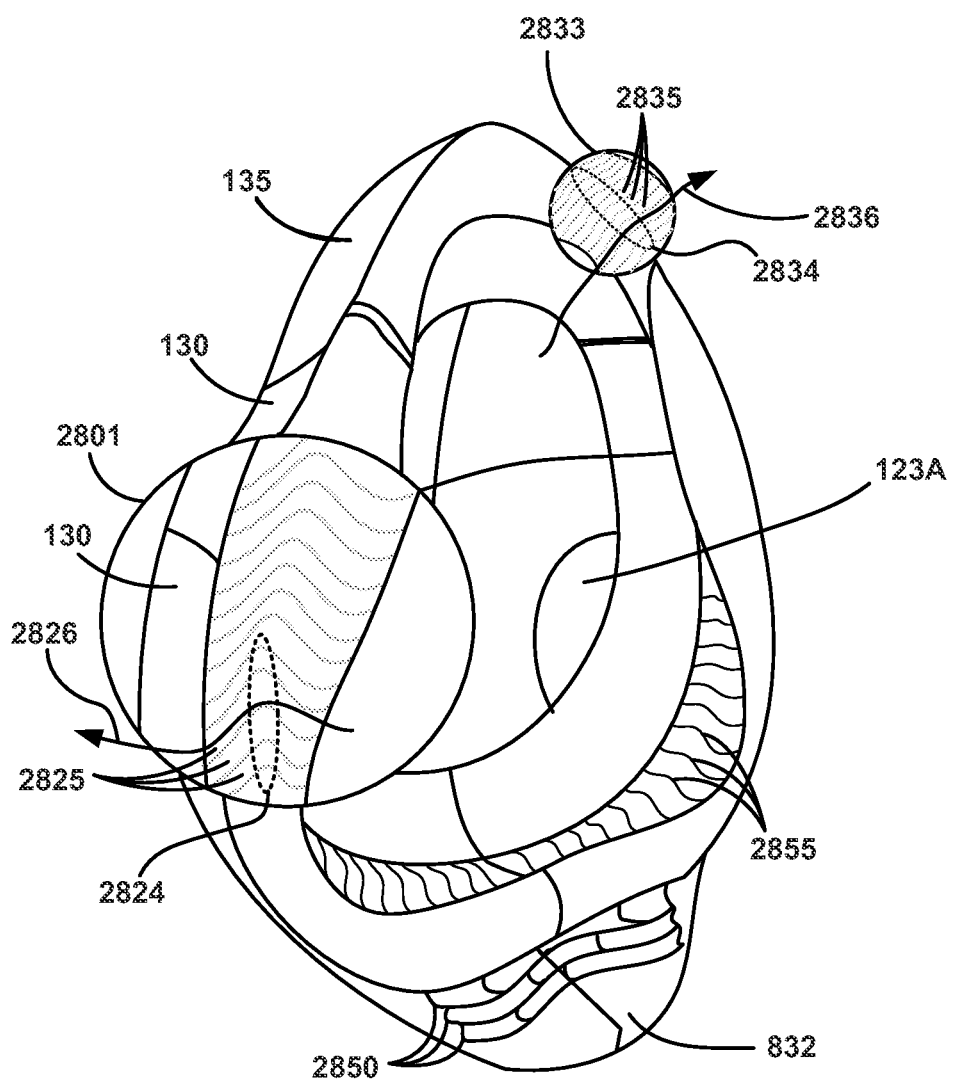
FIG. 28 illustrates a perspective view of the skin contacting portion of a compliant nose bridge seal and a facial skin interface, according to an embodiment.

FIG. 28 illustrates a perspective view of the skin contacting portion of a compliant nose bridge seal 135 and a facial skin interface 130, according to an embodiment. As illustrated by enlarged detail 2801, the skin contacting portion of facial skin interface 130 is configured with a plurality of micro-grooves 2825 which provide small passageways between skin contacting peaks 2824 which allow air flow. In one embodiment, micro-grooves 2825 may be 0.075 inches or narrower in width, in another embodiment some of micro-grooves 2825 may be 0.050 inches or narrower in width. In one embodiment, some or all of microgrooves 2825 may be between 0.075 and 0.005 inches in width. When patient interface 110 is donned and coupled with ventilator 160, pressurized fresh respiratory gas flows through micro-grooves 2825 in a controlled and intentional leak as illustrated by gas flow path 2826. This controlled and intentional leak facilitates a controlled purging of moisture by both forcing moisture out through micro-grooves 2825, and by evaporating moisture. This controlled leak assists in purging moisture and thus preventing accumulation of fluids (e.g., sweat, condensation, or the like) and/or eliminating fluids from within facial interface 110 (the portion which covers nose and/or mouth openings when donned) and from between facial skin interface 130 and the facial skin of patient 101 that is in contact with facial skin interface 130 when patient interface 110 is donned. In one embodiment, micro-grooves 2825 may be a removable/replaceable component which is removably coupled with facial skin interface 130. Thus when micro-grooves 2825 get clogged or exceed a recommended service time, this replaceable component can be replaced.

As illustrated in FIG. 28 by enlarged detail 2833, the skin contacting portion of compliant nose bridge seal 135 may additionally or alternatively be configured with a plurality of micro-grooves 2835 which provide small passageways between skin contacting peaks 2834 which allow air flow. In one embodiment, micro-grooves 2835 may be 0.075 inches or narrower in width, in another embodiment some of micro-grooves 2835 may be 0.050 inches or narrower in width. In one embodiment, some or all of microgrooves 2835 may be between 0.075 and 0.005 inches in width. When patient interface 110 is donned and coupled with ventilator 160, pressurized fresh respiratory gas flows through micro-grooves 2835 in a controlled and intentional leak as illustrated by gas flow path 2836. This controlled and intentional leak facilitates a controlled purging of moisture by both forcing moisture out through micro-grooves 2835, and by evaporating moisture. This controlled and intentional leak assists in purging moisture and thus preventing accumulation of fluids (e.g., sweat, condensation, or the like) and/or eliminating fluids from within facial interface 110 (the portion which covers nose and/or mouth openings when donned) and from between compliant nose bridge seal 135 and the facial skin of patient 101 that is in contact with compliant nose bridge seal 135 when patient interface 110 is donned. In one embodiment, micro-grooves 2835 may be a removable/replaceable component which is removably coupled with compliant nose bridge seal 135. Thus when micro-grooves 2835 get clogged or exceed a recommended service time, this replaceable component can be replaced.

As illustrated in FIG. 28, in one embodiment, facial skin interface 130 additionally or alternatively includes an extended chin portion 832, which may include a chin bellows 2850 and/or a jaw bellows 2855. Chin bellows 2850 and jaw bellows 2855 each include a plurality of bellows formed of a cushioning material such as silicone. In various embodiments, chin bellows 2850 and/or jaw bellows 2855 may be formed of the same material as facial skin interface 130. Chin bellows 2850 expands and contracts in response to up and down movement of the chin of patient 101, such as when patient 101 opens and closes his/her mouth during speaking. Jaw bellows 2850 is inboard of the sealing surface of facial skin interface 130, and expands and contracts in response to up, down, and side-to-side movement of the jaw of patient 101, such as when patient 101 opens and closes his/her mouth during speaking, yawning, or for a medical procedure accomplished through an open front portion of patient interface 110. The expansion and contraction provided by chin bellows 2850 and/or jaw bellows 2855 allows for some linear and/or side-to-side movement of the mouth, chin and/or jaw of patient 101 while maintaining contact between facial skin interface 130 and the face of patient 101. This can increase patient comfort and decrease the need to constantly manually adjust patient interface 101 in response to unintentional leaks caused by movement of the jaw and/or chin of patient 101. Additionally, a caregiver or patient may access an oral or nasal opening or region through a removable insert 120 and jostle or move portions of patient interface 110 without causing unintentional leaks. This is because the accordion like bellows features of chin bellows 2850 and/or jaw bellows 2855 allow for some flexing movement such that outer portions of patient interface 110 while the facial skin contacting portions remain undisturbed or relatively undisturbed in their seating against the facial skin of the patient.

Figure 29:
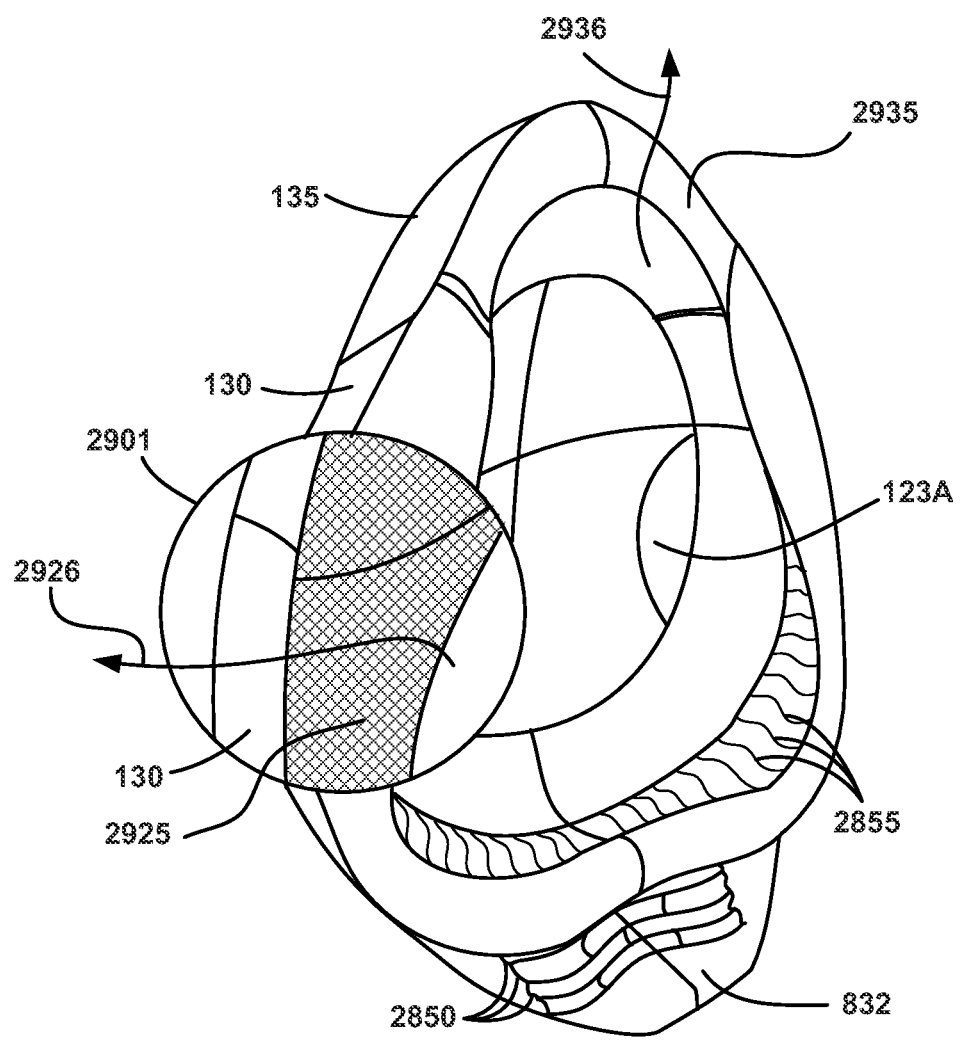
FIG. 29 illustrates a perspective view of the skin contacting portion of a compliant nose bridge seal and a facial skin interface, according to an embodiment.

FIG. 29 illustrates a perspective view of the skin contacting portion of a compliant nose bridge seal 135 and a facial skin interface 130, according to an embodiment. As illustrated by enlarged detail 2901, the skin contacting portion of facial skin interface 130 comprises a porous material 2925 (e.g., open cell foam) which provides a plurality of small openings and small passageways in/near its surface, due to the porosity. When patient interface 110 is donned and coupled with ventilator 160, pressurized fresh respiratory gas flows through porous material 2925 in a controlled and intentional leak as illustrated by gas flow path 2926. This controlled and intentional leak facilitates a controlled purging of moisture by both forcing moisture out through the pores of porous material 2925, and by evaporating moisture. This controlled and intentional leak assists in purging moisture and thus preventing accumulation of fluids (e.g., sweat, condensation, or the like) and/or eliminating fluids from within facial interface 110 (the portion which covers nose and/or mouth openings when donned) and from between facial skin interface 130 and the facial skin of patient 101 that is in contact with facial skin interface 130 when patient interface 110 is donned. In one embodiment, porous material 2925 may be a removable/replaceable component which is removably coupled with facial skin interface 130. Thus when porous material 2925 gets clogged or exceeds a recommended service time, this replaceable component can be replaced.

As illustrated in FIG. 29, the skin contacting portion of compliant nose bridge seal 135 may additionally or alternatively be configured with a similar porous material 2935 which provide small passageways and openings in/near its surface, due to the porosity. When patient interface 110 is donned and coupled with ventilator 160, pressurized fresh respiratory gas flows through pores of porous material 2935 in a controlled and intentional leak as illustrated by gas flow path 2936. This controlled and intentional leak facilitates a controlled purging of moisture by both forcing moisture out through pores of porous material 2935, and by evaporating moisture. This controlled leak assists in purging moisture and thus preventing accumulation of fluids (e.g., sweat, condensation, or the like) and/or eliminating fluids from within facial interface 110 (the portion which covers nose and/or mouth openings when donned) and from between compliant nose bridge seal 135 and the facial skin of patient 101 that is in contact with compliant nose bridge seal 135 when patient interface 110 is donned. In one embodiment, porous material 2935 may be a removable/replaceable component which is removably coupled with compliant nose bridge seal 135. Thus when porous material 2935 gets clogged or exceeds a recommended service time, this replaceable component can be replaced.

As illustrated in FIG. 29, in one embodiment, facial skin interface 130 additionally or alternatively includes an extended chin portion 832, which may include a chin bellows 2850 and/or may include a jaw bellows 2850.

Figure 30:
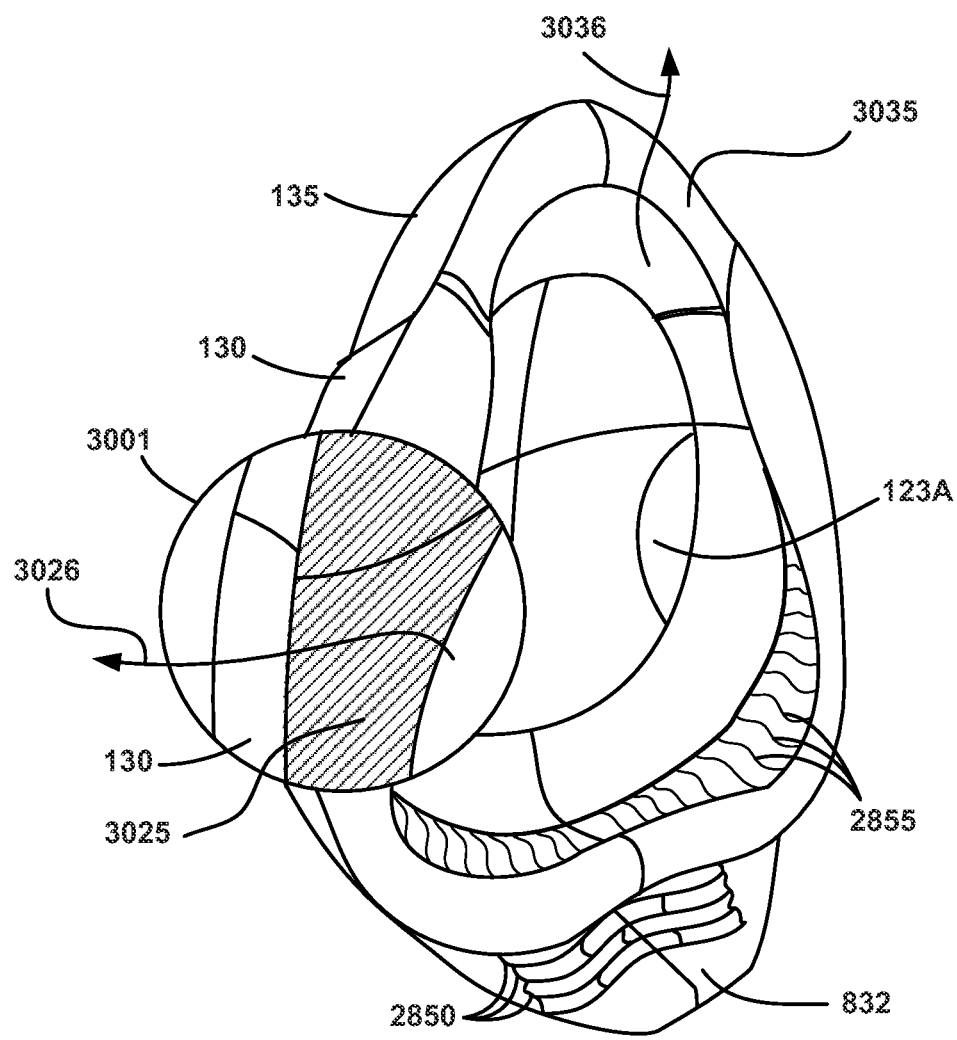
FIG. 30 illustrates a perspective view of the skin contacting portion of a compliant nose bridge seal and a facial skin interface, according to an embodiment.

FIG. 30 illustrates a perspective view of the skin contacting portion of a compliant nose bridge seal 135 and a facial skin interface 130, according to an embodiment. As illustrated by enlarged detail 3001, the skin contacting portion of facial skin interface 130 is comprises a wicking material 3025 (e.g., a woven cloth such as cotton, wool, bamboo, polyester micro fiber, or other known wicking materials) which provides a surface that naturally wicks fluids and moisture. In some embodiments, the wicking surface of facial skin interface 130 may be textured. This wicking property assists in wicking moisture and thus preventing accumulation of fluids (e.g., sweat, condensation, or the like) and/or eliminating fluids from within facial interface 110 (the portion which covers nose and/or mouth openings when donned) and from between facial skin interface 130 and the facial skin of patient 101 that is in contact with facial skin interface 130 when patient interface 110 is donned. In one embodiment, wicking material 3025 may be a removable/replaceable component which is removably coupled with facial skin interface 130. Thus when wicking material 3025 gets clogged, saturated, or exceeds a recommended service time; this replaceable component can be replaced. In some embodiments, the wicking material 3024 may be porous enough to exhibit purging properties as well as wicking properties. Arrow 3026 illustrates the direction of gas flow through a porous wicking material 3024.

As illustrated in FIG. 30, the skin contacting portion of compliant nose bridge seal 135 may additionally or alternatively be configured with a similar wicking material 3035 (e.g., a woven cloth such as cotton, wool, bamboo, polyester micro fiber, or other known wicking materials) which provides a textured surface that naturally wicks fluids and moisture. Wicking material 3035 provides a textured wicking surface for interfacing with nasal skin of patient 101 when patient interface 110 is donned. This wicking property assists in wicking moisture and thus preventing accumulation of fluids (e.g., sweat, condensation, or the like) and/or eliminating fluids from within facial interface 110 (the portion which covers nose and/or mouth openings when donned) and from between compliant nose bridge seal 135 and the facial skin of patient 101 that is in contact with compliant nose bridge seal 135 when patient interface 110 is donned. In one embodiment, wicking material 3035 may be a removable/replaceable component which is removably coupled with compliant nose bridge seal 135. Thus when wicking material 3035 gets clogged, saturated, or exceeds a recommended service time; this replaceable component can be replaced. In some embodiments, wicking material 3034 may be porous enough to exhibit purging properties as well as wicking properties. Arrow 3036 illustrates the direction of gas flow through a porous wicking material 3034.

As illustrated in FIG. 30, in one embodiment, facial skin interface 130 additionally or alternatively includes an extended chin portion 832, which may include a chin bellows 2850 and/or may include a jaw bellows 2850.

In some embodiments, all or a portion of facial skin interface 130, compliant nose bridge seal 135, micro-grooves 2825, porous material 3925, and/or wicking material 3025 is imbued with one or more substances which actively soothe/protect the facial skin in one or more areas which receive contact from a patient interface as a result of non-invasive ventilation. Such substances may include one or more of an antibacterial substance (e.g., tricolsan, silver, or other known substances with antibacterial and/or antifungal properties), an emollient, and/or a vasodilator. An imbued antibacterial can prevent/destroy a bacteria and/or a fungus which may inhabit the environment where facial skin of a patient contacts or is enclosed by patient interface 110. An imbued emollient softens and moisturizes the skin, and can thus assist in prevention of chafing, rashes, and skin necrosis caused by prolonged contact between patient interface 110 and facial skin of patient 101. A imbued vasodilator dilates (widens) blood vessels by relaxing smooth muscle cells of the vessel walls, thus improving blood flow in facial skin. Such improved blood flow can assists in preventing necrosis that can occur if patient interface 110 causes a pressure point on facial skin of patient 101, or can prolong the amount of time that patient interface 110 can be worn without damaging facial skin of patient 101.

In some or all embodiments, all or portions of facial skin interface 130 may be treated with a low shear force adhesive such that a slight tackiness (similar to that of a Post-It® note) is achieved. This tackiness improves mask stability, thus reducing the amount of sliding and decreasing irritation to the skin caused by constant sliding and shifting.

Section 13: Non-Invasive Ventilation Facial Skin Protection

Referring again to FIG. 8A, a patient interface which includes a zygomatic facial interface 831 (831-1, 831-2) is illustrate, according to an embodiment. In one embodiment, zygomatic facial interface is an extension of or is coupled with facial skin interface 130. In one embodiment, first zygomatic interface portion 831-1 sealably interfaces with facial skin covering a left zygomatic arch region of patient 101, while second zygomatic interface portion sealably interfaces with facial skin covering a right zygomatic arch region of patient 101. In response to application of a securing force for securing patient interface 110 and facial skin interface 130 over a mouth and/or nose opening of said patient, first portion 831-1 and second portion 831-2 spreading the securing force away from a nasal bridge of patient 101 and onto to the left and right zygomatic arch regions of patient 101. The securing force is supplied by a head strap system, such as or similar to head strap system 111, which supplies the securing force in response to donning of patient interface 110. In one embodiment, zygomatic facial interface 831 may comprise a plurality of bladders 836, which may be inflated with a fluid or may be inflated with fresh respiratory gas supplied by ventilator 160. In some embodiments, zygomatic facial interface 831 includes a moisture purging feature (e.g., micro-grooves 2825 and/or porous material 3025) which contacts facial skin of patient 101 and which allows/facilitates a controlled and intentional leak of fresh respiratory gas between the moisture purging feature and the facial skin of patient 101. In one embodiment, zygomatic facial interface 831 includes a wicking feature (e.g., wicking material 3025) which contacts facial skin of patient 101 and wicks fluid from the contacted facial skin. In one embodiment, a skin contacting region of zygomatic facial interface 831 is imbued with at least one of an emollient, an antibacterial, and a vasodilator. In one embodiment, a skin contacting region of zygomatic facial interface is imbued with two or more of an emollient, an antibacterial, and a vasodilator.

In various embodiments, a patient interface 110 which utilizes zygomatic facial interface 831 may include extended chin portion 832 (which may further include chin bellows 2850). It is appreciated that other features described herein may be included, in various combinations with a patient interface 110 which includes zygomatic facial skin interface 831. For example, in some embodiments, a patient interface 110 which utilizes zygomatic facial interface 831 may include compliant nose bridge seal 135, corrugations, jaw bellows, tube insertion region, microgrooves, porous material, wicking material, and nasal passage opening features, among other features.

Although features have been illustrated and described herein as applied to oral/nasal patient interfaces which seal about the mouth and nose openings of a patient, it is appreciated that the features described herein may also be applied to patient interfaces which seal only about a mouth opening of a patient or only about a nose opening of a patient.

The foregoing descriptions of specific embodiments have been presented for purposes of illustration and description. They are not intended to be exhaustive or to limit the presented technology to the precise forms disclosed, and obviously many modifications and variations are possible in light of the above teaching. The figures and embodiments were chosen and described in order to best explain the principles of the presented technology and its practical application, to thereby enable others skilled in the art to best utilize the presented technology and various embodiments with various modifications as are suited to the particular use contemplated. While the subject matter has been described in particular embodiments, it should be appreciated that the subject matter should not be construed as limited by such embodiments, but rather construed according to the following claims.

The invention claimed is:

1. A carbon-dioxide sampling system for accurately monitoring carbon dioxide in exhaled breath, said system comprising:
  a ventilator configured to ventilate a patient with respiratory gases, comprising:
    a carbon-dioxide sampling control unit; and
    a carbon-dioxide analyzer;
  wherein said carbon-dioxide sampling control unit is configured to control the timing of sampling of carbon dioxide in the exhaled breath of a patient, and to control the timing of an analysis of exhaled gases by said carbon-dioxide analyzer, and
  wherein said carbon-dioxide sampling control unit is configured to control collection of a sample of said exhaled breath from said patient that is substantially undiluted by respiratory gases supplied for said patient's breathing.

2. The carbon-dioxide sampling system of claim 1, further comprising:
  a breath-sampling chamber configured to be disposed over a respiratory opening of a patient, configured to seal with said patient's face preventing unintentional leakage of respiratory gases from said chamber, and coupled with said ventilator.

3. The carbon-dioxide sampling system of claim 2, further comprising:
  a carbon-dioxide collector disposed in said breath-sampling chamber.

4. The carbon-dioxide sampling system of claim 2, wherein said system further comprises:
  an exhalation-gas collection line coupled to said breath-sampling chamber configured to collect exhaled gases in a breath exhaled by said patient, and to transport said exhaled gases to said carbon-dioxide analyzer.

5. The carbon-dioxide sampling system of claim 1, wherein said ventilator further comprises a ventilation timing unit:
  wherein said carbon-dioxide analyzer is configured to regulate said ventilation timing unit to ventilate a patient at regular intervals based on measured levels of carbon dioxide in said breath of said patient.

6. The carbon-dioxide sampling system of claim 1, wherein said carbon-dioxide analyzer further comprises a carbon-dioxide sensor configured to sense a level of carbon dioxide in said exhaled breath of said patient, and to output a sensor signal commensurate with said level of carbon dioxide.

7. The carbon-dioxide sampling system of claim 6, wherein said carbon dioxide analyzer comprises a sensor-signal converter configured to convert said sensor signal into a measurement of carbon dioxide content in said sample of said exhaled breath from said patient.

8. The carbon-dioxide sampling system of claim 7, wherein said carbon dioxide analyzer further comprises a carbon-dioxide analysis protocol executor to provide an accurate measurement of carbon dioxide content in said sample of said exhaled breath from said patient that is substantially unaffected by dilution from respiratory gases supplied for said patient's breathing.

9. The carbon-dioxide sampling system of claim 6, wherein said carbon-dioxide sensor comprises an infra-red detector, said infra-red detector configured to measure the absorbance of infra-red radiation at a frequency within an absorption band of carbon dioxide for said infra-red radiation, and to generate a sensor signal commensurate with said level of carbon dioxide.

10. A combined non-invasive patient interface and carbon-dioxide sampling system for accurately monitoring carbon dioxide in exhaled breath, said combined interface and system comprising:
a non-invasive patient interface comprising:
a carbon-dioxide sampling device for non-invasively measuring carbon dioxide in exhaled breath, comprising:
a breath-sampling chamber configured to be disposed over a respiratory opening of a patient, and configured to seal with said patient's face preventing unintentional leakage of respiratory gases from said chamber; and
a carbon-dioxide collector disposed in a fluid dynamically isolated fashion in said breath-sampling chamber;
wherein said carbon-dioxide collector is configured to be disposed in proximity to, and outside of, said respiratory opening of said patient, and to collect a sample of said exhaled breath from said patient; and
a carbon-dioxide sampling system for accurately monitoring carbon dioxide in exhaled breath, comprising:
a ventilator configured to ventilate a patient with respiratory gases, and to couple with said non-invasive patient interface, said ventilator comprising:
a carbon-dioxide sampling control unit; and
a carbon-dioxide analyzer;
wherein said carbon-dioxide sampling control unit is configured to control the timing of sampling of carbon dioxide in the exhaled breath of a patient, and to control the timing of the analysis of exhaled gases by said carbon-dioxide analyzer.

11. The combined non-invasive patient interface and carbon-dioxide sampling system of claim 10, wherein said breath-sampling chamber comprises a respiration chamber of a breathing mask.

12. The combined non-invasive patient interface and carbon-dioxide sampling system of claim 10, further comprising:
a breath-sampling line configured to transport a sample of said exhaled breath from said patient to said carbon-dioxide analyzer.

13. The combined non-invasive patient interface and carbon-dioxide sampling system of claim 10, further comprising:
an inhalation gas supply line coupled with said breath-sampling chamber, and configured to transport oxygen gas to said patient; and
an exhalation gas collection line coupled with said breath-sampling chamber, and configured to remove exhaled gases from said breath-sampling chamber, and to transport a sample of said exhaled breath from said patient to said carbon-dioxide analyzer.

14. The combined non-invasive patient interface and carbon-dioxide sampling system of claim 13, wherein said exhalation gas collection line is securely attached to said breath-sampling chamber, and configured to prevent accidental interference by said patient with said exhalation gas collection line.

15. The combined non-invasive patient interface and carbon-dioxide sampling system of claim 10, further comprising:
a carbon-dioxide indicator configured to indicate when a threshold level of carbon dioxide is exceeded in said exhaled breath from said patient.

16. The combined non-invasive patient interface and carbon-dioxide sampling system of claim 15, wherein said carbon-dioxide indicator is mounted conspicuously on a portion of said non-invasive patient interface so as to be readily observable by an attendant of said patient.

17. A method for accurately monitoring carbon dioxide in exhaled breath, said method comprising:
timing a sampling of carbon dioxide in an exhaled breath of a patient with a carbon-dioxide sampling control unit; and
controlling the timing of an analysis of gases in an exhaled breath of a patient with a carbon-dioxide analyzer;
wherein said carbon-dioxide sampling control unit is configured to control collection of a sample of said exhaled breath from said patient that is substantially undiluted by respiratory gases supplied for said patient's breathing.

18. The method of claim 17, further comprising:
regulating a ventilation timing unit to ventilate a patient at regular intervals based on measured levels of carbon dioxide in said breath of said patient.

19. The method of claim 17, further comprising:
applying a carbon-dioxide analysis protocol to provide an accurate measurement of carbon dioxide content in said sample of said exhaled breath from said patient that is substantially unaffected by dilution from respiratory gases supplied for said patient's breathing.

20. A carbon-dioxide sampling system for accurately monitoring carbon dioxide in exhaled breath, said system comprising:
a ventilator configured to ventilate a patient with respiratory gases, comprising:
a carbon-dioxide sampling control unit;
a carbon-dioxide analyzer; and
a ventilation timing unit,
wherein said carbon-dioxide sampling control unit is configured to control the timing of sampling of carbon dioxide in the exhaled breath of a patient, and to control the timing of an analysis of exhaled gases by said carbon-dioxide analyzer, and
wherein said carbon-dioxide analyzer is configured to regulate said ventilation timing unit to ventilate a patient at regular intervals based on measured levels of carbon dioxide in said breath of said patient.

21. A carbon-dioxide sampling system for accurately monitoring carbon dioxide in exhaled breath, said system comprising:
- a ventilator configured to ventilate a patient with respiratory gases, comprising:
    - a carbon-dioxide sampling control unit; and
    - a carbon-dioxide analyzer comprising (i) a carbon-dioxide sensor configured to sense a level of carbon dioxide in said exhaled breath of said patient, and to output a sensor signal commensurate with said level of carbon dioxide, (ii) a sensor-signal converter configured to convert said sensor signal into a measurement of carbon dioxide content in said sample of said exhaled breath from said patient, and (iii) a carbon-dioxide analysis protocol executor to provide an accurate measurement of carbon dioxide content in said sample of said exhaled breath from said patient that is substantially unaffected by dilution from respiratory gases supplied for said patient's breathing.

* * * * *